(12) United States Patent
Schneider et al.

(10) Patent No.: US 8,352,193 B2
(45) Date of Patent: Jan. 8, 2013

(54) METHODS FOR DERIVING A CUMULATIVE RANKING

(75) Inventors: Luke V. Schneider, Half Moon Bay, CA (US); Michael P. Hall, Hayward, CA (US); Robert Petesch, Newark, CA (US)

(73) Assignee: Target Discovery, Inc., Palo Alto, CA (US)

( * ) Notice: Subject to any disclaimer, the term of this patent is extended or adjusted under 35 U.S.C. 154(b) by 551 days.

(21) Appl. No.: 11/444,215

(22) Filed: May 30, 2006

(65) Prior Publication Data

US 2007/0154900 A1 Jul. 5, 2007

Related U.S. Application Data

(63) Continuation of application No. 10/033,303, filed on Oct. 19, 2001, now abandoned.

(60) Provisional application No. 60/242,165, filed on Oct. 19, 2000, provisional application No. 60/242,398, filed on Oct. 19, 2000.

(51) Int. Cl.
*G01N 33/48* (2006.01)
*G01N 31/00* (2006.01)

(52) U.S. Cl. ............................ 702/19; 702/22

(58) Field of Classification Search .................. None
See application file for complete search history.

(56) References Cited

U.S. PATENT DOCUMENTS

| | | | |
|---|---|---|---|
| 4,830,010 A | 5/1989 | Marshall | |
| 4,842,701 A | 6/1989 | Smith et al. | |
| 4,994,165 A | 2/1991 | Lee et al. | |
| 5,100,778 A | 3/1992 | Rademacher et al. | |
| 5,174,962 A | 12/1992 | Brennan | |
| 5,306,412 A | 4/1994 | Whitehouse et al. | |
| 5,386,832 A | 2/1995 | Wagner et al. | |
| 5,470,753 A | 11/1995 | Sepetov et al. | |
| 5,505,832 A | 4/1996 | Laukien et al. | |
| 5,538,897 A | 7/1996 | Yates, III et al. | |

(Continued)

FOREIGN PATENT DOCUMENTS

JP 2004203897 7/2004

(Continued)

OTHER PUBLICATIONS

Ashok R. Dongre, Jimmy K. Eng and John Yates III, "Emerging tandem-mass-spectrometry techniques for the rapid identification of proteins," *Trends in Biotechnology*, vol. 15 (Oct. 1, 1997), pp. 418-425.

(Continued)

*Primary Examiner* — Larry D Riggs, II
(74) *Attorney, Agent, or Firm* — Kilpatrick Townsend & Stockton LLP

(57) ABSTRACT

Methods and apparatuses for deriving the sequence of an oligomer. In one exemplary method for deriving the sequence of a polypeptide, a predetermined set of mass/charge values for amino acid sequences is stored. An abundance value from mass spectrum data for each mass/charge value in the predetermined set is determined to produce a plurality of abundance values. A first ranking, based on the plurality of abundance values, is calculated for each sequence of a set of amino acid sequences having a first number of amino acids. A second ranking, based on the plurality of abundance values, for each sequence of a set of amino acid sequences having a second number of amino acids is calculated. A cumulative ranking, based on the first ranking and the second ranking, is calculated for each sequence of a set of amino acid sequences having at least the second number of amino acids.

19 Claims, 40 Drawing Sheets

U.S. PATENT DOCUMENTS

| | | | |
|---|---|---|---|
| 5,625,184 | A | 4/1997 | Vestal et al. |
| 5,667,984 | A | 9/1997 | Parekh et al. |
| 5,691,141 | A | 11/1997 | Koster |
| 5,700,642 | A | 12/1997 | Monforte et al. |
| 5,827,659 | A | 10/1998 | Patterson |
| 5,856,082 | A | 1/1999 | Aebersold et al. |
| 5,872,010 | A | 2/1999 | Karger et al. |
| 5,919,709 | A | 7/1999 | Parmelee et al. |
| 5,952,653 | A | 9/1999 | Covey et al. |
| 5,953,653 | A | 9/1999 | Josenhans et al. |
| 5,995,989 | A | 11/1999 | Gedcke et al. |
| 6,004,770 | A | 12/1999 | Nelson |
| 6,017,693 | A | 1/2000 | Yates, III et al. |
| 6,027,890 | A | 2/2000 | Ness et al. |
| 6,056,926 | A | 5/2000 | Sugarman et al. |
| 6,090,558 | A | 7/2000 | Butler et al. |
| 6,194,144 | B1 | 2/2001 | Koster |
| 6,277,644 | B1 | 8/2001 | Farnsworth et al. |
| 6,287,780 | B1 | 9/2001 | Schmidt |
| 6,329,146 | B1 | 12/2001 | Cooke et al. |
| 6,335,525 | B1 | 1/2002 | Takada et al. |
| 6,359,111 | B1 | 3/2002 | Meyer et al. |
| 6,379,971 | B1 | 4/2002 | Schneider et al. |
| 6,391,649 | B1 | 5/2002 | Chait et al. |
| 6,582,965 | B1 | 6/2003 | Townsend et al. |
| 6,677,114 | B1 | 1/2004 | Schneider et al. |
| 6,706,529 | B2 | 3/2004 | Schneider et al. |
| 6,962,818 | B2 | 11/2005 | Schneider et al. |
| 7,316,931 | B2 | 1/2008 | Schneider et al. |
| 2002/0168842 | A1 | 11/2002 | Nguyen et al. |
| 2005/0147985 | A1 | 7/2005 | Pappin et al. |

FOREIGN PATENT DOCUMENTS

| | | |
|---|---|---|
| JP | 2004519665 | 7/2004 |
| JP | 2004521616 | 7/2004 |
| JP | 2004522980 | 7/2004 |
| JP | 2005241161 A | 9/2005 |
| JP | 2005533102 | 11/2005 |
| JP | 2005536505 | 12/2005 |
| JP | 2006505115 | 2/2006 |
| WO | WO 96/33406 A1 | 10/1996 |
| WO | WO 99/32501 A1 | 7/1999 |
| WO | WO 00/11208 A1 | 3/2000 |
| WO | WO 02/061661 A2 | 8/2002 |

OTHER PUBLICATIONS

David N. Perkins, Darryl J.C. Papin, David M. Creasy, and John S. Cottrell, "Probability-based protein identification by searching sequence databases using mass spectrometry data," *Electrophoresis*, vol. 20 (1999), pp. 3551-3567.

Jurgen Kast; Marc Gentzel; Matthias Wilm; and Keith Richardson, "Noise Filtering Techniques for Electrospray Quadrupole Time of Flight Mass Spectra," *Journal of American Society for Mass Spectrometry*, vol. 14, (2003), pp. 766-776.

Thomas Kreitler, et al., "Frequency Analysis of MALDI-TOF Spectra: Noise Filtering and Signal Detection," Internet article [online] 2003, retrieved from the Internet at: <URL: www.molgen.mpg.de/mass-spec/index/asms/JG_abstract_2299.pdf> [retrieved on Jan. 9, 2004], 2 pgs.

PCT Invitation to Pay Additional Fees for PCT International Appln. No. US01/49491 mailed Oct. 20, 2003 (5 pgs.).

PCT International Search Report for PCT International Appln. No. US01/49491, mailed Jan. 2004 (9 pgs.).

U.S. Appl. No. 60/242,165, filed Oct. 2000, Schneider et al.
U.S. Appl. No. 60/242,398, filed Oct. 2000, Schneider et al.
U.S. Appl. No. 60/415,481, filed Oct. 2002, Schneider et al.
U.S. Appl. No. 60/551,937, filed Apr. 2000, Schneider et al.

Aebersold, R. et al., "Design, synthesis, and characterization of a protein sequencing reagent yielding amino acid derivatives with enhanced detectability by mass spectrometry", *Protein Science* (1992) pp. 494-503, Cambridge University Press.

Biemann, K., "Sequencing of peptides by tandem mass spectrometry and high-energy collision-induced dissociation", *Methods Enzymol.* 193:455-79 (1990).

Bures, E.J. et al., "Synthesis of the protein-sequencing reagent 4-(3-Pyridinylmethylaminocarboxypropyl) Phenyl isothiocyanate and characterization of 4-(3-Pyridinylmethylaminocarboxypropyl) phenylthiohydantoins[1]", *Anal. Biochem.* 224:364-72 (1995).

Chakraborty, Ashish et al., "Global internal standard technology for comparative proteomics", Journal of Chromatography A., 2002, 949:173-84.

Clauser, K.R. et al., "Rapid mass spectrometric peptide sequencing and mass matching for characterization of human melanoma proteins isolated by two-dimensional PAGE", *Proc. Natl. Acad. Sci. U.S.A.*, 92:5072-6 (1995).

Gerber, Scott A. et al., "Absolute quantification of proteins and phosphoproteins and phosphoproteins from cell lysates by tandem MS", PNAS 100(12):6940-5, Jun. 10, 2003.

Gygi, Steven P. et al., "Quantitative analysis of complex protein mixtures using isotope-coded affinity tags", Nature Biotechnology 17:994-9, Oct. 1999.

Hall, Michael P. et al., "'Mass defect' tags for biomolecular mass spectrometry", Journal of Mass Spectrometry, 2003, 38:809-16.

Hobba et al., "The insulin-like growth factor (IGF) binding site of bovine insulin-like growth factor binding protein-2 (biGF BP-2) probed by Iodination" J. Biol. Chem. 271(48):30529-36 (Nov. 29, 1996).

Huang, Zhi-Heng et al., "Protein sequencing by matrix-assisted laser desorption ionization-postsource decay-mass spectrometry analysis of the N-Tris(2,4,6-trimethoxyphenyl)phosphine-acetylated tryptic digests", *Anal. Biochem.*, 268:305-17 (1999).

Hughey, Christine A. et al., "Kendrick mass defect spectrum: a compact visual analysis for ultrahigh-resolution broadband mass spectra", Anal. Chem. Oct. 1, 2001, 73(19):4676-81.

Huhmer, Andreas F.R., "Separation and analysis of peptides and proteins", *Anal. Chem.*, 69:29R-57R (1997).

Integrated Publishing, "Nuclear Power Fundamentals", retrieved from the internet at http://www.tpub.com/content/doe/h1019v1/css/h1019v1_45.htm on Jul. 11, 2006, 2 pages.

International Preliminary Examination Report dated Jun. 19, 2003 and International Search Report dated Aug. 20, 2002 from International Application No. PCT/ US01/49951, 10 pages.

Jensen, Ole N. et al., "Sequence patterns produced by incomplete enzymatic digestion or one-step Edman degradation of peptide mixtures as probes for protein databases searches", *Electrophoresis*, 17:938-44 (1996).

Johnson, Richard S. et al., "Collision-induced fragmentation of (M+H)+ ions of peptides. Side chain specific sequence ions", *International Journal of Mass Spectrom and Ion Process*, 86:137-54 (1988).

Li, G. et al., "Improvements on sample handling for rapid mass spectrometric Identification of proteins resolved by 2D gel electrophoresis". Book of Abstracts, 213th ACS National Meeting, San Francisco, 13-17, Anal. 92 (Apr. 1997).

Li, G., "Rapid mass spectrometric identification of proteins from two-dimensional polyacrylamide gels after in gel proteolytic digestion", *Electrophoresis*, 18:391-402 (1997).

Mann, M. et al., "Error-tolerant identification of peptides in sequence databases by peptide sequence tags", *Anal. Chem.*, 66(24):4390-9 (Dec. 15, 1994).

Mirgorodskaya, Olga A. et al., "Quantitation of peptides and proteins by matrix-assisted laser desorption/ionization mass spectrometry using 18 O-labeled internal standards", Rapid Communication in Mass Spectometry, 2000, 14:1226-32.

Miyagi, Masaru et al., "A novel derivatization method with 5-Bromonicotinic acid N-Hydroxysuccinimide for determination of the amino acid sequences of peptides", Rapid Communications in Mass Spectrometry, 1998, 12:603-8.

Murphy, Constance M., "Recognition of the carboxy-terminal peptide in cyanogen bromide digests of proteins", *Anal. Chem.*, 67:1644-5 (1995).

Ong, Shao-En et al., "Stable isotope labeling by amino acids in cell culture, SILAC, as a simple and accurate approach to expression protemics", *Molecular & Cellular Proteomics 1.5*, 2002, pp. 376-386.

Rose, K. et al., "C-Terminal peptide identification by fast atom bombardment mass spectrometry", *Biochem. J.*, 250:253-9 (1988).

Schnolzer, Martina, "Protease-catalyzed incorporation of $^{18}$O into peptide fragments and its application for protein sequencing by electrospray and matrix-assisted laser desorption/ionization mass spectrometry", *Electrophoresis*, 17:945-53 (1996).

Scholz, Eva et al., "Characterization of a basement membrane protein (BM180) using capillary electrophoresis", *J. Capillary Electrophor.*, 4:287-92 (1997).

Shevchenko, Andrej et al., "Linking genome and proteome by mass spectrometry: large-scale identification of yeast proteins from two dimensional gels", *Proc. Natl. Acad. Sci. U.S.A.*, 93:14440-5 (1996).

Stults, John T. et al., "Simplification of high-energy collision spectra of peptides by amino-terminal derivatization", *Anal. Chem.*, 65:1702-8 (1993).

Supplementary European Search Report from Application No. EP01270150 dated Oct. 5, 2009, 4 pages.

Thomsson, Kristina A. et al., "Sequencing of sulfated oligosaccharides from mucins by liquid chromatography and electrospray ionization tandem mass spectrometry" Anal. Chem. 72(19):4543-9 (Oct. 1, 2000).

Tomer, Kenneth B. et al., "Location of double bond position in unsaturated fatty acids by negative ion MS/MS", *J. Am. Chem. Soc.*, 105:5487-8 (1983).

Vath, James E. et al., "Method for the derivatization of organic compounds at the sub-nanomole level with reagent vapor", *Fresenius Z Anal. Chem.*, 331:248-52 (1988).

Wagner, D.S. et al., "Derivatization of peptides to enhance ionization effiency and control fragmentation during analysis by fast atom bombardment tandem mass spectrometry", *Biol. Mass Spectrom.*, 20:419-425 (1991).

Wilkins et al. Protein Identification with N and C-terminal sequence tags in proteome projects:, *J. Mol. boil.*, 278:599-608 (1998).

Wilkins et al., Protein identification with sequence tags:, *Current Biology*, 6(12):1543-4 (1996).

Wilkins et al., "Rapid protein identification using N-terminal "sequence tag" and amino acid analysis", *Biochemical and Biophysical Research Communicaitons*, 221:609-3 (1996) Article No. 0643.

Yates, John R., "Peptide mass maps: a highly informative approach to protein identification", *Anal. Biochem.*, 214:397-408 (1993).

Zaia, Joseph et al., "Comparison of charged derivatives for high energy collision-induced dissociation tandem mass spectrometry", *J. Am. Soc. Mass Spectrom.*, 6:428-36 (1995).

Zaia, Joseph, "Charged derivatives for peptide sequencing using a magnetic sector instrument", *Methods Mol. Biol.*, 61:29-41 (1996).

International Preliminary Examination Report from PCT/US01/49491 dated Mar. 1, 2005, 5 pages.

Yates, John R. III, "Mass spectrometry and the age of the proteome", Journal of Mass Spectrometry 33:1-19, 1998.

FIG. 14B

FROM FIG. 14A

359

IN ONE EXAMPLE, DETERMINE Pi (A FIRST RANKING) EACH PARTICULUAR POSSIBLE SEQUENCE j AT A GIVEN AA LENGTH i:

$$Pi = \text{NORMAL DISTRIBUTION} \left[ \frac{c_{i,j}^M - \bar{c}_i}{\sigma_i} \right]$$

WHERE:

$$\bar{c}_i = \left( \sum_{j=1}^{19^i} c_{i,j}^M \right) \bigg/ 19^i$$

AND $$\sigma_i = \sqrt{\frac{\sum_{j=1}^{19^i} \left(c_{i,j}^M\right)^2 - \left(\bar{c}_i\right)^2}{19^i}}{(19^i - 1)}}$$

DETERMINE CUMULATIVE RANKING FOR A GIVEN SEQUENCE OVER DIFFERENT SEQUENCE LENGTHS —e.g. CALCULATE $$R_{j,n} = \prod_{i=1}^{n} P_i \quad \text{OR} \quad = \sum_{i=1}^{n} P_i$$

e.g. $P\left[c_{2,j=A-A}^M\right] + P\left[c_{3,j=A-A-X}^M\right] = $ CUMULATIVE RANKING

361

SELECT SEQUENCE WITH HIGHEST CUMULATIVE RANKING

LABEL 1

$c_{i,j,k,l} = LOOKUP \left[(m/z)_{i,j,k,l}\right]_{LABEL\ 1}$ —1101

1103
$C_{i,j} = \sum_{k=min\ CHARGE\ STATES}^{MAX\ CHARGE\ STATES} \sum_{l=1}^{MAX\ ION\ TYPES} c_{i,j,k,l}$ 1107
$\sigma_i = \sqrt{\dfrac{\sum_{j=1}^{19^i} C_{i,j}^2 - \dfrac{\left(\sum_{j=1}^{19^i} C_{i,j}\right)}{19^i}}{(19^i - 1)}}$ 1105
$\overline{C}_i = \dfrac{\sum_{j=1}^{19^i} C_{i,j}}{19^i}$ 1109
$P_i = NORMDIST\left[\dfrac{(C_{i,j} - \overline{C}_{i,j})}{\sigma_i}\right]$ 1111
$R_{j,n} = \prod_{i=1}^{n} P_{i,j}\ OR\ \sum_{i=1}^{n} P_{i,j}$

LABEL 2

$d_{i,j,k,l} = LOOKUP\left[(m/z)_{i,j,k,l}\right]_{LABEL\ 2}$ —1121

1123
$D_{i,j} = \sum_{k=min\ CHARGE\ STATES}^{MAX\ CHARGE\ STATES} \sum_{l=1}^{MAX\ ION\ TYPES} d_{i,j,k,l}$ 1127
$\sigma_i^{label2} = \sqrt{\dfrac{\sum_{j=1}^{19^i} D_{i,j}^2 - \dfrac{\left(\sum_{j=1}^{19^i} D_{i,j}\right)}{19^i}}{(19^i - 1)}}$ 1125
$\overline{D}_i = \dfrac{\sum_{j=1}^{19^i} D_{i,j}}{19^i}$ 1129
$q_i = NORMDIST\left[\dfrac{(D_{i,j} - \overline{D}_{i,j})}{\sigma_i^{label2}}\right]$ 1131
$R_{j,n} = \prod_{i=1}^{n} q_i\ OR\ \sum_{i=1}^{n} q_i$ 1135
$R_{j,n} = \prod_{i=1}^{n} (p_i q_i)\ OR\ \sum_{i=1}^{n} (p_i q_i)$

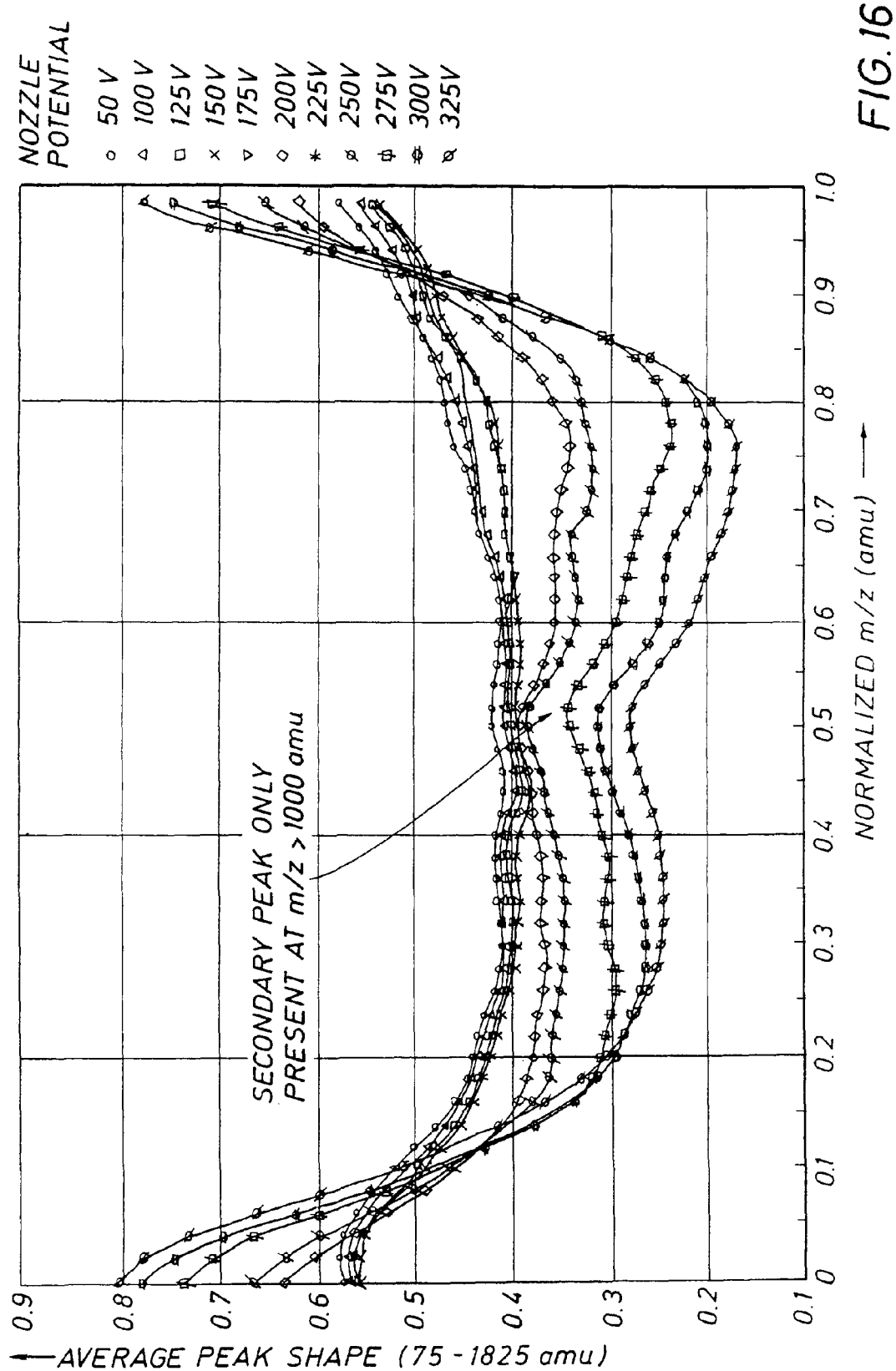

METHODS FOR DERIVING A CUMULATIVE RANKING

CROSS-REFERENCES TO RELATED APPLICATIONS

This application is a continuation of U.S. patent application Ser. No. 10/033,303, filed Oct. 19, 2001, which is related to copending U.S. Patent Application No. 60/242,165, filed Oct. 19, 2000 entitled "Methods for Determining Protein and Peptide Terminal Sequences," U.S. patent application Ser. No. 09/513,395, filed Feb. 25, 2000, entitled "Methods for Protein Sequencing," and copending U.S. patent application Ser. No. 09/513,907, filed Feb. 25, 2000, entitled "Polypeptide Fingerprinting Methods and Bioinformatics Database System," and to commonly assigned co-pending U.S. patent application Ser. No. 60/242,398, filed on Oct. 19, 2000, entitled "Methods for Determining Protein and Peptide Terminal Sequences." These applications are incorporated by reference in their entirety for all purposes. More specifically, the Computer Program Listing Appendix provided in U.S. patent application Ser. No. 10/033,303 is herein incorporated by reference in its entirety for all purposes related to the presently disclosed invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

COMPUTER PROGRAM LISTING APPENDIX

U.S. patent application Ser. No. 10/033,303 contains an appendix consisting of a computer program listing of more than ten pages. The computer listing was provided on a single CD-R and was accompanied by a duplicate copy, two CD-R in total. The material contained on the CD-R was specifically incorporated by reference in U.S. patent application Ser. No. 10/033,303, and is herein specifically incorporated by reference. The material on the compact disk includes the following files: BatComputerPeriodDeconvolveMF cpp; BatComputePeriodDeconvolveMF h; Bfactor cpp; Bfactor h; CDialogMainMF cpp; CDialogMainMF h; CElementsMF cpp; CElementsMF h; CErrorLogMF cpp; CErrorLogMF h; ComputeDriftMF cpp; ComputeDriftMF h; CResiduesMF cpp; CResiduesMF h; CSeqInputMF cpp; CSeqInputMF h; CSeqOutputMF cpp; CSeqOutputMF h; CSequenceMF cpp; CSequenceMF h; CSpectroConversionMF cpp; CSpectroConversionMF h; CSpectroDataMF cpp; CSpectroDataMF h; CSpectroSubtractionMF cpp; CSpectroSubtractionMF h; CTabbedSpectroDataMF cpp; CTabbedSpectroDataMF h; CTextFileMF cpp; CTextFileMF h; CUserInputMF cpp; CUserinputMF h; CUserMessagesMF cpp; CUserMessagesMF h; DeconvolveMF cpp; DeconvolveMF h; FourierMF cpp; SequencerMF cpp; SequencerMF h; and TDSpectroDataCommonMF h.

BACKGROUND OF THE INVENTION

Many molecules are fragmented by chemical, electrical (electron beam or field induced collisions with neutral gas molecules), or optical (excimer lasers) means in mass spectrometers so that the masses of the resulting labeled ion fragments can be used to identify or reconstruct the original molecule. In other instances molecules may coelute from separation processes to be further distinguished by mass spectrometry. In some instances a label is attached to the parent molecule, or specific molecules in a mixture, to assist in the identification of the resulting labeled ions or ion fragments from other chemical noise in the mass spectrum. Typically, this label consists of elements, or isotopes of elements, already contained in the parent molecule. In this way two or more peaks of predetermined relative abundances can be found in the mass spectrum and used to confirm the identify of labeled fragments. However, when the label contains elements (or isotopes of these elements) already contained in the parent molecule or in other ions generated from or otherwise contaminating the sample matrix, one or more of the labeled fragment peaks may overlap with other unlabeled ion peaks in the spectrum, confounding identification of the labeled ions. Historically, techniques such as Edman degradation have been extensively used for protein sequencing. However, sequencing by collision-induced dissociation mass spectrometry (MS) methods (MS/MS sequencing) has rapidly evolved and has proved to be faster and require less protein than Edman techniques.

MS sequencing is accomplished either by using higher voltages in the ionization zone of the MS to randomly fragment a single peptide isolated from a protein digest, or more typically by tandem MS using collision-induced dissociation in the ion trap. Several techniques can be used to select the peptide fragment used for MS/MS sequencing, including accumulation of the parent peptide fragment ion in the quadrapole MS unit, capillary electrophoretic separation coupled to ES-TOF MS detection, or other liquid chromatographic separations. The amino acid sequence of the peptide is deduced from the molecular weight differences observed in the resulting MS fragmentation pattern of the peptide using the published masses associated with individual amino acid residues in the MS, and has been codified into a semi-autonomous peptide sequencing algorithm.

For example, in the mass spectrum of a 1425.7 Da peptide (HSDAVFITDNYR) (SEQ ID NO: 25 isolated in an MS/MS experiment acquired in positive ion mode, the difference between the full peptide 1425.7 Da and the next largest mass fragment (y11, 1288.7 Da) is 137 Da. This corresponds to the expected mass of an N-terminal histidine residue that is cleaved at the amide bond. For this peptide, complete sequencing is possible as a result of the generation of high-abundance fragment ions that correspond to cleavage of the peptide at almost every residue along the peptide backbone. In the above-recited peptide sequence, the generation of an essentially complete set of positively-charged fragment ions that includes either end of the peptide is a result of the basicity of both the N- and C-terminal residues. When a basic residue is located at the N-terminus and/or C-terminus, most of the ions produced in the collision induced dissociation (CID) spectrum will contain that residue since positive charge is generally localized at the basic site. The presence of a basic residue typically simplifies the resulting spectrum, since a basic site directs the fragmentation into a limited series of specific daughter ions. Peptides that lack basic residues tend to fragment into a more complex mixture of fragment ions that makes sequence determination more difficult.

Nucleic acid sequencing has historically been conducted through the synthesis of nucleic acid fragments containing random numbers of bases copied from a parent nucleic acid sequence, such as the methods defined by Sanger and Colson (Proc. Natl. Acad. Sci. (USA), 74:5463-5467 (1977)) and Maxam and Gilbert (Methods in Enzymology, 65:499-560 (1980)). A variation on the method described by Sanger and Colson uses an incomplete polymerase chain reaction (PCR) method to synthesize the ladder of DNA fragments (Nakamaye et al., Nuc. Acids Res., 16(21):9947-9959 (1988)). Mass spectrometric methods have been developed for more rapid and multiplexed separation and identification of the DNA ladders, as described by Koster (U.S. Pat. No. 5,691,141 and U.S. Pat. No. 6,194,144), Monforte et al. (U.S. Pat. No. 5,700,642), and Butler, et al (U.S. Pat. No. 6,090,558). In these methods the nucleic acid fragments are introduced simultaneously into the mass spectrometer and the sequence or number of "short tandem repeats" are deduced from the mass differences between individual elements of the synthesized mass fragment ladder. As described by Koster (U.S. Pat. No. 6,194,144), it is both possible and desirable to sequence several nucleic acids simultaneously in parallel by differentially labeling the nucleic acid fragments synthesized from unique nucleic acid parent templates with different tags of sufficiently unique masses. Even using labels of unique mass, care must be given to avoid subfragmentation of the elements of the sequence ladder during ionization or ion transmission in the mass spectrometer, and to purify the nucleic acid fragments from other extraneous nucleic acids and confounding matrix contaminants so that an unambiguous sequence can be obtained from the resulting mass spectrum. These references are incorporated by reference in their entirety for all purposes.

Polysaccharide sequencing methods, utilizing mass tagging methods in the mass spectrometer have also been described by Rademacher et al. (U.S. Pat. No. 5,100,778) and Parekh and Prime (U.S. Pat. No. 5,667,984). In these methods a unique mass tag is attached to a purified polysaccharide sample, which is subsequently divided into aliquots that are subjected to different regimes of enzymatic and/or chemilytic cleavage to produce a series of labeled oligosaccharide fragments derived from the polysaccharide parent. These fragments are simultaneously introduced into a mass spectrometer and the sequence of sugars contained in the parent polysaccharide determined from the resulting mass ladder generated in the mass spectrum from the random labeled oligosaccharide fragments. It is recognized that increased throughput may be obtained by processing several different samples simultaneously in parallel through the use of different mass tags attached to each unique purified polysaccharide parent sample. Again, care must be taken with the oligosaccharide samples to avoid subfragmentation in the mass spectrum and to purify the labeled fragments from unlabeled oligosaccharide contaminants to avoid sequencing ambiguities. These references are incorporated by reference in their entirety for all purposes.

Identification of the fatty acid composition and placement in lipids can be an important indicator of the state of a cell. For example, Oliver and Stringer (Appl. Environ. Microbiol., 4:461 (1984)) and Hood et al. (Appl. Environ. Microbiol., 52:788 (1986)) both report a 99.8% loss of phospholipids on starvation of *Vibrio* sp. Cronan (J. Bacteriol., 95:2054 (1968)) found 50% of the phosphotidyldglycerol content of Escherchia coli K-12 were converted to cardiolipin within 2 hours of the onset of phosphate starvation and that the fatty acid composition also shifted significantly. The lipid composition of the cell membrane is also of medical interest because of its potential roles in drug and metabolite uptake, anchoring transmembrane proteins, virial recognition of cell surfaces, tumor proliferation and metastasis, and arterial disease.

Similar mass tag approaches have been described for the identification of individual components of combinatorially-synthesized chemical libraries by Sugarman et al. (U.S. Pat. No. 6,056,926) and Brenner et al. (Proc. Natl. Acad. Sci. (USA), 89:5381-5383 (1992)), where a unique mass tag label is concurrently synthesized with the chemical compound of interest on a solid surface and later used to identify the various processing steps applied to the solid surface. This mass label can be identified after cleavage from the solid surface by mass spectrometry. The limitation on the size of the library that can be produced via combinatorial approaches is the number of unique mass labels that can be generated and the ability to discriminate these labels from the compounds of interest. These references are incorporated by reference in their entirety for all purposes.

Ness et al. (U.S. Pat. No. 6,027,890), Schmidt et al. (WO99/32501), and Aebersold et al. (WO00/11208) all describe methods for differentially labeling biological molecules obtained from different sources with a different mass tag for each source. The samples may then be combined, post labeling, and processed together through separation reactions or affinity enrichment, such that individual compounds from each sample are assured to be treated identically in the mixture. The relative concentrations of individual differentially-labeled biological compounds are then determined by the relative abundances of the individual mass tags in the mass spectrum. Limitations on these methods are that the mass labels employed must behave virtually identically with respect to any processing of the sample mixture and ionization and transport of the resulting ions in the mass spectrometer. For this reason, labels are typically chosen that are chemical analogs (e.g., stable isotope analogs or are simple derivatives of one another). A limitation of these methods is the number of samples that can be commingled for a single parallel analysis, which is limited by the number of mass tag derivatives that can be synthesized with nearly identical separation behaviors and ionization and transmission efficiencies. Another limitation of these methods is the ability to distinguish the mass labeled molecules or cleaved labels from unlabeled biomolecules and matrix contaminants that may also be present in the sample introduced into the mass spectrometer. This latter limitation often means that the labeled sample must be extensively purified prior to mass spectral analysis and that subfragmentation of the labeled molecules in the mass spectrometer must be avoided.

Schmidt et al. (WO 99/32501 (Jul. 1, 1999)) describe the use of fluorine (F) in place of hydrogen as a distinguishable mass defect element in cleavable mass labels. The basis of this claim is the 0.009422 amu monoisotopic mass difference between these two elements. However, this claim has several critical limitations. First, this is a very small mass difference, which can only be resolved with very high mass resolution mass spectrometers and at the lowest mass ranges in these mass spectrometers. The resolution of mass spectrometers depends on the mass range and is normally quoted in parts per million. For example, typical time-of-flight detectors common in the industry have a mass resolution of about 10 amu at a mass of 1 million amu (10 ppm). Therefore, as shown in Figure AA, the comparatively small mass difference between F and H is impossible to resolve above a mass of about 940 amu, and from a practical perspective at an even lower m/z.

Schmidt et al. further note that the mass defect of perfluorinated hydrocarbons can be distinguished from simple hydrocarbons. For example, the monoisotopic mass of a polyfluorinated aryl tag with a maximum stoichiometry of $C_6F_5$ is exactly 166.992015 amu. The monoisotopic mass of the closest hydrocarbon is 167.179975, which corresponds to the a stoichiometry of C12H23 and an easily resolvable mass difference of about 1125 ppm. The mass of the minimum polyfluorinated aliphatic tag is 68.995209 amu, which corresponds to a $CF_3$ stoichiometry. The closest monoisotopic hydrocarbon mass to this is 69.070425, corresponding to a C5H9 stoichiometry and a difference of 1089 ppm.

However, for organic molecules that include heteroatoms, such as N and O, which are typical in biological molecules, the mass defect of fluorine is not as easily distinguished. For example, any molecule that contains a stoichiometry of C3HO2 will have a monoisotopic mass that is only 35 ppm different from that of CF3, making it nearly indistinguishable even at 69 amu. Similarly, any molecule that contains a monoisotopic stoichiometry of C7H3O5 is only 36 ppm different from C6F5 at 167 amu.

When the stable isotopes of C, N, and O are included in the calculations, the mass defect of C6F5 reduces to an indistinguishable 1.4 ppm when compared to a molecule that contains a stoichiometry of [12C]4[13C]2[15N]3[16O]2. Similarly, the mass defect for CF3 reduces to an mere 29 ppm compared to a molecule that contains [12C]2[13C][16O]2 stoichiometry. As the overall mass of the tag increases beyond 200 amu, the mass defect introduced even with multiple fluorines rapidly becomes indistinguishable among the defects of the other heteroatoms and stable isotopes. Adding even more fluorines to the molecule is often not practical due to solubility constraints.

The general problem of deconvolving individual peaks of interest from complex mass spectral data has been previously described for complex mixtures of small molecules (see Mallard, G. W. and J. Reed, "Automated Mass Spectral Deconvolution & Identification System, AMDIS-User Guide" (US Department of Commerce, Gaithersburg, Md., 1997) and Stein, S. E., "An integrated method for spectrum extraction and compound identification from GC/MS Data," J Am Soc Mass Spect, 10:770-781 (1999)), particularly when coupled to time resolved separation methods (e.g., GC/MS and LC/MS). However, these techniques have not been applied to biopolymer (e.g., protein, nucleic acid, and polysaccharide) fragmentation spectra for the purpose of sequence determination. In fact, these methods typically attempt to identify the intact chemical species and generally seek to avoid fragmenting conditions in the ms. Nor, have they been coupled to the identification of labeled biomolecular ions containing unique mass tags.

Extending the concept of simplifying the CID spectrum of a peptide by including a charge concentrating moiety on either terminus of the peptide, others have demonstrated that attaching a hard positive charge to the N-terminus directs the production of a complete series of N-terminal fragment ions from a parent peptide in CID experiments regardless of the presence or absence of a basic residue at the N-terminus. Theoretically, all fragment ions are produced by charge-remote fragmentation that is directed by the fixed-charged group.

Peptides have been labeled with several classes of fixed-charge groups, including dimethylalkylammonium, substituted pyridinium, quaternary phosphonium, and sulfonium derivatives. Characteristics of useful labels include, ease of synthesis, increase in ionization efficiency of labeled peptides, and formation from a labeled peptide of a specific fragment ion series with minimal unfavorable label fragmentation. Zaia reported that the labels satisfying these criteria include those of the dimethylalkylammonium class and quaternary phosphonium derivatives. Moreover, it has been reported that substituted pyridinium derivatives are useful in high-energy CID.

Despite some progress in analytical methodology, protein identification remains a major bottleneck in field of proteomics. For example, it can require up to 18 hours to generate a protein sequence tag of sufficient length to allow the identification of a single purified protein from its predicted genomic sequence. Moreover, although unambiguous protein identification can be attained by generating a protein sequence tag (PST), limitations on the ionization efficiency of larger peptides and proteins restrict the intrinsic detection sensitivity of MS techniques and inhibit the use of MS for the identification of low abundance proteins. Furthermore, limitations on the mass accuracy of time of flight (TOF) detectors can also constrain the usefulness of presently utilized methods of MS/MS sequencing, requiring that proteins be digested by proteolytic and/or chemolytic means into more manageable peptides prior to sequencing. In addition, previously described MS ladder sequencing algorithms fail on proteins because the abundance of peptide fragments generated during CID of such large molecules and inability to identify an appropriate parent ion to initiate the sequence effectively obscure the mass ladder.

Two basic strategies have been proposed for the MS identification of proteins after their separation from a protein mixture: 1) mass profile fingerprinting ('MS fingerprinting'); and 2) sequencing of one or more peptide domains by MS/MS ('MS/MS sequencing'). MS fingerprinting is achieved by accurately measuring the masses of several peptides generated by a proteolytic digest of the intact protein and searching a database for a known protein with that peptide mass fingerprint. MS/MS sequencing involves actual determination of one or more PSTs of the protein by generation of sequence-specific fragmentation ions in the quadrapole of an MS/MS instrument.

Clauser et al. have suggested that proteins can only be unambiguously identified through the determination of PSTs that allow reference to the theoretical sequences determined from genomic databases. Li et al. appear to have proven this assertion by finding that the reliable identification of individual proteins by MS fingerprinting degenerated as the size of the comparative theoretical peptide mass database increased. Li et al. also reported that they were only able to obtain peptide maps for the highest abundance proteins in the gel because of sensitivity limitations of the MS, even though their matrix assisted laser desorption MALDI methodology was demonstrated to improve the detection sensitivity over previously reported methods. Clearly, rapid and cost effective protein sequencing techniques will improve the speed and lower the cost of proteomics research. Similarly, as described by Koster, the preparation and purification of nucleic acids prior to sequencing, even by mass spectrometers, increases the time and cost of nucleic acid sequencing. Improving the discrimination ability of the mass spectrometer, such that multiple protein, nucleic acid, polysaccharide or other sequences can be determined in parallel or specific ions can be better differentiated from unlabeled organic material, has considerable utility over existing methods.

SUMMARY OF THE INVENTION

Methods and apparatuses for deriving the sequence of a oligomer, such as a protein, nucleic acid, lipid or polysaccharide. According to one exemplary method, a predetermined set of mass/charge values for amino acid sequences is stored. An abundance value from mass spectrum data for each mass/charge value in the predetermined set is determined to produce a plurality of abundance values. A first ranking, based on the plurality of abundance values, is calculated for each sequence of a set of amino acid sequences having a first number of amino acids. A second ranking, based on the plurality of abundance values, for each sequence of a set of amino acid sequences having a second number of amino acids is calculated. A cumulative ranking, based on the first ranking and the second ranking, is calculated for each sequence of a set of amino acid sequences having at least the second number of amino acids. Other methods for determining sequences are also described. A method for filtering mass spectrum data to remove periodic chemical noise is also described. One exemplary method for filtering noise includes determining a substantially periodic block of noise in mass spectrum data generated from accelerating fragments of a protein to a detector, and filtering the substantially periodic block of noise from the mass spectrum data. Apparatuses for performing these methods and other methods are also described.

Embodiments of the present invention overcome the limitations of oligomer length, particularly for both MS and MS/MS sequencing of proteins. Because certain embodiments of methods of the invention preferably eliminate the need for proteolytic or chemolytic digestion of the protein, these methods provide protein sequencing times that are significantly reduced from the times obtainable using prior methods. Moreover, because the proteins being sequenced are highly fragmented using the present methods, the ionization efficiency and the volatility of the resulting fragments are higher than those of the parent protein, thus leading to a detection sensitivity that is improved over prior methods.

Thus, in one aspect, the present invention provides a method for sequencing a terminal portion of a protein, comprising:

(a) contacting a protein with a C-terminus or N-terminus labeling moiety to covalently attach a label to the C- or N-terminus of the protein and form a labeled protein; and (b) analyzing the labeled protein using a mass spectrometric fragmentation method, and (c) determining the sequence of at least the two C-terminus or two N-terminus residues by algorithmic deconvolution of the labeled terminal mass ladder from other non-terminal sequence fragments in the resulting mass spectrum.

In one group of embodiments, the method further comprises:

(d) identifying the protein by using the sequence of the at least two C-terminus or two N-terminus residues to search predicted protein sequences from a database of gene sequence data.

In another aspect, the present invention provides a method for sequencing a portion of a protein in a protein mixture, the method comprising:

(a) contacting the protein mixture with a C-terminus or N-terminus labeling moiety to covalently attach a label to the C- or N-terminus of the protein and form a labeled protein mixture;

(b) separating individual labeled proteins in the labeled protein mixture; and (c) analyzing the labeled proteins from step (b) by a mass spectrometric fragmentation method, and (d) determining the sequence of at least the two C-terminus or two N-terminus residues by algorithmic deconvolution of the labeled terminal mass ladder from other non-terminal sequence fragments in the resulting mass spectrum.

In one group of embodiments, the method further comprises:

(a) identifying the protein by using the sequence 6f at least two C-terminus or two N-terminus residues in combination with a separation coordinate of the labeled protein and the protein terminus location of the sequence to search predicted protein sequences from a database of gene sequence data. In another aspect, the present invention provides a method for sequencing a terminal portion of an oligomer or polymer, comprising: (a) contacting said oligomer with a labeling moiety to covalently attach a label to the terminus of the oligomer and form a labeled oligomer, the labeling moiety having a mass different from any of the constitutive monomers comprising the oligomer, (b) fragmenting the labeled oligomer using an enzymatic, chemolytic or mass spectrometric fragmentation method to produce labeled oligomer fragments; and (c) determining the sequence of at least the two terminal monomers adjacent to the label by algorithmic sequencing of the labeled terminal mass ladder from other non-terminal sequence fragments in the resulting mass spectrum.

In embodiments of the methods above, the use of a robust algorithm for terminally-labeled protein sequencing by in-source fragmentation provides advantages over conventional MS/MS sequencing algorithm approaches. One particular advantage of certain embodiments is the ability to sequence full proteins and nucleic acids without the need for prior digestion into small peptide or nucleic acid fragments. Another advantage of certain embodiments is that the method is self-starting and does not require any knowledge of the parent ion size or composition to determine the sequence. Another advantage of certain embodiments is that the method can be highly automated. Another advantage of certain embodiments is that fewer sequence ambiguities result due to the improved absolute mass accuracy gained by working at the low end of the mass spectrum. Another advantage of certain embodiments is that better ionization efficiency and corresponding detection sensitivity result from using more energetic ionization conditions and the introduction of a hard or ionizable charge on the fragments through the addition of the label. Yet another advantage of introducing a charge through the label (as in certain embodiments) is the ability to determine partial protein sequences from regions of a protein that may not contain ionizable amino acid residues.

Finally, this method provides in certain embodiments a contiguous protein sequence tag (PST) that can be used both for unambiguous protein identification or to generate a nucleic acid probe, based on an N- or C-terminal protein sequence, that may be useful for isolating the corresponding cDNA from native cell or tissue samples.

BRIEF DESCRIPTION OF THE DRAWINGS

FIGS. 14A and 14B show a particular computational method according to one embodiment of the present invention for sequencing a terminal portion of a protein.

FIG. 15 shows a method according to one embodiment of the present invention which uses two labels for the same protein in order to sequence the protein.

FIGS. 16 and 17 illustrate, respectively, an average filter kernel and a scaling factor optimization graph.

DETAILED DESCRIPTION OF THE INVENTION

Definitions

Figure 1:
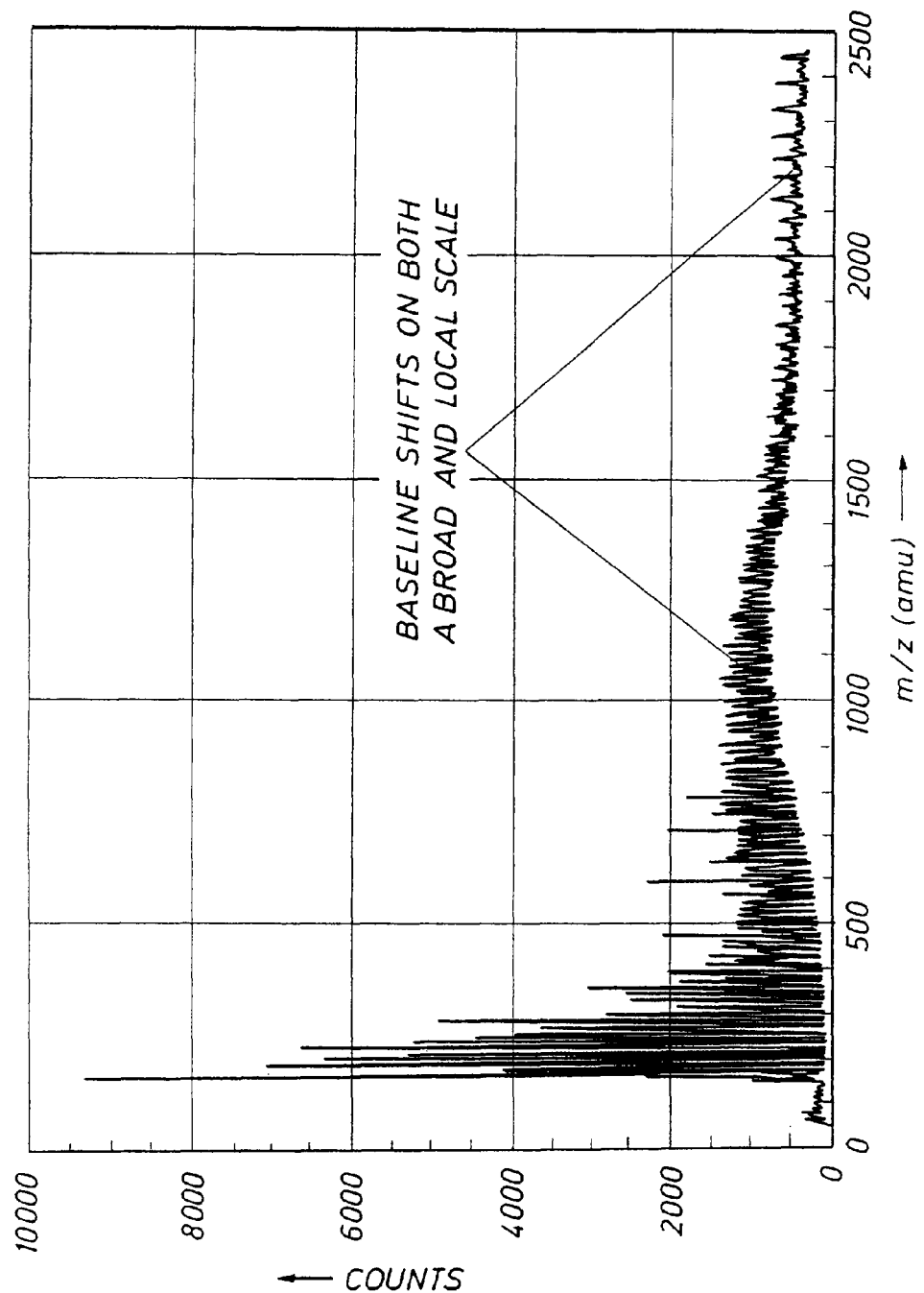
FIG. 1 shows an example of a typical mass spectrum data.

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and protein chemistry described below are those well known and commonly employed in the art. Standard techniques are used for peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., and Methods in Enzymology, Biemann, ed. 193:295-305, 351-360, and 455-479 (1993) which are incorporated herein by reference), which are provided throughout this document. The nomenclature used herein and the procedures in mathematical and statistical analysis, analytical chemistry, and organic synthesis described below are those known and employed in the art. Standard techniques, or modifications thereof, are used for chemical syntheses and chemical analyses.

As used herein, the term "oligomer" refers to any polymer of residues wherein the residues are similar, though typically not identical. Generally, an oligomer is meant to include naturally-occurring polymers such as proteins, oligonucleotides, nucleic acids, oligosaccharides, polysaccharides, lipids, and the like. Oligomer may also refer to free radical, condensation anionic or cationic polymers of synthetic origin, which include, but are not limited to acrylates, methacrylates, nylons, polyesters, polyimides, nitrile rubbers, polyolefins, and block or random copolymers of different monomers in these classes of synthetic polymers. The oligomer that is subject to the analytical methods described herein will have a number of residues that are typical of their naturally occurring number. For example, and oligomer that is an oligonucleotide may have hundreds and even thousands of residues. Similarly, a protein will generally have one hundred or more residues (though the sequencing of smaller fragments, e.g. peptides is also useful). An oligosaccharide will typically have from 3 to 100 sugar residues. A lipid will normally have 2 or 3 fatty acid residues.

As used herein, the terms protein, peptide and polypeptide refer to a polymer of amino acid residues. The terms also apply to amino acid polymers in which one or more amino acids are chemical analogues of corresponding naturally-occurring amino acids, including amino acids which are modified by post-translational processes (e.g., glycosylation and phosphorylation).

"Protein", as used herein, means any protein, including, but not limited to peptides, enzymes, glycoprote ins, hormones, receptors, antigens, antibodies, growth factors, etc., without limitation. Presently preferred proteins include those comprised of at least 10 amino acid residues, more preferably at least 25 amino acid residues, yet more preferably at least 35 amino acid residues and still more preferably at least 50 amino acid residues.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, b-alanine, phenylglycine and homoarginine are also included. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Protein sequencing tag," (PST) as used herein, refers to a contiguous series of at least two amino acids representing a partial sequence of a protein. A preferred PST includes a label of the invention or a fragment of a label of the invention or an ionized derivative of a label of the invention.

The term "nuclear binding energy" refers to the mass disparity between the calculated and actual nuclear masses of the elements. It is defined as the mass equivalent (according to the theory of relativity) of the energy needed to separate a nucleus into its constituent isolated nucleons.

The term "mass defect" or "mass defect label" refers to a portion of a label or the entire label that provides a mass sufficient and distinct to be readily identified in the mass spectrum of the sample. Accordingly, the mass defect is typically an element having an atomic number from 17 to 77, other than sulfur or phosphorus. Typically, the most effective mass defect labels for use with typical organic chemicals (even organic chemicals containing group 1 and group 2 heteroatoms), such as biomolecules, incorporate one or more elements having an atomic number of 35 to 63. Examples of the most preferred mass defects are the elements bromine, iodine, europium and yttrium.

The term "deconvolution" broadly defines mathematical procedures and algorithms for recovering information of interest from data that contains both random and periodic noise, or which has been otherwise obscured by the interaction with electronic or physical collection methods.

The term "alkyl" is used herein to refer to a branched or unbranched, saturated or unsaturated, monovalent hydrocarbon radical, generally having from about 1-30 carbons and preferably, from 4-20 carbons and more preferably from 6-18 carbons. When the alkyl group has from 1-6 carbon atoms, it is referred to as a "lower alkyl." Suitable alkyl radicals include, for example, structures containing one or more methylene, methine and/or methyne groups. Branched structures have a branching motif similar to i-propyl, t-butyl, i-butyl, 2-ethylpropyl, etc. As used herein, the term encompasses "substituted alkyls," and "cyclic alkyl."

"Substituted alkyl" refers to alkyl as just described including one or more substituents such as, for example, lower alkyl, aryl, acyl, halogen (i.e., alkylhalos, e.g. $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

The term "aryl" is used herein to refer to an aromatic substituent, which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

The term "arylalkyl" is used herein to refer to a subset of "aryl" in which the aryl group is attached to another group by an alkyl group as defined herein.

"Substituted arylalkyl" defines a subset of "substituted aryl" wherein the substituted aryl group is attached to another group by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "lanthanide series" refers to the elements in the periodic table with atomic numbers between 57 and 71.

The term "hydroxy" is used herein to refer to the group —OH.

The term "amino" is used to designate —NRR', wherein R and R' are independently H, alkyl, aryl or substituted analogues thereof "Amino" encompasses "alkylamino" denoting secondary and tertiary amines and "acylamino" describing the group RC(O)NR'.

The term "alkoxy" is used herein to refer to the —OR group, where R is alkyl, or a substituted analogue thereof. Suitable alkoxy radicals include, for example, methoxy, ethoxy, t-butoxy, etc.

As used herein, the term "aryloxy" denotes aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

As used herein "aryloxyalkyl" defines aromatic groups attached, through an oxygen atom to an alkyl group, as defined herein. The term "aryloxyalkyl" encompasses "substituted aryloxyalkyl" moieties in which the aromatic group is substituted as described for "substituted aryl."

As used herein, the term "mercapto" defines moieties of the general structure —S—R wherein R is H, alkyl, aryl or heterocyclic as described herein.

The term "saturated cyclic hydrocarbon" denotes groups such as the cyclopropyl, cyclobutyl, cyclopentyl, etc., and substituted analogues of these structures. These cyclic hydrocarbons can be single- or multi-ring structures.

The term "unsaturated cyclic hydrocarbon" is used to describe a monovalent non-aromatic group with at least one double bond, such as cyclopentene, cyclohexene, etc. and substituted analogues thereof. These cyclic hydrocarbons can be single- or multi-ring structures.

The term "heteroaryl" as used herein refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to another group.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to another group.

The term "heterocyclic" is used herein to describe a monovalent saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to another group.

The term "chelate" refers to the strongly associative binding of a metallic element or metal ion to a substantially organic molecule through non-covalent means. These are alternately known as organometallic molecules.

General

Embodiments of the invention include a mass spectrometric method for improved discrimination of labeled and unlabeled molecules or fragments of molecules in a mass spectrometer. The methods may be used for sequence determination and for increased combinatorial complexity that can be discriminated in a mass spectrum. The methods may be practiced by labeling a terminus of a molecule or oligomer with a labeling reagent that incorporates a mass defect and discriminating the resulting mass defect labeled molecules form other unlabeled molecules or unlabeled molecule fragments in the mass spectrum.

In certain embodiments, a mass spectrometric method for improved discrimination of labeled and unlabeled molecules or fragments of molecules in the mass spectrometer may be used for oligomer sequence determination. A preferred embodiment is a mass spectrometric method that may be used for protein sequence determination. For example, a N- or C-terminus of a protein may be labeled with a unique mass tag (mass defect label), followed by fragmentation of a labeled protein in either the ionization zone of a mass spectrometer (e.g., in-source fragmentation) or in the collision cell of a MS/MS instrument, and determination of the terminal sequence of a protein by using a mathematical algorithm, as described herein. In another embodiment, labeled oligomers may be synthesized from a parent template or chemilytically or enzymatically digested to form fragments that comprise a sequencing ladder of labeled fragments that are algorithmically identified in the mass spectrum from the differential mass defect of a label. Labeled peptides may be differentiated from unlabeled peptides by their unique mass signatures in the resulting mass spectrum and may be deconvoluted from non-labeled protein fragments and peaks associated with the ionization matrix and contaminating protein or peptides by their relative abundance and/or unique mass signatures. A cumulative ranking system may be used by the algorithm to strengthen the certainty of the sequence determined at successive residues of the mass ladder. In some embodiments, this process is accomplished in less than 1 min for a purified labeled protein, yielding a 500 to 1000-fold more rapid method than current MS/MS protein sequencing techniques. Alternatively, the methods may be used for sequence determination of other oligomers, such as oligosaccharides, oligonucleotides, lipids and the like.

In one embodiment, labeled oligomers, such as proteins, are highly fragmented in the MS by collision induced dissociation (CID). CID can be accomplished in the ionization zone (e.g., in-source) or in a collision cell through high energy impact with non-oligomer gases introduced to the collision zone. Preferred labels lead to increased ionization efficiency and enhanced volatility of the resulting labeled oligomer fragment ions, relative to the parent oligomer, such as a peptide relative to a parent protein, thus improving the overall detection sensitivity. Preferred labels impart a unique mass signature to the fragments to which they are attached. In a particularly preferred embodiment, the unique mass signature may consist of one or more elements incorporated into the label that contain a nuclear binding energy that substantially differs from those of the elements associated with amino acids, peptides, and proteins (e.g., C, H, O, N, and S) or other oligomers, fragments of oligomers and monomers derived from such oligomers, such as saccharides, fatty acids, nucleotides and the like. In another embodiment, a mixture of isotopically distinct versions of a label may be used concurrently with the relative abundance of the resulting isotopic pairs used to deconvolute peaks of interest in the mass spectrum. In another embodiment, label analogs that differ by addition of one or more methyl or methylene units may be used to uniquely distinguish peaks of interest in the mass spectrum. In another embodiment, peaks associated with labeled peptides may be deconvolved from unlabeled peptides by their relative abundance. The sequence of a protein or protein sequence tag is preferably constructed from the low molecular weight end of the mass spectrum, providing advantages over prior methods, such as greater absolute mass accuracy and more facile sequencing, including resolution of Q and K residues, from the resulting labeled peptide fragments.

The selection of an appropriate label for this technique requires consideration of several criteria. First, the label is preferably robust enough to survive the fragmentation conditions of the MS. Second, the label preferably also creates a unique mass/charge (m/z) signature that is distinguishable from any unlabeled oligomer fragments, such as peptides, generated from internal scissions of an oligomer or from other unlabeled organic molecules that may be present in the sample. Third, the label may also carry an ionizable or permanently ionized group to ensure that fragmentation produces high-abundance ions that include even uncharged terminal residues, such as uncharged N- and C-terminal residues of proteins.

In certain embodiments, the methods incorporate a robust algorithm for the identification of mass defect labeled molecules or fragments of molecules and determination of an oligomer sequence, such as a protein sequence, from labeled oligomer fragments in the mass spectrum. This algorithm searches the spectral data for all possible oligomer sequences, such as protein sequences, starting only from the mass of the label, which is known. The algorithm uses both the mass to charge ratio of the labeled oligomer fragments, such as peptides, and the relative abundance of the resulting MS peaks to rank all possible oligomer sequences. A cumulative (forward-looking) ranking is used to eliminate sequences as successive numbers of residues, for example amino acids for protein sequencing, are found in the mass spectrum. In a preferred embodiment, chemical noise is selectively deconvolved from the mass spectrum prior to the application of the sequencing algorithm. Unlike previous sequencing algorithms, the current algorithm is robust because it can be implemented without human intervention either to define a starting or parent ion, or to identify or qualify prospective sequence peaks in the mass spectrum. In another embodiment the highest ranked sequence possibilities can be further qualified by their existence in a database of possible protein sequences predicted from gene sequence data, particularly one limited to the organism from which the protein was obtained. In another embodiment, the highest ranked sequence possibilities can be further qualified by the separation coordinates of the parent protein (e.g., isoelectric point and molecular weight) and/or its amino acid composition. Alternative embodiments may include using databases of other oligomers including, but not limited to nucleic acid, polysaccharide, synthetic oligomers and the like to further qualify a ranked oligomer sequence.

Embodiments of the invention may incorporate one or more elements into the label that have a nuclear binding energy (mass defect) that moves the mass of the label to a unique mass position in the spectrum that no other stoichiometric combination of the other elements may have. In this way, labeled fragments are more easily distinguished from chemical noise and may be detected with more accuracy, when present in lower relative abundances, and when present in more complex sample mixtures. In addition, the method may be used to help identify lower abundance labeled fragments produced by various ionization methods (e.g., d-, and w-ions produced by protein and peptide fragmentation).

The use of mass defects can also be applied to the quantification of the relative abundances of the same molecule obtained from two or more sources in a mass spectrometer (see, for example, WO 00/11208, EP1042345A1, and EP979305A1). Using this particular methodology, a label can be attached to an oligomer that differs from the other labels by the replacement of one element with a stable isotope of that element. The sources may be mixed subsequent to labeling and the relative abundance of molecules or the labels from each source are quantified in the mass spectrum. The different isotopes are used to uniquely differentiate the peaks arising from the same molecule from each source. Modification of this method to incorporate one or more mass defect elements into the label may improve this quantification because the resulting labeled molecules or labels will be displaced from any chemical noise in the resulting mass spectrum.

Embodiments of the invention may be used in conjunction with protein sequencing methods, such as inverted mass ladder sequencing (see, copending application Ser. No. 60/242, 165 and PCT publication WO 00/11208) and other MS protein sequencing, quantification, and identification methods, such as outlined in U.S. Pat. No. 6,027,890, and PCT publications WO 99/32501 and WO 00/11208. The use of mass defect labeling can also be applied to DNA sequencing methods by MS, outlined in U.S. Pat. Nos. 5,700,642, 5,691,141, 6,090,558 and 6,194,144. Still further, the method can be used for determining the sequence of polysaccharides (such as the glycosylation pattern of a protein), outlined in U.S. Pat. Nos. 5,100,778 and 5,667,984.

More broadly, the method may be used to improve the identification (sequence determination) or quantification of any polymer from different sources, whether natural or synthetic, providing that a mass defect label can be covalently attached to the polymer.

The invention may also be used for the structural identification or relative quantification of nonpolymeric chemical species from different sources, providing labels can be covalently attached to these molecules. Examples include: differential (diseased vs. healthy tissues) amino acid analysis; differential nucleotide analysis; differential saccarhaide analysis; differential fatty acid analysis and structure determination of unsaturated and branched fatty acids; lipid analysis and structural determination; and nutrient quality control applications, and combinatorial library tags (as outlined in U.S. Pat. No. 6,056,926).

Turning first to the mass defect labeling of nucleic acids (e.g., DNA or RNA), each of U.S. Pat. Nos. 6,090,558 and 6,194,144 describe how DNA can be sequenced from synthesized fragments incorporating a unique mass label in the primer sequence. In contrast, the present invention provides that labeling is carried out using only labels having a mass defect, to distinguish the labeled fragments from unlabeled fragment and provide a more robust, yet sensitive method. Another advantage of the use of mass defect labels is the increased number of nucleic acids that may be sequenced in parallel. The advantages of mass defect labeling (rather than a more general labeling process) were not disclosed in the earlier work.

Similarly, WO 00/11208, EP1042345A1, EP979305A1, and U.S. Pat. No. 6,027,890, describe the use of unique mass labels for differential analysis and quantification of protein and DNA molecules between different sources. However, each of these references fail to anticipate or identify the advantages of incorporating a mass defect element into the unique mass label.

Turning next to oligosaccharide labeling, EP 698218B1 describes the use of labeled carbohydrates and their use in assays and U.S. Pat. Nos. 5,100,778 and 5,667,984 describe the use of mass labels to determine the oligosaccharide sequence by MS. While the techniques disclosed therein might be applicable to labeling with unique mass tags, the incorporation of a mass defect in the label for the purposes of shifting MS peaks to non-interferring regions of the spectra are not disclosed or appreciated. Thus, application of the mass defect labeling methodology described herein provides methods to identify the sugar sequence of a complex carbohydrate by labeling the carbohydrate as described in the prior art (with suitable modification for the incorporation of a mass defect in the label) or by any other method available to those skilled in the art and identifying the mass defect labeled fragments in the mass spectrometer. The carbohydrate structure can be determined in whole or in part by mass addition from the smallest labeled fragments similar to the DNA and MS/MS protein sequencing methods described above. Again, incorporation of a mass defect element into the label has utility for isolating the labeled fragments from the chemical noise.

Turning next to lipids, the fatty acid composition of a lipid can be determined by labeling the glycerol phosphate backbone with a mass defect containing label and randomly hydrolyzing the fatty acids to form fragments of the parent lipid. The fatty acid composition of the parent lipid can then be determined by mass addition to the labeled glycerol phosphate backbone accounting for every possible fatty acid combination.

In certain embodiments, amino acids, lipids, and nucleotides can be derivatized by methods generally available to those skilled in the art. If isotopically-distinct labels are used for derivatization of molecules obtained or extracted from different samples, then differential quantification analysis may be performed by MS. However, in each instance, the incorporation of a mass defect element into the label may improve the ability to isolate the labeled molecules from other chemical noise in the spectrum and obtain more accurate relative abundance measurements. However, unanticipated in the prior art is the incorporation of different numbers of mass defect elements into the labels to increase the number of samples that can be simultaneously discriminated in the resulting mass spectrum. This methodology can also be applied to improve the isolation and identification of metabolites in biological samples (see, for example, U.S. Ser. No. 09/553,424, filed Apr. 19, 2000 Metomics method), where the mixture of isotopically-enriched metabolites obtained from a source are subsequently derivatized with a label containing a mass defect to facilitate the identification and quantification of the isotopically-enriched metabolite from the non-enriched form.

In addition to sequencing and identification of oligomers, mass defect labeling can be used to probe the structure and function of biologically active macromolecules (e.g., oligomers such as proteins, nucleic acids and oligosaccharides).

Deuterium exchange methodology (see, Andersen, et al., *J. Biol. Chem.* 276(17):14204-11 (2001)) has been used to probe secondary and higher-order protein structure and regions involved in ligand binding. Moieties that are exposed to solvent and are not buried or hidden by bound ligands will exchange hydrogen for deuterium at a much faster rate in the presence of deuterated water. Subsequent proteolysis of the protein and mass spectral analysis of the deuterated and non-deuterated proteolytic fragments can elicit information about which moieties are involved in specific higher-order structural elements or in binding epitopes.

Improved methods are provided herein, in which mass defect elements are used to label an oligomer or other macromolecule, in lieu of deuterium. By using small molecules incorporating elements with mass defects that can target specific reactive groups and analyzing fragmentation patterns of, for example, intact or proteolyzed protein samples, information about structure or function can be obtained by searching for products that are labeled or unlabeled with the mass defect label. This information is obtained more readily and unequivocally by the reduction of chemical noise that the mass defect label provides. Specifically, an active protein can be exposed to a mass defect label such as bromine or iodine gas, which targets protein tyrosine residues. Tyrosine residues are labeled differentially depending on their geometric loci (i.e., surface vs. buried) and their participation in ligand binding. The protein can be fragmented, with or without prior proteolysis, and the tyrosine labeling pattern probed easily in the mass spectrometer by searching for peaks arising from incorporation of bromine or iodine atoms.

In alternative embodiments, an area in which mass defect labels may have a beneficial use is in combinatorial analysis of both small and macro molecules that do not already contain elements with mass defects (which are most biologically derived materials). In this application, a complex mixture of entities (e.g., proteins and peptides, including antibodies and enzymes, polysaccharides, polynucleotides, pharmaceuticals, or catalysts) generated as a combinatorial library can be probed for activity and identified by incorporating tagging elements as described in U.S. Pat. No. 6,056,926. By increasing the number of tags, and using tags that incorporate a mass defect element, a larger combinatorial library can be evaluated. Those entities which have desired binding characteristics will display a shift in mass equal to the mass defect label. Even in a very complex mixture, it is straightforward to identify the shifted peaks as a result of the mass defect.

DESCRIPTION OF THE EMBODIMENTS

In certain embodiments, methods of the invention may be used for sequencing oligomers, in particular a terminal portion of an oligomer. In one aspect, the invention may provide a method for sequencing a portion of a protein, comprising:

(a) contacting a protein with a C-terminus or N-terminus labeling moiety to covalently attach a label to the C- or N-terminus of the protein and form a labeled protein; and (b) analyzing the labeled protein using a mass spectrometric fragmentation method, and (c) determining the sequence of at least the two C-terminus or two N-terminus residues by algorithmic deconvolution of the labeled terminal mass ladder from other non-terminal sequence fragments in the resulting mass spectrum.

In this aspect of the invention the protein may be obtained from essentially any source. Preferably, the protein is isolated and purified to be free of interfering components. The isolated protein can be contacted with a C-terminus or N-terminus labeling moiety to covalently attach a label to the C- or N-terminus of the protein to form a labeled protein, suitable for analysis by mass spectrometric fragmentation methods.

Labeled Oligomers

While the invention is exemplified below with reference to labeled proteins, one of skill in the art will recognize that the labels and labeling methods used are adaptable to the preparation of other labeled oligomers (e.g. oligonucleotides, oligosaccharides, synthetic oligomers, etc.)

Labeled Proteins

The labeling of proteins with various agents in an aqueous or mixed aqueous/organic solvent milieu is known in the art and a wide range of labeling reagents and techniques useful in practicing the present invention are readily available to those of skill in the art. See, for example, Means et al., CHEMICAL MODIFICATION OF PROTEINS, Holden-Day, San Francisco, 1971; Feeney et al., MODIFICATION OF PROTEINS: FOOD, NUTRITIONAL AND PHARMACOLOGICAL ASPECTS, Advances in Chemistry Series, Vol. 198, American Chemical Society, Washington, D.C., 1982; Feeney et al., FOOD PROTEINS: IMPROVEMENT THROUGH CHEMICAL AND ENZYMATIC MODIFICATION, Advances in Chemistry Series, Vol. 160, American Chemical Society, Washington, D.C., 1977; and Hermanson, BIOCONJUGATE TECHNIQUES, Academic Press, San Diego, 1996.

Labeling can be conducted and PSTs determined from either the N- or C-terminal end of the protein. About 59-90% of eukaryotic proteins are N-terminal acetylated and are thus refractory to N-terminus labeling. However, the natural N-acetyl group of such proteins can sometimes be used as a label for purposes of this invention, but only where one or more of the amino acids within 4 residues of the N-terminus is ionizable (e.g., is a lysine, arginine, histidine, aspartic acid, or glutamic acid residue) or can be derivatized to be ionizable (e.g., tyrosine, serine, and cysteine residues). Accordingly, strategies to label either the N- or C-termini are provided to afford the greatest degree of sequencing ability for any given protein. Once a label is selected, a deconvolution algorithm can be modified to search for masses that correspond to any modified residues.

Characteristics of the Fragmentation Spectra

The time to flight mass spectrum (FIG. 1) is basically the number of ions (Counts) that strike a detector plate. The time at which the ions strike the detector plate determines the mass to charge (m/z) ratio of the ion striking the plate. The detector plate is calibrated with known m/z molecules. Generally, the precision of the size range covered by the detector varies as the square root of the m/z value. This means that the absolute mass precision decreases with increasing m/z in the mass spectrometer. Noise in a mass spectrometer is always positive. Therefore, the signal is always greater than or equal to zero in each size bin.

Several features of the mass spectrum of fragmented proteins can inhibit the ability to identify or properly rank the true protein sequence, depending on the relative signal strength of the labeled peptides that are deconvolved by the algorithm of the invention. Relative signal strength being defined as the labeled peptide fragment ion abundance relative to the abundance of other ions and noise in the mass spectrum. The first feature is the multiple charge states of the parent protein and the unlabeled scission by products of the labeled peptide fragments contribute counts at all m/z. The charge contribution of ions that reach the detector plate earlier may cause additional baseline drift in the higher m/z ions that strike the detector later. This is observed as an apparent baseline shift in the mass spectrum (FIG. 1). The multiple charge states of the parent protein may also contribute to local baseline variations in the same way at m/z positions above about 1000 amu. This is more clearly observed in FIG. 1 at m/z positions above about 2000 amu.

Figure 2:
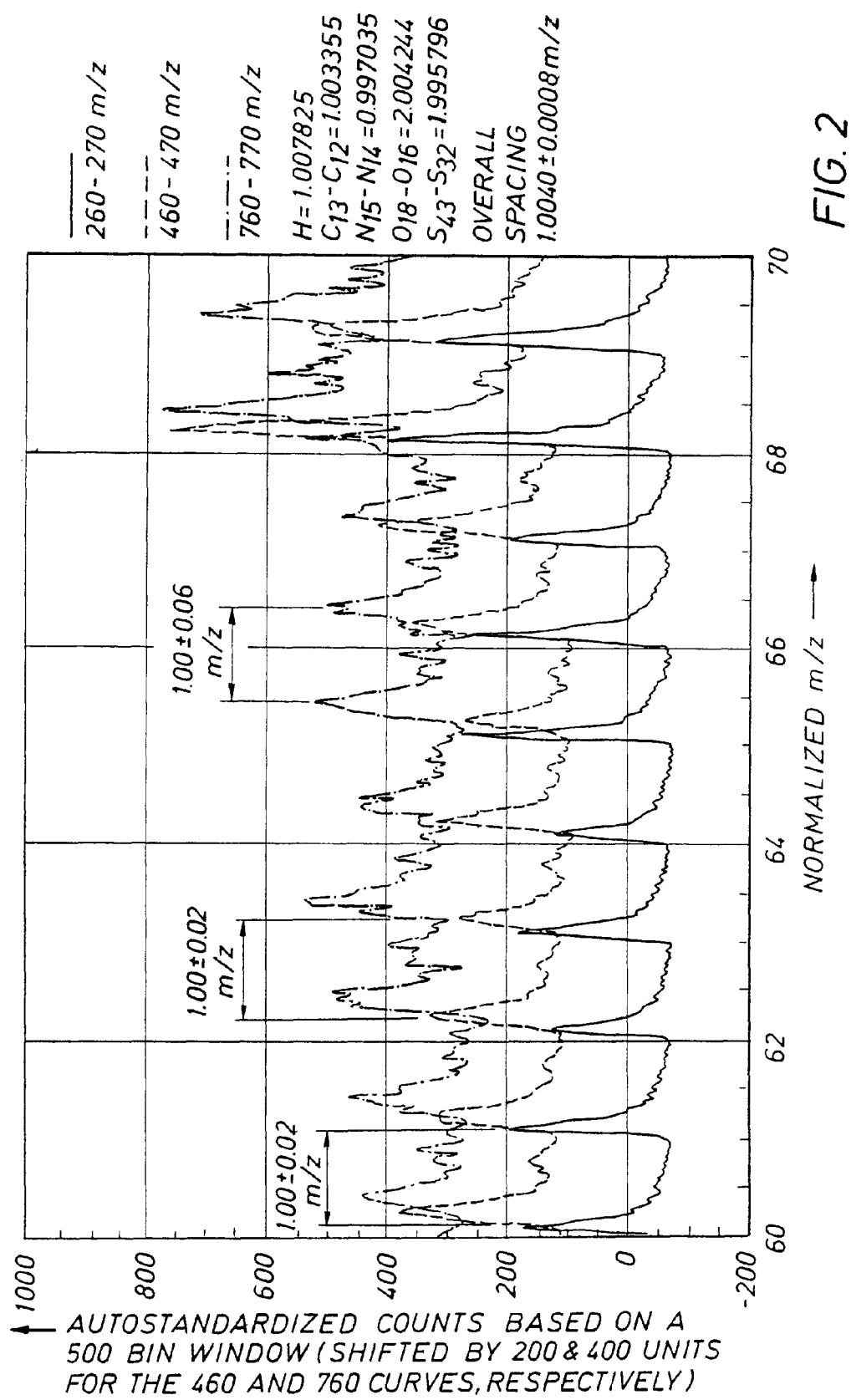
FIG. 2 illustrates periodic noise which appears in certain types of mass spectrum data.

The second feature observed is (FIG. 2) that highly fragmenting conditions (e.g., high nozzle potentials for in-source fragmentation) result in an increased abundance of fragment ions at periodic mass to charge positions in the mass spectrometer. On a mass calibration scale of 12C defined as 12.000000, these protein fragments form a characteristic pattern of peaks spaced about 1 amu apart. At highly efficient fragmentation conditions a peak appears at nearly every 1 amu spacing in the mass spectrum. The average peak to peak spacing is observed to vary slightly with the particular protein being fragmented. This is believed to be due to slight differences in the elemental composition of the protein or of the fragments represented by the peaks at each amu.

Figure 3:
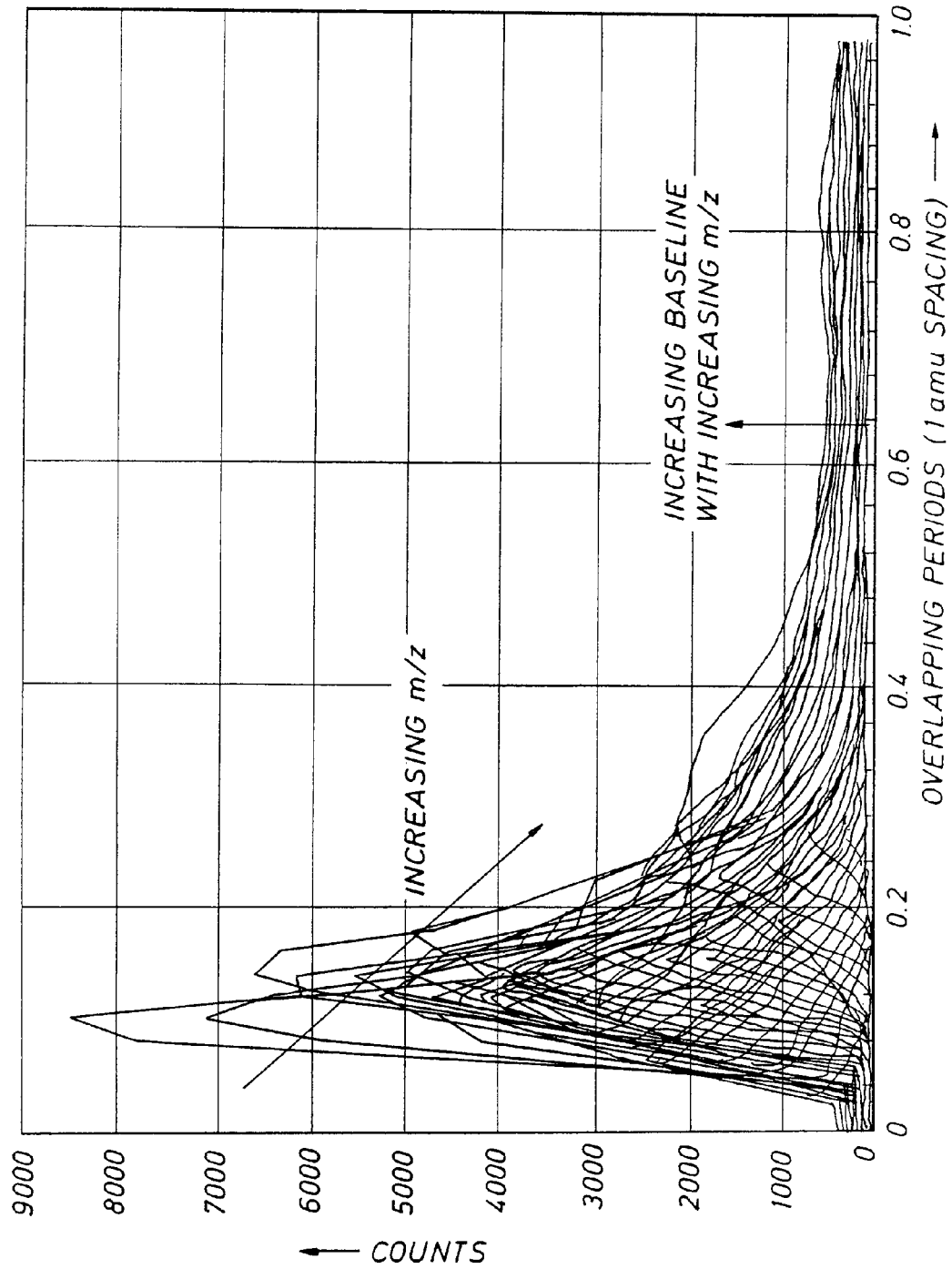
FIG. 3 shows the periodic noise in overlapping periods.

At highly fragmenting conditions virtually all the peaks in the mass spectrum overlay this nearly 1 amu pattern (FIG. 3). It is this observation that enables the key aspects of the current invention. First, since most of the peaks overlay this pattern (or a multiple charge state analog of this pattern) it is possible to easily distinguish the signal peaks from labeled fragments that lie off this periodic spacing, such as labeled fragments wherein the label contains one or more elements with an unusual nuclear binding energy. Second, the periodicity allows for the determination of local minima and maxima in the mass spectrum, such that the spectrum can be corrected for local noise, allowing for a better determination of the actual abundance of counts at each mass-to-charge position in the mass spectrum. Third, an average or characteristic peak shape can be determined for the unwanted spectral noise at highly fragmenting conditions and this noise deconvolved or subtracted from the rest of the mass spectrum, thus reducing its contribution to the ranking algorithm and improving the confidence of the sequence determination produced by the algorithm of the invention. It is obvious to those trained in the art that other larger periodicity patterns may also be found in the data and similarly applied to assist in sequence deconvolution in addition to this major pattern shown.

Labels

As noted above, the following considerations are relevant to the selection of a labeling agent:

(i) the mass of the label is preferably unique and preferably shifts the fragment masses to regions of the spectrum with low background;

(ii) the label preferably contains fixed positive or negative charges to direct remote charge fragmentation at the N- or C-terminus;

(iii) the label is preferably robust under the fragmentation conditions and does not undergo unfavorable fragmentation;

(iv) the labeling chemistry is preferably efficient under a range of conditions, particularly denaturing conditions, thereby reproducibly and uniformly labeling the N- or C-terminus;

(v) the labeled protein preferably remains soluble in the MS buffer system of choice; and (vi) the label preferably increases the ionization efficiency of the protein, or at least does not suppress it;

(vii) the label may contain a mixture of two or more isotopically distinct species to generate a unique mass spectrometric pattern at each labeled fragment position.

In view of the label selection criteria, preferred labeling moieties are those that have a detection enhancement component, an ion mass signature component and a C-terminus or N-terminus reactive functional group. The reactive group can be directly attached to either or both of the other two label components.

In an embodiment, labels may be used in pairs to further increase the ability to identify the mass ladder from other peaks in the mass spectrum. The use of mixed isotope labels is particularly suited for further deconvolution of the labeled fragment peaks, since abundant isotope pairs will only exist for labeled fragments in the mass spectrum and the isotopes typically exhibit similar ionization and fragmentation efficiencies. Analogs of a label that differ by one or more methyl or methylene groups, or charge state may also be used. Even two chemically distinct molecules may be used in dual labeling situations to enhance the identification of the labeled fragment mass ladder. In one embodiment, a single sample can be labeled simultaneously with dual labels and the combined mass spectrum generated. In a preferred embodiment, duplicate samples can be labeled independently and mixed in roughly similar proportions prior to fragmentation on the MS. This embodiment is preferable because it minimizes the possibility of signal dilution when side residues are also labeled. In another embodiment duplicate samples are labeled with separate labels, fragmented separately on the MS, and the mass spectra added together to form a virtual dual labeled spectrum.

In another embodiment, the reactive functional group is separated from one or both of the detection enhancement component and the ion mass signature component by a linker. The linker is preferably designed such that it is chemically stable and inert, and such that it allows efficient separation of the reactive group and at least one of the other two components of the tag. Within a preferred embodiment of the invention, the linker is composed of a hydrocarbon chain or, most preferably, of a hydrocarbon chain linked to an aryl or heteroaryl ring and preferably provides additional separation between the ionizable group and the linking group.

As will be understood by one of ordinary skill in the art, a variety of hydrocarbon chains and modified hydrocarbon chains may be utilized within the present invention. Preferred hydrocarbon chains which are attached to the phenyl ring may be found in the family of alkanes, with particularly preferred linkers ranging from 2 carbon atoms to about 20 carbon atoms in length. Within a preferred embodiment of the invention, the linker is a phenethyl group.

Detection Enhancement Components

A detection enhancement component, as used herein, refers to a portion of the labeling moiety that facilitates detection of the protein fragments in the mass spectrometer. Accordingly, the detection enhancement component may provide a positively charged ionic species under fragmentation conditions in a mass spectrometer ionization chamber, or the component may provide a negatively charged ionic species under fragmentation conditions in a mass spectrometer ionization chamber. For many of the detection enhancement components, the amount of ionized species present will depend on the medium used to solubilize the protein. Preferred detection enhancement components (i.e., species that can generate a positive or negative charge) can be classified into three categories: 1) components that carry "hard" charge, 2) components that carry "soft" charge, and 3) components that provide no charge but are in close proximity to protein residues that carry "soft" charge.

Components that carry "hard" charge are arrangements of atoms that are substantially ionized under all conditions, regardless of medium pH. "Hard" positively-charged detection enhancement components include, but are not limited to, tetraalkyl or tetraaryl ammonium groups, tetraalkyl or tetraaryl phosphonium groups, and N-alkylated or N-acylated heterocyclyl and heteroaryl (e.g., pyridinium) groups. "Hard" negatively-charged detection components include, but are not limited to, tetraalkyl or tetraacyl borate groups.

Components that carry "soft" charge are arrangements of atoms that are ionized at a pH above or below their pKa, respectively (i.e., bases and acids). Within the context of the current invention, "soft" positive charges include those bases with a pKa of greater than 8, preferably greater than 10, and most preferably greater than 12. Within the context of the current invention, "soft" negative charges include those acids with a pKa of less than 4.5, and preferably less than 2, and most preferably less than 1. At the extremes of pKa, the "soft" charges approach classification as "hard" charges. "Soft" positively-charged detection enhancement components include, but are not limited to, 1°, 2°, and 3° alkyl or aryl ammonium groups, substituted and unsubstituted heterocyclyl and heteroaryl (e.g., pyridinium) groups, alkyl or aryl Schiff base or imine groups, and guanido groups. "Soft" negatively-charged detection enhancement components include, but are not limited to, alkyl or aryl carboxylate groups, alkyl or aryl sulfonate groups, and alkyl or aryl phosphonate or phosphate groups.

For both "hard" and "soft" charged groups, as will be understood by one of ordinary skill in the art, the groups will be accompanied by counterions of opposite charge. For example, within various embodiments, the counterions for positively-charged groups include oxyanions of lower alkyl organic acids (e.g., acetate), halogenated organic acids (e.g., trifluoroacetate), and organosulfonates (e.g., N-morpholinoethane sulfonate). The counterions for negatively-charged groups include, for example, ammonium cations, alkyl or aryl ammonium cations, and alkyl or aryl sulfonium cations.

Components that are neutral but are in close proximity to protein residues that carry "soft" charge (e.g, lysine, histidine, arginine, glutamic acid, or aspartic acid) can be used as detection enhancement components. In this case, the label carries no ionized or ionizable groups, and the detection enhancement is provided by a nearby protein residue that carries charge. Within the context of the present invention, close proximity is defined as within about 4 residues from the labeled terminus of the protein, and more preferably within about 2 residues of the labeled terminus of the protein.

The detection enhancement component of the label may also be multiply charged or capable of becoming multiply charged. For example, a label with multiple negative charges may incorporate one or singly charged species (e.g. carboxylate) or it may incorporate one or more multiply charged species (e.g., phosphate). In a representative example of this embodiment of the invention a species bearing multiple carboxylates, such as, for example a polymaminocarboxylate chelating agent (e.g., EDTP, DTPA) is attached to the protein. Methods of attaching polyaminocarboxylates to proteins and other species are well known in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., Bioconjugate Chem., 9: 108-117 (1998); Song et al., Bioconjugate Chem., 8: 249-255 (1997).

In a similar manner, labels having multiple positive charges can be purchased or prepared using methods accessible to those of skill in the art. For example, a labeling moiety bearing two positive charges can be rapidly and easily prepared from a diamine (e.g., ethylenediamine). In a representative synthetic route, the diamine is monoprotected using methods known in the art and the non-protected amine moiety is subsequently dialkylated with a species bearing one or more positive charges (e.g., (2-bromoethyl)trimethylammonium bromide) (Aldrich)). Deprotection using art-recognized methods provides a reactive labeling species bearing at least two positive charges. Many such simple synthetic routes to multiply charged labeling species will be apparent to one of skill in the art.

Ion Mass Signature Component

The ion mass signature component is the portion of the labeling moiety which preferably exhibits a unique ion mass signature in mass spectrometric analyses. The ion mass signature component includes moieties that do not efficiently ionize under conditions in which proteins ionize (e.g., aromatic carbon compounds) as well as molecules that readily ionize under protein ionizing conditions to generate multiply charged ionic species. Both types of chemical entities can be used to shift the ion/mass signature of the amino acids and peptides attached to the label (after fragmentation of the labeled protein) in the mass spectrum. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

In an embodiment, the ion mass signature component can be any element that exhibits a nuclear binding energy different from the major constituents of proteins. The major constituents of proteins are: C, H, N, O, and S. Defining nuclear binding energies in terms of the $^{12}C=12.000000$ mass standard, preferred elements with unique ion mass signatures are those elements in the periodic table with atomic numbers between 17 (Cl) and 77 (Ir). Particularly preferred elements for use as ion mass signature components of the label include elements with atomic numbers between 35 (Br) and 63 (Eu). The most preferred elements for use as ion mass signature components are those with atomic numbers between 39 (Y) and 58 (Ce). Br and Eu are particularly preferred components of the label because they exhibit both two stable isotopes of roughly equal proportions and nuclear binding energies that differ significantly from the periodic peak pattern observed for proteins fragmented in the mass spectrometer. The elements I and Y are also particularly preferred ion mass signature components because they exhibit the greatest difference in nuclear binding energy from the periodic protein fragment peak in the mass spectrum and because they are readily incorporated into labels. It is observed that many transition metals are within the preferred and most preferred lists of unique ion mass signature elements. It is readily apparent to those skilled in the art that many or all of these materials can be incorporated into labels as chelates, similar to the known Y and Eu chelates.

In contrast to the limited utility of F as a mass defect element (Schmidt et al. WO 99/32501 (Jul. 1, 1999)), the present invention uses mass defect elements that present a much greater mass difference and thus broader utility. For example, a single iodine substitution on an aryl group creates a mass defect of 0.1033 amu more than a 5 fold improvement over that of 5 aryl F substitutions. A single I on an aryl ring ($C_6H_4I$) exhibits a monoisotopic mass of 202.935777 amu. This is 192 ppm different from the nearest combination of stable isotope and heteroatom-containing organic molecule ($[^{12}C]_9[^{15}N][^{16}O]_5$) at 202.974687 amu. Therefore, a single substitution of any elements that exhibit a mass defect similar to that of I (i.e., atomic numbers between 35 and 63) will yield a discernable mass defect (at the 10 ppm level) to a total mass of 3891 amu for any combination of organic heteroatoms. Two such elements will exhibit a discernable mass defect to a total mass of 7782 amu. Three such elements will exhibit a discernable mass defect to a total mass of 11673 amu. Alternatively, single, double, and triple additions of I (or an equivalent mass defect element) can be discriminated from each other to a total mass of 4970 amu in a mass spec with 10 ppm mass resolution.

In another embodiment, a unique ion mass signature component may be created by using a multiply charged label. Such a multiply charged label may incorporate an element with a different nuclear binding energy or may consist solely of elements similar in nuclear binding energies to that of the major protein constituents. Such charge states may be formed with "hard" or "soft" or a combination of "hard" and "soft" charges incorporated into the label. Multiple "hard" charge states between 2 and 4 are preferred. A multiple "hard" charge state of 3 is most preferred when the label consists solely of elements with nuclear binding energies similar to C, H, N, O, and S. A multiple "hard" charge state of 2 is most preferred when the label contains at least one element exhibiting a nuclear binding energy different from C, H, N, O, and S.

As will be understood by one of skill in the art, spurious mass spectral peaks can arise not only from the fragmentation of unlabeled amino acids and peptides but also from impurities in the sample and/or matrix. In order to further increase the uniqueness of the ion mass signature of the label and to be able to identify desired labeled fragment peaks from "noise," it is preferable to shift the labeled fragments to regions of less spectral noise by optimizing the mass of the label. For example, it is preferred that the label mass generate an ion greater than 100 amu and less than 700 amu. This may be done by increasing the molecular weight of a low molecular weight label or by increasing the number of charges on a high molecular weight label.

An alternative method for providing a more unique mass signature to a labeling moiety is to incorporate stable isotopes in the label (see, for example, Gygi et al., *Nature Biotechnol.* 17: 994-999 (1999)). For example, by incorporating eight deuterium atoms into a labeling moiety and labeling the protein with a 50:50 mixture of the deuterated and nondeuterated label, the resulting singly-charged fragments that include the label are easily identified as equally intense doublets; one at the mass corresponding to the species with the nondeuterated label and the other at the mass corresponding to the species with the deuterated label with a spacing of 8 amu. In a preferred embodiment, the mass difference is more than about 1 amu at the single charge state. In the most preferred embodiment the mass difference is from about 4 to about 10 amu at the single charge state. The incorporation of multiple isotopes of elements that exhibit nuclear binding energies significantly different from C, H, N, O, and S is preferred. Br and Eu elements are most preferred because the exhibit two natural isotopic abundances of about 50:50.

Another method for providing a more unique mass signature to a labeling moiety is to incorporate a mixture of alkyl and/or aryl substitutions onto the label, such that the corresponding set of fragment peaks is easily recognizable in the mass spectrum. For example, the protein can be labeled with a mixture of a label that contains a trimethyl ammonium group and the same label that contains a dimethylethylammonium group in place of the trimethyl ammonium group. This labeling moiety produces two fragment ion peaks for each amino acid in the sequence that differ by 14 amu from each other. It will be apparent to those skilled in the art that many such combinations may be derived.

Reactive Groups

A third component of the labeling moiety is a functional group which is reactive with a terminus of the polymer of interest. In certain embodiments, a functional group is reactive with a protein at the N-terminus amino group, the C-terminus amino group or another constituent of the N- or C-terminus amino acid.

The reactive functional group can be located at any position on the tag. For example, the reactive group can be located on an aryl nucleus or on a chain, such as an alkyl chain, attached to an aryl nucleus. When the reactive group is attached to an alkyl, or substituted alkyl chain tethered to an aryl nucleus, the reactive group is preferably located at a terminal position of an alkyl chain. Reactive groups and classes of reactions useful in practicing the present invention are generally those that are well known in the art of bioconjugate chemistry. Currently favored classes of reactions are those which proceed under relatively mild conditions in an aqueous or mixed aqueous/organic solvent milieu.

Particularly preferred chemistries that target the primary amino groups in proteins (including the N-terminus) include, for example: aryl fluorides, sulfonyl chlorides, cyanates, isothiocyanates, immidoesters, N-hydroxysuccinimidyl esters, O-acylisoureas, chlorocarbonates, carbonylazides, aldehydes, and alkylhalides and activated alkenes. Preferred examples of chemical constituents that react with the carboxyl groups of proteins are benzyl halides and carbodiimide, particularly if stabilized using N-hydroxysuccinimide. Both of these carboxyl labeling approaches are expected to label carboxyl containing amino acid residues (e.g., aspartate and glutamate) along with that of the C-terminus. These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

The reactive functional groups can be chosen such that they do not participate in, or interfere with, the reactions necessary to assemble the tag. Alternatively, a reactive functional group can be protected from participating in the reaction by the presence of a protecting group.

Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

One of skill in the art will understand that labeling techniques are readily available for a number of the labeling moieties. An example of an N-terminus labeling group (dansyl chloride) and a C-terminus labeling group (carbodiimide) are provided as illustrative of the invention, with references to a more complete description of their use. The focus on these two labeling moieties is for clarity of illustration and does not limit the scope of the invention.

Dansyl chloride undergoes a nucleophilic attack by the amines in proteins at alkaline pH, producing an aromatic sulfonamide. Sulfonyl chlorides, however, depending on the pH, can also react with secondary amines. The aromatic constituent enables spectroscopic (e.g., fluorescence) detection of the reaction product. Dansyl chloride also reacts with the $\epsilon$-amino group of lysine. The pK differences between $\alpha$- and $\epsilon$ amines can be exploited to modify one of these groups preferentially to the other.

Carbodiimides react with carboxyl groups to form an O-acylisourea intermediate that is highly unstable in aqueous solution but can be stabilized through the addition of N-hydroxysuccinimide resulting in the formation of an acid stable intermediate that can be made to react with primary amines, producing an amide. Alternatively, in the absence of good nucleophiles (e.g., N-hydroxysuccinimide or other amines), the unstable O-acylisourea intermediate may rearrange to form a stable N-acylisourea. This species can be used directly as a protein label. The carboxyl terminus, glutamate and aspartate residues are all targets for carbodiimides in proteins at acidic pH (4.5-5). Carbodiimide chemistry is useful for labeling the C-terminus of protein. When carbodiimide chemistry is utilized, it is generally preferred that an excess of amine is added to the protein solution to inhibit crosslinking reactions. In another exemplary embodiment, a protein amine is labeled in a two-step process; an amine-containing fluorescent molecule is tethered to the protein through an N-hydroxysuccinimide intermediate of the protein or of a spacer arm attached to the protein.

Synthesis

Once the reactive group, linker, and ionizable groups have been selected, the final compound may be synthesized by one of ordinary skill in the art utilizing standard organic chemistry reactions. A preferred compound for use within the present invention is PETMA-PITC, or an analogous agent. This compound retains the excellent characteristics of phenylisothiocyanate in the coupling. Furthermore, the compound performs well as a label in analytical methods because the electron structure of the phenyl ring is sufficiently separated from the quaternary ammonium group by the ethyl linker, thus allowing the isothiocyanate to react undisturbed by the quaternary ammonium group. Preparation of PETMA-PITC, C5 PETMA-PITC and PITC-311 are described in Aebersold et al., U.S. Pat. No. 5,534,440, issued Jul. 9, 1996.

With the selection of a suitable labeling moiety, conditions for attaching the label to an oligomer should ensure that a terminus is uniformly labeled and an oligomer remains soluble in an appropriate MS buffer system. For example, conditions for attaching label to a protein should ensure that the N- or C-terminus of the protein is uniformly labeled and that the labeled protein remains soluble in appropriate MS buffer systems. Typically, labeling will be carried out under denaturing conditions (e.g., surfactants or 8M urea). Surfactants and urea both suppress MS ionization and methods that provide rapid clean up and transfer of the labeled protein sample to a suitable MS buffer should also be employed.

Detectable Moieties

In another preferred embodiment, a protein is labeled with a moiety that enhances its detectability in, for example, protein purification and separation processes (e.g., electrophoresis). The detectable moiety may be detected $b_y$, for example, spectroscopy (e.g., UV/Vis, fluorescence, electron spin resonance (ESR), nuclear magnetic resonance (NMR) and the like), detection of radioactive isotopes, etc. When the protein is detected by UV/Vis, it is generally desirable to attach a chromophoric label to the protein (e.g., phenyl, napthyl, etc.). Similarly, for detection by fluorescence spectroscopy, a fluorophore is preferably attached to the protein. For example, Quantum Dye™ is a fluorescent Eu chelate and 5-carboxy-2',4',5',7'-tetrabromosulfonefluorescein succinimidyl ester is an N-terminal reactive, bomine-containing fluorophore (commercially available from Research Organics, catalog #0723Q and Molecular Probes, catalog #C-6166, respectively). For ESR, the detectable moiety can be a free radical, such as a moiety including a nitroxide group. When the protein is detected by an NMR method, the detectable moiety can be enriched with an NMR accessible nuclei, such as fluorine, $^{13}C$, and the like.

In a preferred embodiment, the detectable moiety is a fluorophore. Many reactive fluorescent labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and PE-Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

There is a great deal of practical guidance available in the literature for selecting an appropriate fluorophore for a particular tag, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In addition to fluorophores that are attached directly to a protein, the fluorophores can also be attached by indirect means. In an exemplary embodiment, a ligand molecule (e.g., biotin) is preferably covalently bound to the protein. The ligand then binds to another molecule (e.g., streptavidin), which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Fluorophores that may be used in conjunction with the methods of the invention, include, but are not limited to fluoresceins, and rhodamine dyes. Many suitable forms of these compounds are widely available commercially with substituents on their phenyl moieties, which can be used as the bonding functionality for attachment of the fluorophore to a protein. Alternatively, fluorescent compounds such as the naphthylamines, having an amino group in the alpha or beta position, may be used in conjunction with methods described herein. Included among such naphthylamino compounds are 1-dimethylaminonaphthyl-5-sulfonate, 1-anilino-8-naphthalene sulfonate and 2-p-toluidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Useful fluorescent detectable moieties can be made to fluoresce by exciting them in any manner known in the art, including, for example, with light or electrochemical energy (see, for example, Kulmala et al, *Analytica Chimica Acta* 386: 1 (1999)). Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

The fewer the processing steps between any separation technique and MS sequencing method, the faster that proteins can be identified, and the lower the cost of proteomic research. Typical electrophoresis buffers (e.g., Hochstrasser et al. and O'Farrel) contain components (e.g., tris(hydroxymethyl)aminomethane buffers and sodium dodecyl sulfate, that suppress the ionization of proteins in the mass spectrometer. These components may be replaced with other more volatile components (e.g., morpholinoalkylsulfonate buffers and ephemeral surfactants) that do not suppress ionization in the MS. In another embodiment, the samples are diluted with ammonium bicarbonate or ammonium acetate buffer to provide a volatile proton source for the mass spectrometer. In another embodiment, a buffer exchange is conducted through by chromatographic or tangential flow dialysis as the sample is transported from the outlet of the separation process to the inlet of the MS.

Labeling Procedure

In some instances, salts (e.g., TRIS and SDS) and urea present in electrophoresis buffers can suppress ionization of the labeled proteins and can generate small mass/charge ions that potentially confuse sequence analysis. Accordingly, spin dialysis procedures can be employed to rapidly exchange buffer systems prior to MS analysis. Alternatively, desalting columns (e.g., the ZipTip™ tip sold by Millipore) can be used for sample clean up and buffer exchange. Desalted samples can be resuspended in 0.1M ammonium bicarbonate as described by Wilm and Mann with minimal addition of methanol, or in 0.01M ammonium acetate buffer (with 0.1% formic acid) with minimal addition of acetonitrile as described by Mark.

The coupling rates of the compound may be tested to ensure that the compound is suitable for sequencing polypeptides. In general, the faster the coupling rate the more preferred the compound. Coupling rates of between 2 and 10 minutes at 50° C. to 70° C. are particularly preferred. Similarly, fast reaction rates are also preferred, because exposure to the reaction mixture over an extended period of time might hydrolyze the peptide bonds, or lead to inefficient and irreproducible side reactions with the polypeptide residues, which could complicate mass spectral deconvolution.

In another preferred embodiment, one or more of the components of a protein mixture is reversibly attached to a solid support prior to the label being attached to a polypeptide. Various materials may be used as solid supports, including, for example, numerous resins, membranes or papers. These supports may additionally be derivatized to incorporate a cleavable functionality. A number of cleavable groups that may be used for this purpose include disulfides (—S—S—), glycol (—CH[OH]—CH[OH]—), azo (—N=N—), sulfone (—S[=O]—), and ester (—COO—) linkages (see, Tae, *Methods in Enzymology,* 91:580 (1983)). Supports which are particularly preferred include membranes such as Sequelon TM (Milligen/Biosearch, Burlington, Mass.). Representative materials for the construction of these supports include, among others, polystyrene, porous glass, polyvinylidinefluoride and polyacrylamide. In particular, polystyrene supports include, among others: (1) a (2-aminoethyl) aminomethyl polystyrene (see, Laursen, *J. Am. Chem. Soc.* 88: 5344 (1966)); (2) a polystyrene similar to number (1) with an aryl amino group (see, Laursen, *Eur. J. Biochem.* 20: 89 (1971)); (3) amino polystyrene (see, Laursen et al., *FEBS Lett.* 21: 67 (1972)); and (4) triethylenetetramine polystyrene (see, Horn et al., *FEBS Lett.* 36:285 (1973)). Porous glass supports include: (1) 3-aminopropyl glass (see, Wachter et al., *FEBS Lett.* 35: 97 (1973)); and (2)N-(2-aminoethyl)-3-aminopropyl glass (see, Bridgen, *FEBS Lett.* 50: 159 (1975)). Reaction of these derivatized porous glass supports with p-phenylene diisothiocyanate leads to activated isothiocyanato glasses (see, Wachter et al., supra). Polyacrylamide-based supports are also useful, including a cross-linked β-alanylhexamethylenediamine polydimethylacrylamide (see, Atherton et al., *FEBS Lett.* 64: 173 (1976)), and an N-aminoethyl polyacrylamide (see, Cavadore et al., *FEBS Lett.* 66: 155 (1976)).

One of ordinary skill in the art will readily utilize appropriate chemistry to couple the polypeptide to the solid supports described above (see, generally Machleidt and Wachter, Methods in Enzymology: [29] New Supports in Solid-Phase Sequencing 263-277 (1974). Preferred supports and coupling methods include the use of aminophenyl glass fiber paper with EDC coupling (see, Aebersold et al., *Anal. Biochem* 187: 56-65 (1990)); DITC glass filters (see, Aebersold et al., *Biochem.* 27: 6860-6867 (1988) and the membrane polyvinylidinefluoride (PVDF) (Immobilon P TM, Milligen/Biosearch, Burlington, Mass.), along with SequeNet TM chemistry (see, Pappin et al., CURRENT RESEARCH IN PROTEIN CHEMISTRY, Villafranca J. (ed.), pp. 191-202, Academic Press, San Diego, 1990)).

In the practice of the present invention, attachment of the polypeptide to the solid support may occur by either covalent or non-covalent interaction between the polypeptide and solid support. For non-covalent attachment of the polypeptide to the solid support, the solid support is chosen such that the polypeptide attaches to the solid support by non-covalent interactions. For example, a glass fiber solid support may be coated with polybrene, a polymeric quaternary ammonium salt (see, Tarr et al., *Anal. Biochem.*, 84:622 (1978)), to provide a solid support surface which will non-covalently attach the polypeptide. Other suitable adsorptive solid phases are commercially available. For example, polypeptides in solution may be immobilized on synthetic polymers such as polyvinylidine difluoride (PVDF, Immobilon, Millipore Corp., Bedford, Mass.) or PVDF coated with a cationic surface (Immobilon CD, Millipore Corp., Bedford, Mass.). These supports may be used with or without polybrene. Alternatively, polypeptide samples can be prepared for sequencing by extraction of the polypeptide directly from polyacrylamide by a process called electroblotting. The electroblotting process eliminates the isolation of polypeptide from other peptides which may be present in solution. Suitable electroblotting membranes include Immobilon and Immobilon CD (Millipore Corp., Bedford, Mass.).

More recently, automated methods have been developed that allow chemistries to be performed on polypeptides immobilized on solid supports by non-covalent, hydrophobic interaction. In this approach, the samples in aqueous buffers, which may contain salts and denaturants, are pressure-loaded onto columns containing a solid support. The bound polypeptide is then pressure-rinsed to remove interfering components, leaving the bound polypeptide ready for labeling (see, Hewlett-Packard Product Brochure 23-5091-5168E (November, 1992) and Horn, U.S. Pat. No. 5,918,273 (Jun. 29, 1999).

The bound polypeptide is reacted under conditions and for a time sufficient for coupling to occur between the terminal amino acids of the polypeptide and the labeling moiety. The physical properties of the support may be selected to optimize the reaction conditions for a specific labeling moiety. For example, the strongly polar nature of the PETMA-PITC dictates covalent attachment of the polypeptide. Preferably, coupling with the amino groups of the polypeptide occurs under basic conditions, for example, in the presence of an organic base such as trimethylamine, or N-ethylmorpholine. In a preferred embodiment, the label is allowed to react with the bound peptide in the presence of 5% N-ethylmorpholine in methanol:water (75:25 v/v). Because of the mode of attachment, excess of reagent, coupling base and reaction by-products can be removed by very polar washing solvents prior to removal and sequencing of the labeled polypeptide by mass spectrometry. Various reagents are suitable as washing solvents, including, for example, methanol, water, mixtures of methanol and water, or acetone.

Less polar reagents, such as PITC-311, may be reacted with polypeptides attached to a sold support preferably by hydrophobic, non-covalent interactions. In this case, less polar washes are preferred, such as heptane, ethylacetate, and chloroform. Following the washing cycle, the labeled polypeptide is dissociated from the solid support by elution with solvent containing 50% to 80% of aqueous methanol or acetonitrile.

When the labeling reaction is conducted entirely in solution phase, the reaction mixture is preferably submitted to a purification cycle, such as dialysis, gel permeation chromatography, and the like.

In another aspect, the present invention provides a method for sequencing a portion of a protein in a protein mixture, the method comprising:

contacting the protein mixture with a C-terminus or N-terminus labeling moiety to covalently attach a label to the C- or N-terminus of the protein and form a labeled protein mixture, the C-terminus or N-terminus labeling moiety may comprise at least one element having an atomic number from 17 to 77, with the proviso that said element is other than sulfur;

(a) separating individual labeled proteins in the protein mixture; and (b) analyzing the labeled proteins from step (b) by a mass spectrometric method to determine the sequence of at least two C-terminus or two N-terminus residues.

(c) In one group of embodiments, the method further comprises:

(d) identifying the protein by using the sequence of at least two C-terminus or two N-terminus residues in combination with a separation coordinate of the labeled protein and the protein terminus location of the sequence to search predicted protein sequences from a database of gene sequence data.

Separation

In a preferred embodiment, the tagging procedure is performed on a mixture of proteins. Following the tagging procedure the mixture of proteins is submitted to a separation process, which preferably, allows the separation of the protein mixture into discrete fractions. Each fraction is preferably substantially enriched in only one labeled protein of the protein mixture.

The methods of the present invention are utilized in order to determine the sequence of a polypeptide. Within preferred embodiments of the invention, the polypeptide is "substantially pure," which means that the polypeptide is about 80% homogeneous, and preferably about 99% or greater homogeneous. Many methods well known to those of ordinary skill in the art may be utilized to purify the polypeptide prior to determining its amino acid sequence. Representative examples include HPLC, Reverse Phase-High Pressure Liquid Chromatography (RP-HPLC), gel electrophoresis, chromatography, or any of a number of peptide purification methods (see, generally the series of volumes entitled METHODS IN PROTEIN SEQUENCE ANALYSIS).

Even more preferred is the use of capillary electrophoresis and particularly, multi-dimensional capillary electrophoresis, such as that described in the commonly assigned co-pending U.S. patent application Ser. No. 09/513,486, titled "Protein Separation via Multidimensional Electrophoresis," and filed Feb. 25, 2000.

Although substantially pure polypeptides are preferably utilized within the methods described herein, it is also possible to determine the sequence of polypeptide mixtures. Briefly, in one embodiment, an algorithm is utilized in order to determine all of the hypothetical sequences with a calculated mass equal to the observed mass of one of the peptides in the mixture. See, Johnson et al., *Protein Science* 1: 1083-1091 (1992). These sequences are then assigned figures of merit according to how well each of them accounts for the fragment ions in the tandem mass spectrum of the peptide utilizing such algorithms, the sequence of polypeptides within the mixture may be readily determined.

As described above, the methods herein are particularly useful for identifying proteins from a healthy or diseased tissue sample. In one group of embodiments, the methods are applied to both a mixture of proteins from a healthy tissue sample and a mixture of proteins from a diseased tissue sample. Accordingly, the protein mixtures used in this aspect of the invention can be obtained from essentially any source. Methods of isolating proteins from tissue samples are well known.

Within the present invention, a polypeptide with a derivatized terminal amino acid is sequenced by a mass spectrometer. Various mass spectrometers may be used within the present invention. Representative examples include, triple quadrapole mass spectrometers, magnetic sector instruments (magnetic tandem mass spectrometer, JEOL, Peabody, Mass.); ion-spray mass spectrometers, Bruins et al., *Anal. Chem.* 59: 2642-2647 (1987); electrospray mass spectrometers, Fenn et al., *Science* 246: 64-71 (1989); laser desorption time-of-flight nmass spectrometers, Karas et al., *Anal. Chem.* 60: 2299-2301 (1988), and a Fourier Transform Ion Cyclotron Resonance Mass Spectrometer (Extrel Corp., Pittsburgh, Mass.). Within a preferred embodiment, an electrospray mass spectrometer (Mariner™ model, PE Biosystems, Foster City, Calif.) is utilized to fragment the derivatized terminal polypeptide, and a time-of-flight detector with better than 50 ppm mass accuracy is used to determine the sequence from the masses of the labeled fragments.

One of skill in the art will appreciate that the sequence information obtained using the methods of the invention may be combined with other characteristics of the protein under analysis to even further reduce the number possible identities of the protein. Thus, in a preferred embodiment, the method of the invention combines information from a protein sequence tag with one or more other protein characteristics to identify the protein. Data that is useful to supplement the sequence data includes, but is not limited to, amino acid composition, the number and identity of specific residues (e.g. cysteine), cleavage information, proteolytic (e.g., tryptic) and or chemolytic peptide mass, subcellular location, and separation coordinates (e.g., retention time, pI, 2-D electrophoresis coordinates, etc.). Other forms of data characteristic of a particular protein or class of proteins that can be combined with information from the PSTs of the invention to identify a protein will be apparent to those of skill in the art. As the body of data characteristic of a particular protein becomes more comprehensive, proteins under analysis can be identified using shorter protein sequence tags.

Thus, in yet another preferred embodiment, information regarding one or more characteristics of a protein is combined with information from a PST of about 4 amino acids in length, more preferably about 3 amino acids in length, more preferably still, about 2 amino acids in length is used to identify the protein.

Further details concerning labeling methods and sequencing methods may be obtained from the following three co-pending applications which are all hereby incorporated herein by reference: (a) U.S. patent application Ser. No. 09/513,395, filed Feb. 25, 2000 and entitled "Methods for Protein Sequencing;" (b) U.S. patent application Ser. No. 09/513,907, filed Feb. 25, 2000 and entitled "Polypeptide Fingerprinting and Bioinformatics Database System;" and (c) U.S. Provisional Patent Application Ser. No. 60/242,165, filed Oct. 19, 2000, by inventors Luke V. Schneider and Michael P. Hall, and entitled "Methods of Sequencing Proteins".

Sequencing Algorithm

One embodiment of the current invention includes the use of a mathematical algorithm for determining the protein sequence tag directly from mass spectra of fragmented labeled proteins. The algorithm may be used to determine an oligomer sequence, preferably a protein sequence tag from either terminus of the protein, providing that a unique mass tag label is attached to the terminus being sequenced. The starting mass spectra for use in the algorithm may be produced by any mass spectrometer in which an oligomer, preferably a protein or peptide, can be fragmented. In addition, peptides and proteins may be partially digested, such as with hydrazine, prior to introduction into the mass spectrometer. Time-of-flight mass spectra are preferred because of their improved mass accuracy over other mass spectrometer detection systems. However, other less accurate mass spectrometer detection systems may be used, particularly if an internal mass standard, such as fragmented label with no peptide attached, is used to improve the mass accuracy of the resulting mass spectrum. Protein fragmentation may be conducted either by CID in the collision cell of a tandem mass spectrometer or by in-source fragmentation in an electrospray or MALDI ionization source.

The algorithm requires the use of both the mass to charge position of a signal and its relative abundance. In one embodiment, the relative abundance of the signal is compared to that of immediately adjacent mass to charge positions and used to quantify the relative probability that a peak is present at the mass to charge position of interest. In this embodiment, the relative probabilities that a peak is present are compared among all competing sequences. In another embodiment the signal at each mass to charge position of interest is directly compared to that at the mass to charge positions of all competing sequences. The latter method is described further for clarity. It is obvious to those skilled in the art that this method may be adapted in many ways to provide a similar system for ranking competing sequences based on the relative abundance of the signal at the mass to charge positions correlated with each competing sequence.

The algorithm further consists in one embodiment of a cumulative sequence ranking system, in which the relative abundance of the ions predicted to result from each possible sequence are combined by product or summation with the relative abundances of ions predicted to result from subsequent residues (Equation 1). In this way sequence-specific differences in the ionization or fragmentation efficiency and adventitious matrix or overlapping noise peaks that confound the correct sequence assignment at each residue position in the polypeptide chain may be eliminated. The probability of an erroneous sequence assignment at any given residue position propagating forward to subsequent residue positions is lower than that associated with the true sequence. The overall rank for each possible sequence j can then determined by:

$$R_{j,n} = \prod_{i=1}^{n} p_{i,j} \text{ or } \sum_{i=1}^{n} p_{i,j} \tag{1}$$

where $R_{j,n}$ is the cumulative ranking given to any given sequence j at residue length n, and is the relative rank assigned to the sequence amongst its j peers at residue length i. It is apparent to those skilled in the art that many methods can be used to assign a relative rank (p) to each sequence j at any residue length i, consistent with comparison of the relative abundances of the signals at each competing mass to charge position (in supra). In a preferred embodiment, the relative ranking (p) of competing sequence possibilities at each residue length (i) may be determined by autoscaling the possibilities. In a particular variation of this method, the ranking (p) may be assigned based on an assumed, or demonstrated probability distribution, such as the normal (Gaussian) probability distribution or the log normal (Poisson) probability distribution, such that the relative rank for each sequence will vary between 0 and 1. For example, $$p_i = NORMDIST\left[\frac{(C_{i,j} - \overline{C}_i)}{\sigma_i}\right] \quad (2)$$

where;

$$\overline{C}_i = \frac{\sum_{j=1}^{19^i} C_{i,j}}{19^i} \quad (3)$$

and $$\sigma_i = \sqrt{\frac{\sum_{j=1}^{19^i} C_{i,j}^2 - \frac{\left(\sum_{j=1}^{19^i} C_{i,j}\right)^2}{19^i}}{(19^i - 1)}} \quad (4)$$

One of skill in the art will appreciate that the signal ($C_{i,j}$) corresponding to any sequence j containing i amino acid residues may be determined by any method which relates this signal back to the relative signal abundance in the mass spectrum. Collision induced fragmentation in the mass spectrometer may result in the production of more than one type of ion. CID methods in a tandem mass spectrometer commonly result in a, b, and c ion types from the N-terminus and x, y, and z ions from the C-terminus. In addition, the label and certain amino acid residues may contain "soft" charges that may lead to the production of labeled peptide fragments at more than one mass to charge position in the spectrum, depending on the number of such "soft" charges. In a variation of the method, the signals associated with each ion type and possible charge state may be combined to produce a cumulative signal associated with any given sequence j:

$$C_{i,j} = \sum_{k=min\ charge\ states}^{max\ charge\ states} \sum_{l=1}^{max\ ion\ types} c_{i,j,k,l} \quad (5)$$

where c is determined by calculating the (m/z) of the each ion type (l) and charge state (k) and looking up the corresponding counts ($c_{i,j,k,l}$) in the mass spectral data.

$$c_{i,j,k,l} = LOOKUP[(m/z)_{i,j,k,l}] \quad (6)$$

The mass to charge ratio calculation for any residue length i, sequence j, charge state k, and ion type l, is to be determined from the stoichiometry and possible charge states of the amino acids and any attached labels in the sequence by methods previously described.

A number of variations can be made to the basic sequencing method described. For example, in a preferred embodiment, the number of charge states and ion types that are used for determination of the total signal associated with any given sequence may be restricted to particular subsets empirically found to be most often associated with the fragmentation method. CID fragmentation in a tandem mass spectrometer preferentially yields b ions and y ions in the most abundance and c and x ions in the least abundance. In source fragmentation is found to yield only a, b, and y ions in significant abundance. In these cases, the algorithm may be preferentially adapted to ignore c and x ions or c, x, and z ions. Ion abundance also appears to diminish for the higher possible charge states of peptide fragments in both CID and in source fragmentation. This phenomenon may also be sequence specific with arginine and other imino "soft" charge species having a higher likelihood of retaining a charge than other amines (e.g., lysine or histidine residues). In another variation the mass to charge positions associated with higher numbers of charge states may be ignored on a sequence specific basis when determining the total signal associated with any sequence j.

In a variation, multiple labels (both isotopic and nonisotopic) can be incorporated into the algorithm using a dual sequencing approach. In this approach we define two residue tables, one for each label type (an any labeled residues). The sequencing algorithm is then applied using each residue table independently, such that the counts associated with the first label ($c_{i,j,k,l}$) are determined independently from those of a second label ($d_{i,j,k,l}$)

$$c_{i,j,k,l} = LOOKUP[(m/z)_{i,j,k,l}|_{Label1}] \quad (7)$$

$$d_{i,j,k,l} = LOOKUP[(m/z)_{i,j,k,l}|_{Label2}] \quad (8)$$

All the equations 1-6 apply to both c and d, and we can define:

$$q_i = NORMDIST\left[\frac{(D_{i,j} - \overline{D}_i)}{\sigma_i^{label2}}\right] \quad (9)$$

$$\overline{D}_i = \frac{\sum_{j=1}^{19^i} D_{i,j}}{19^i} \quad (10)$$

$$\sigma_i^{label2} = \sqrt{\frac{\sum_{j=1}^{19^i} D_{i,j}^2 - \frac{\left(\sum_{j=1}^{19^i} D_{i,j}\right)^2}{19^i}}{(19^i - 1)}} \quad (11)$$

$$D_{i,j} = \sum_{k=min\ charge\ states}^{max\ charge\ states} \sum_{l=1}^{max\ ion\ types} d_{i,j,k,l} \quad (12)$$

By multiplying the relative probability of each sequence j obtained with each label, we can then obtain a composite ranking for the sequence.

$$R_{j,n} = \prod_{i=1}^{n} (p_i q_i) \text{ or } \sum_{i=1}^{n} (p_i q_i) \quad (9)$$

This variation can be readily extended to more than one label. It is obvious that mass spectrometer files used in this multiple labeling approach can be created by simultaneous fragmentation of a protein sample containing a known mixture of two or more labels. It is equally obvious that mass spectrometer data from separate single label protein fragmentations can be added together to create a virtual multiple label mass spectrometer file for analysis by this method. It is obvious to those skilled in the art that this variation can be used with any type of multiple labeling strategies (supra).

In another preferred embodiment, for isotopic labels, either natural isotopic abundances or with multiple labels of known relative isotopic abundances, the algorithm may be adapted to qualify or rank the peaks of competing sequences by their conformance to the expected abundances of the isotopic series. For example, where two isotopically distinct labels are employed of a known relative abundance, β, the mass to charge ratio of each sequence can be determined for both label isotopes, the corresponding count values determined from the mass spectral data, and a rank or probability of match to the expected abundance (β) determined.

For example, one such way this can be achieved is to take a simple case where a label has been utilized that has two isotopic forms that differ by n mass/charge units and have relative abundances $\beta_1$ and $\beta_2$. A ranking factor, α, can be constructed as a transform of mass fragment count data (raw or transformed) from two isotopic mass fragments such that, $$\alpha = 1 - \{|C_1(\beta_2/\beta_1) - C_2| \div [C_1(\beta_2/\beta_1) + C_2]\} \quad [1]$$

where α, $\beta_1$ and $\beta_2$ are as defined above, and for two isotopic peaks $C_1$=the count data, raw or transformed, for isotopic peak 1
$C_2$=the count data, raw or transformed, for isotopic peak 2

The ranking factor, α, yields a high rank when the counts of each mass fragment pair have a ratio of counts ($C_1/C_2$) that closely matches the ratio of natural abundances for the isotopes chosen, i.e. $\beta_1/\beta_2$. The ranking factor (α) yields a low or poor rank when the mass fragment count ratio differs markedly from the ratio of the relative abundances for the two isotopic mass fragments. Therefore, as the raw count ratio of the isotopic pair approaches the ratio of the isotopic abundances, the isotope ranking factor, a approaches the value of 1. The more the count ratio differs, the lower the rank becomes until α reaches zero.

$$C_1/C_2 \rightarrow \beta_1/\beta_2, \alpha \rightarrow 1 \quad [2]$$

$$\text{and as } C_1 \text{ or } C_2 \rightarrow 0, \alpha \rightarrow 0 \quad [3]$$

In a typical application of the isotope-ranking factor, the difference in mass/charge units and the relative abundance of each isotope is determined. The relative abundance data of each isotope are incorporated into [1]. The isotope ranking algorithm passes through the mass spectral count data (raw or transformed) and evaluates the count size of each mass position relative to the count size of the mass position n mass/charge units away and assigns a rank (a) to the lowest mass fragment of the pair. The ranking factor is then multiplied by the counts of the mass fragment to which it has been assigned and a new count value is produced that has been ranked or scaled based on how well the ratio of the count data match the ratio of the isotopic abundances of the two isotopes. The result is a reduction in counts of peaks that do not have an isotopic match while those that do retain much if not all of their count value. The net effect is a relative increase in signal-to-noise for peaks that have a matching isotope peak downstream as the algorithm passes through the data.

Figure 4:
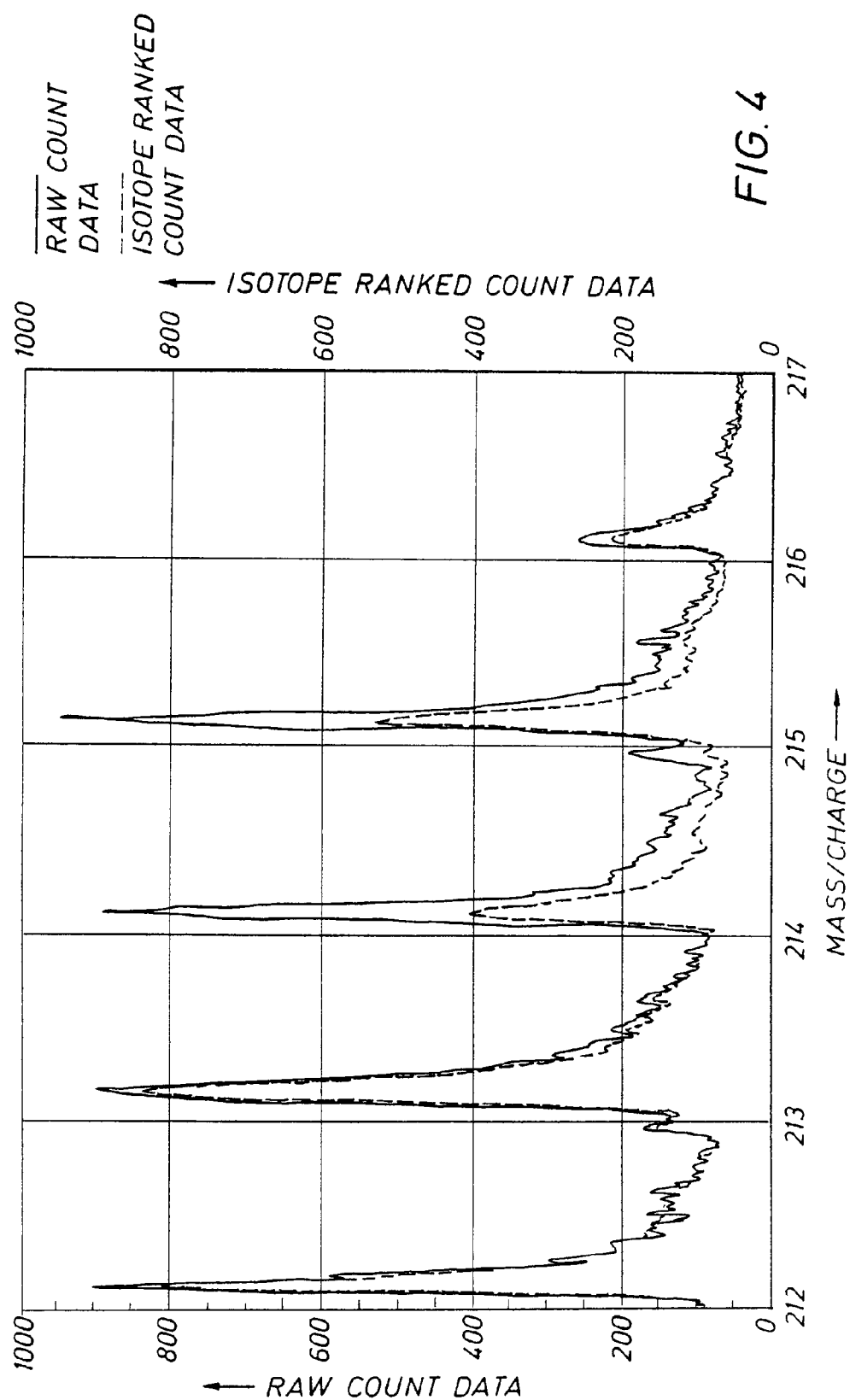
FIG. 4 shows an exemplary comparison of isotope ranked count data to raw count data.

For example, FIG. 4 shows what happens when the isotope ranking algorithm is implemented on data collected from a sample containing two isotopes of an element that differ by approximately 2 mass/charge units, and having relative abundances that are nearly equal. The raw counts near 213 mass/charge units have a nearly equal sized peak that occurs 2 mass/charge units up in mass units, i.e. the peak that occurs near 215 mass/charge units. Therefore the isotope-ranking factor adjusts the count value of the peak at 213 by a small amount that reflects the close fit in response between the peaks near 213 and 215. In contrast, the peak near 214 does not have a matching isotopic peak located 2 mass/charge units downstream that is equal in counts (or isotopic abundance). The raw count value of the peak near 214 is nearly four times that of the peak near 216. Consequently, the isotopic ranking factor is small to reflect the disparity in count sizes, and the peak at 214 gets scaled down in size by a quantitative amount reflective of that difference. Processing an isotopic data file with the isotopic ranking algorithm results in data that has been artificially transformed to yield a higher signal-to-noise ratio for the isotopic mass fragments of interest.

Spectral Noise Reduction Prior to Sequencing

The ability of the sequencing method to determine the true sequence depends on the relative signal strength of the labeled peptide fragments compared to other confounding noise in the mass spectrum. This noise is composed of at least two parts: (1) the offset from baseline produced by residual unfragmented protein and detector noise multicharged ion fragments (FIG. 1) and (2) internal scission fragments that appear at each mass position (FIGS. 2 and 3), particularly at more energetic fragmentation conditions. Since "noise" in a mass spectrum is always positive, in a preferred variation of the method noise reduction approaches may be employed to remove either or both of these "noise" components from the spectrum before applying the sequencing algorithm. In another variation, which is particularly preferred when the method is coupled to a separation method or pulsed sample addition, the Fourier and other time resolved deconvolution techniques may also be employed to reduce the "noise" clutter in the mass spectrum prior to applying the sequencing algorithm.

In one embodiment, autoscaling can be used to help eliminate the baseline shift contribution to the noise. In another embodiment, the noise may be deconvolved from the signal through the development of a deconvolution kernel. This approach is described below. Many other "noise" reduction approaches will be evident to those skilled in the art.

Figure 5:
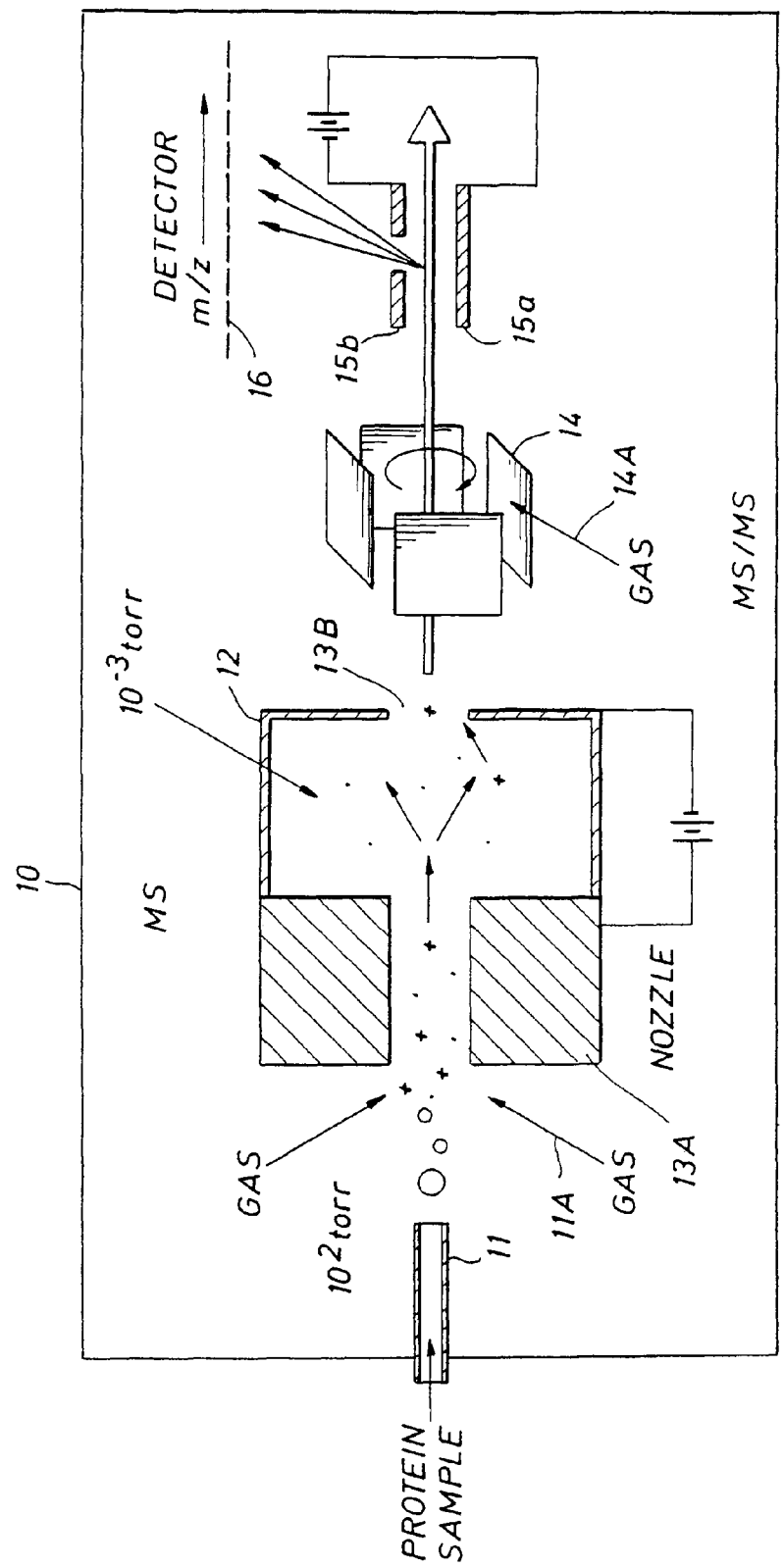
FIG. 5 shows an example of a mass spectrometer which may be used in certain embodiments of the present invention.

FIG. 5 shows an example of a mass spectrometer which may be used to perform the various methods of the present invention. The mass spectrometer includes a capillary 11 which receives a protein sample and which directs the protein sample toward a charged nozzle 13A. The ions in the sample are accelerated between the nozzle 13A and the skimmer 13B. Gas streams 11A may be used to cause an in-source collision induced dissociation in chamber 12 to thereby create charged fragments from the terminal portions of the protein introduced through the capillary 11. With in-source fragmentation, these charged fragments exit the skimmer 13B and are directed through two charge plates 15A and 15B which direct the protein fragments toward a detector plate 16. An optional quadrapole 14 may be used as is well known in the prior art to trap certain ion types and then cause dissociation with a gas stream 14A. The mass spectrometer 10 is typically coupled to a data processing system which processes the data sample obtained by the detector plate 16.

Figure 6:
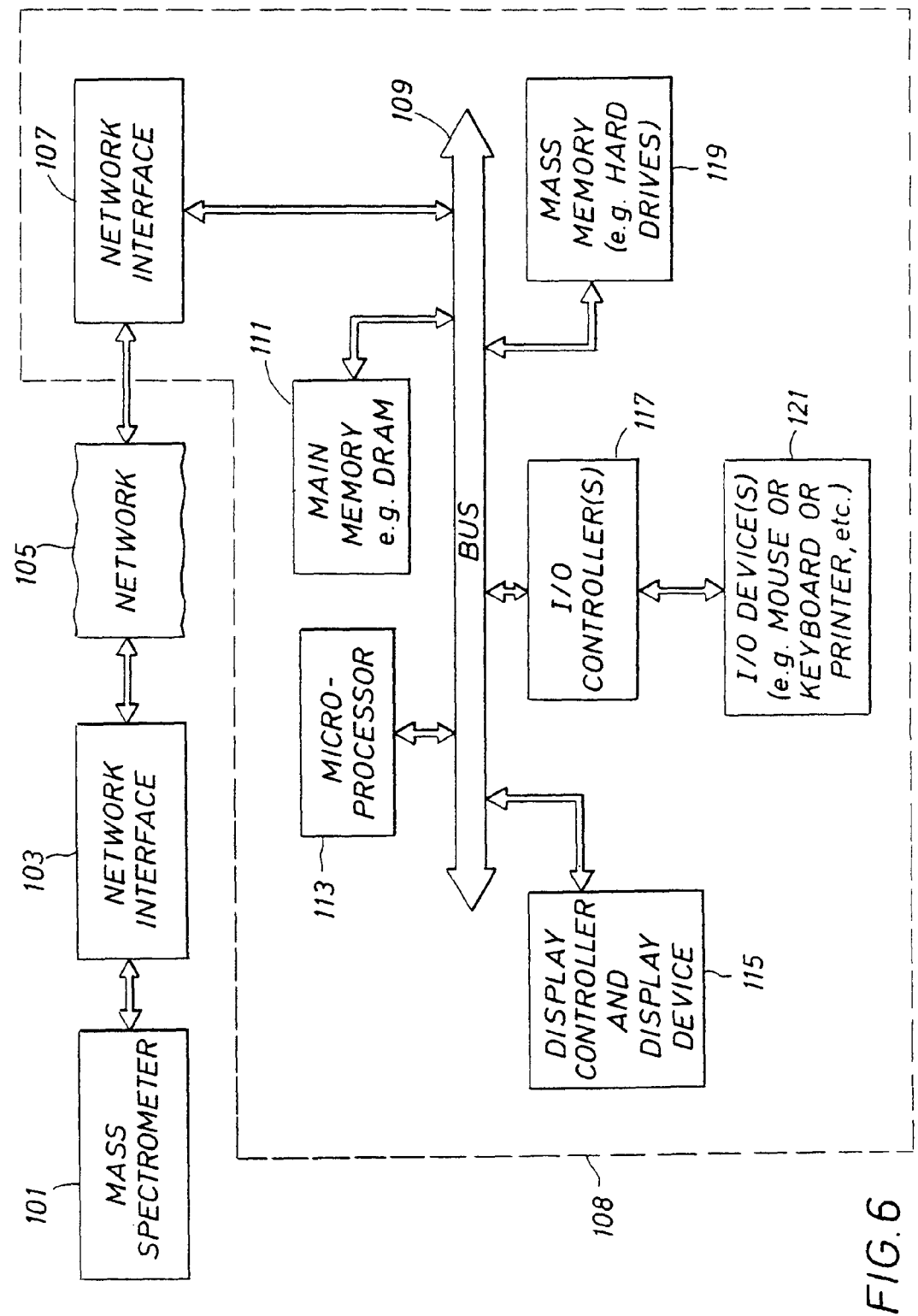
FIG. 6 shows an example of a mass spectrometer which is coupled to a data processing system according to certain embodiments of the present invention.

FIG. 6 shows an example of a data processing system 108 which is coupled to a mass spectrometer 101 through a network 105, which may be the Internet or a local area network such as an Ethernet local area network. The mass spectrometer 101 includes a detector plate 16 which provides data representing the mass spectrum to the network interface device 103 which is coupled to the network 105. This data is transmitted through the network interface 103 and the network 105 to the network interface 107 of the data processing system 108. In turn, the network interface 107 provides this data to the main memory 111 or to the mass memory 119 through the bus 109. The microprocessor 113 then performs various processing methods on this data, such as the processing methods described by the present invention. The processing system 108 may be a typical computer system such as a general purpose digital processing system or a specially programmed processing system which provides the dedicated functions of filtering the mass spectrum data and determining a sequence from that data. Note that while FIG. 6 illustrates various components of a computer system, it is not intended to represent any particular architecture or manner of interconnecting the components as such details are not germane to the present invention. It will also be appreciated that network computers and other data processing systems which have fewer components or perhaps more components may also be used with the present invention. The computer system of FIG. 6 may, for example, be a Unix based workstation.

As shown in FIG. 6, the data processing system 108 includes a bus 109 which is coupled to the microprocessor 113 and to the main memory 111, which may be a dynamic random access memory (DRAM) and a mass memory 119, which may be a magnetic hard drive or a magnetic optical drive or an optical drive or a DVD RAM or other types of memory systems which maintain data even after power is removed from the system. Microprocessor 113 is optionally coupled to a Level 2 (L2) cache which stores data and software for use by the microprocessor 113, and the microprocessor 113 may include an L1 cache on the integrated circuit which is the microprocessor. While FIG. 6 shows that the mass memory 119 is a local device coupled directly to the rest of the components of the data processing system, it will be appreciated that the present invention may utilize a non-volatile memory which is remote from a system, such as a network storage device which is coupled to the data processing system through a network interface such as modem or an Ethernet interface. The bus 109 may include one or more busses connected to each other through various bridges, controllers, and/or adapters as is well known in the art. The bus 109 is also coupled to I/O controllers 117 which support various I/O devices (input/output) 121, such as a mouse, or a keyboard, or a printer, etc. Further, the data processing system includes a display controller and a display device 115 such as a conventional CRT or a liquid crystal display.

It will be apparent from this description that aspects of the present invention may be embodied at least in part in software. That is, the techniques may be carried out in a computer system or other data processing system in response to its processor, such as a microprocessor, executing sequences of computer program instructions contained in a memory, such as main memory 111 and/or mass memory 119 or a remote storage device. In various embodiments, hardwired circuitry may be used in combination with software instructions to implement the present invention. Thus, the techniques are not limited to any specific combination of hardware circuitry and software nor to any particular source for the instructions executed by the data processing system.

Figure 7:
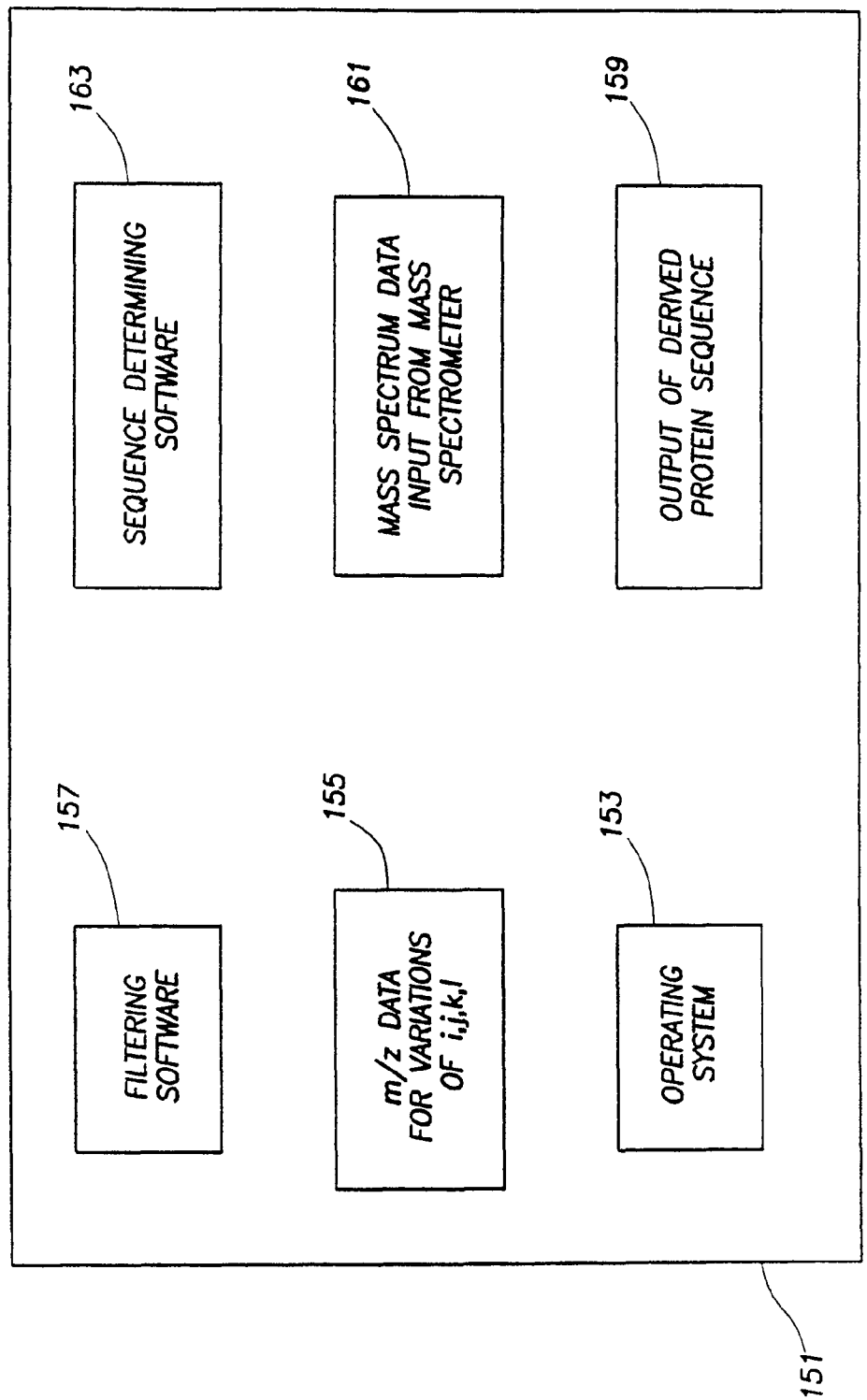
FIG. 7 shows an example of a machine readable media which may be used with certain embodiments of the present invention.
Figure 8:
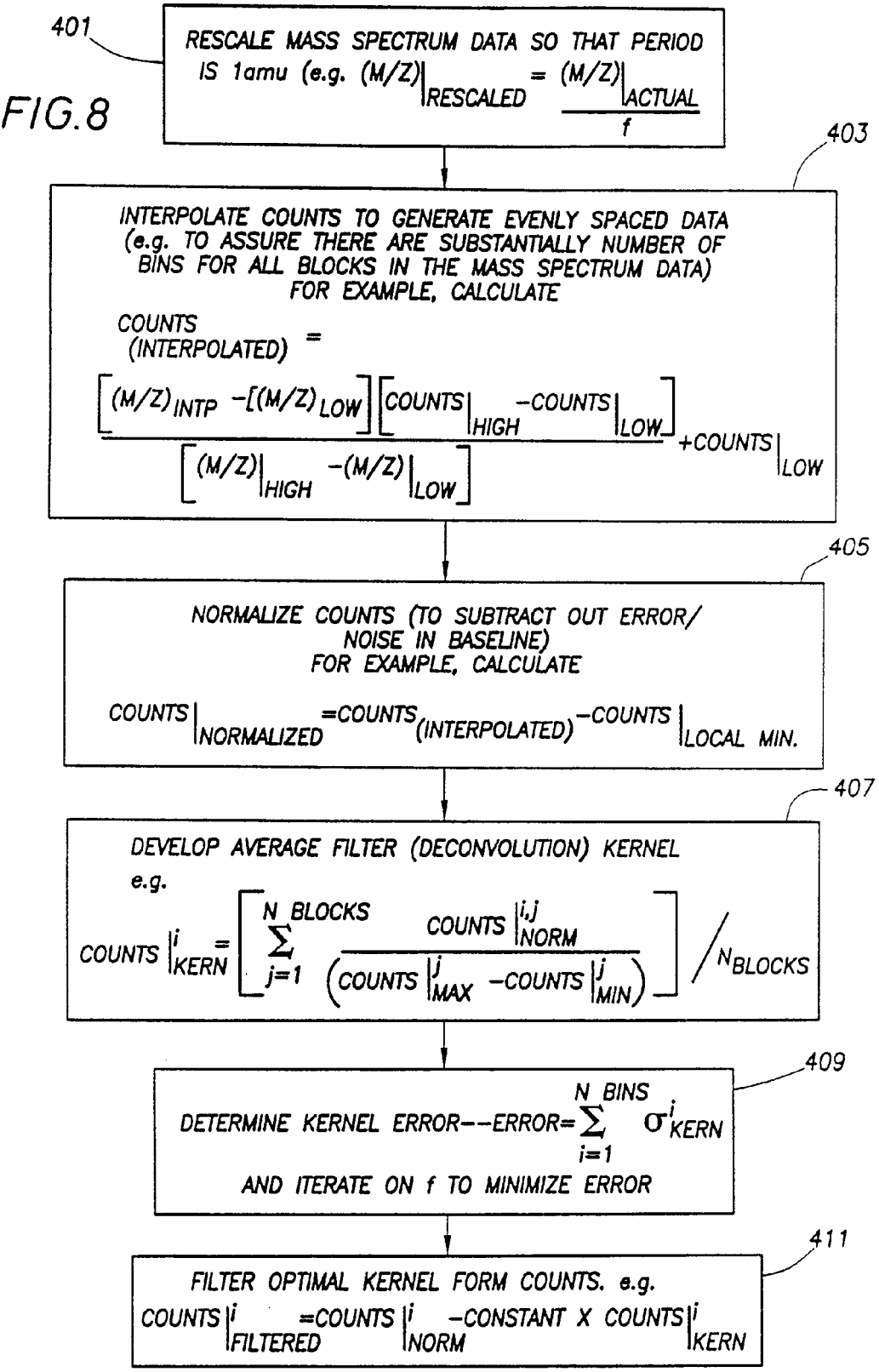
FIG. 8 shows one method according to the present invention for filtering mass spectrum data prior to performing sequencing algorithms according to the present invention.
Figure 9:
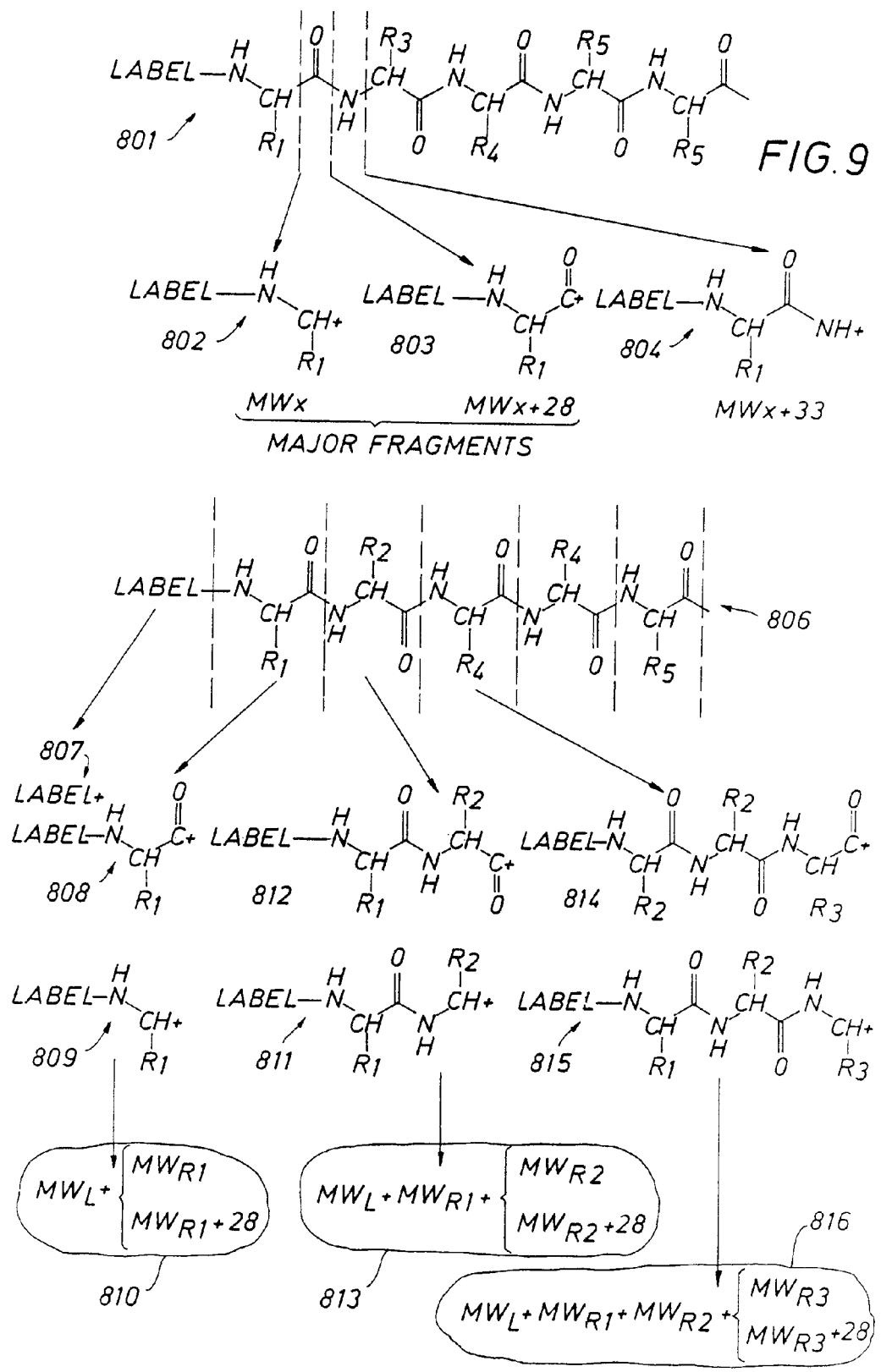
FIG. 9 represents a method for determining ion fragments which may be obtained from terminal portions of a protein or a polypeptide sequence.
Figure 13:
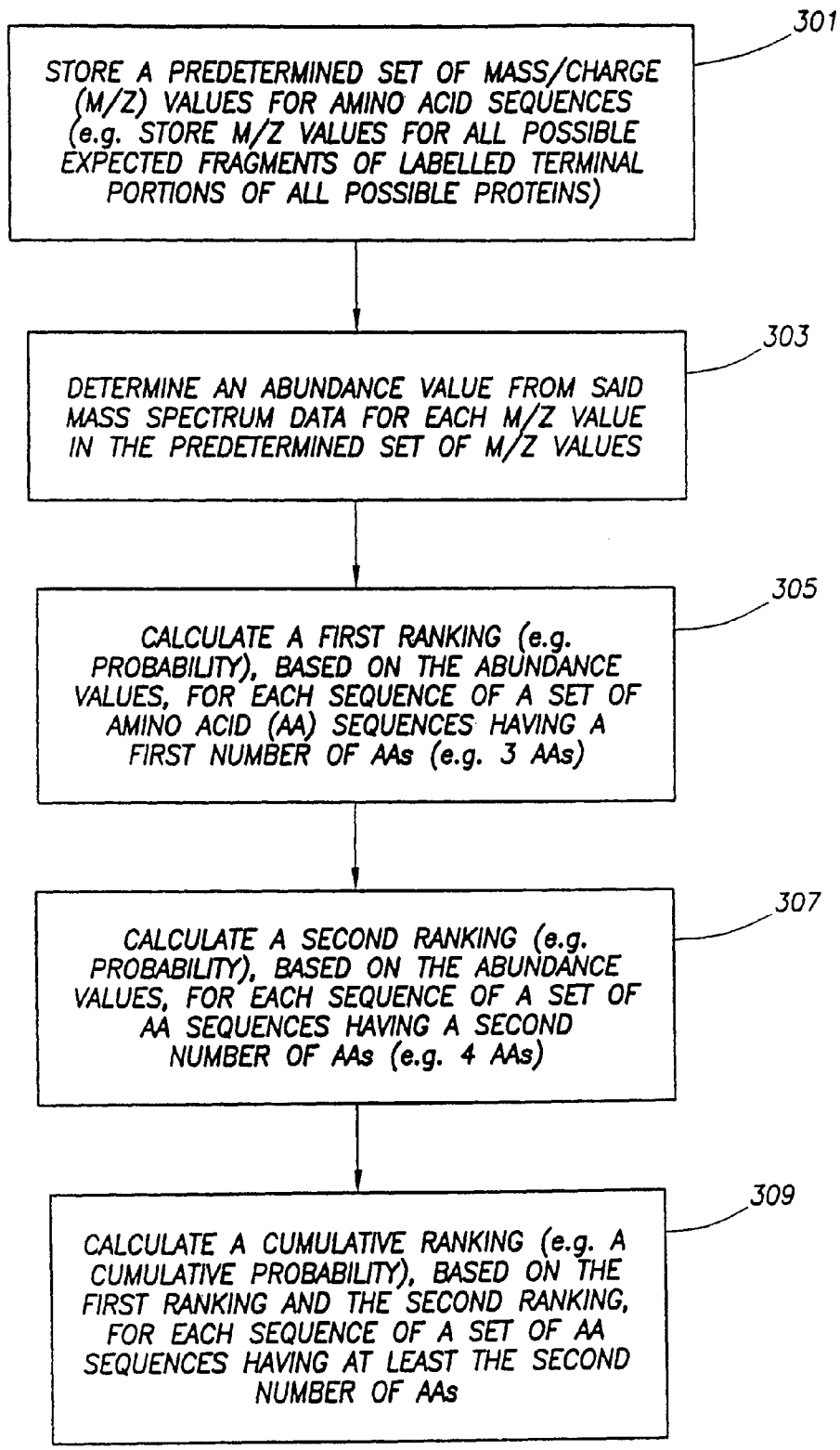
FIG. 13 shows a flowchart illustrating a particular embodiment of the present invention for sequencing a protein.
Figure 14A:
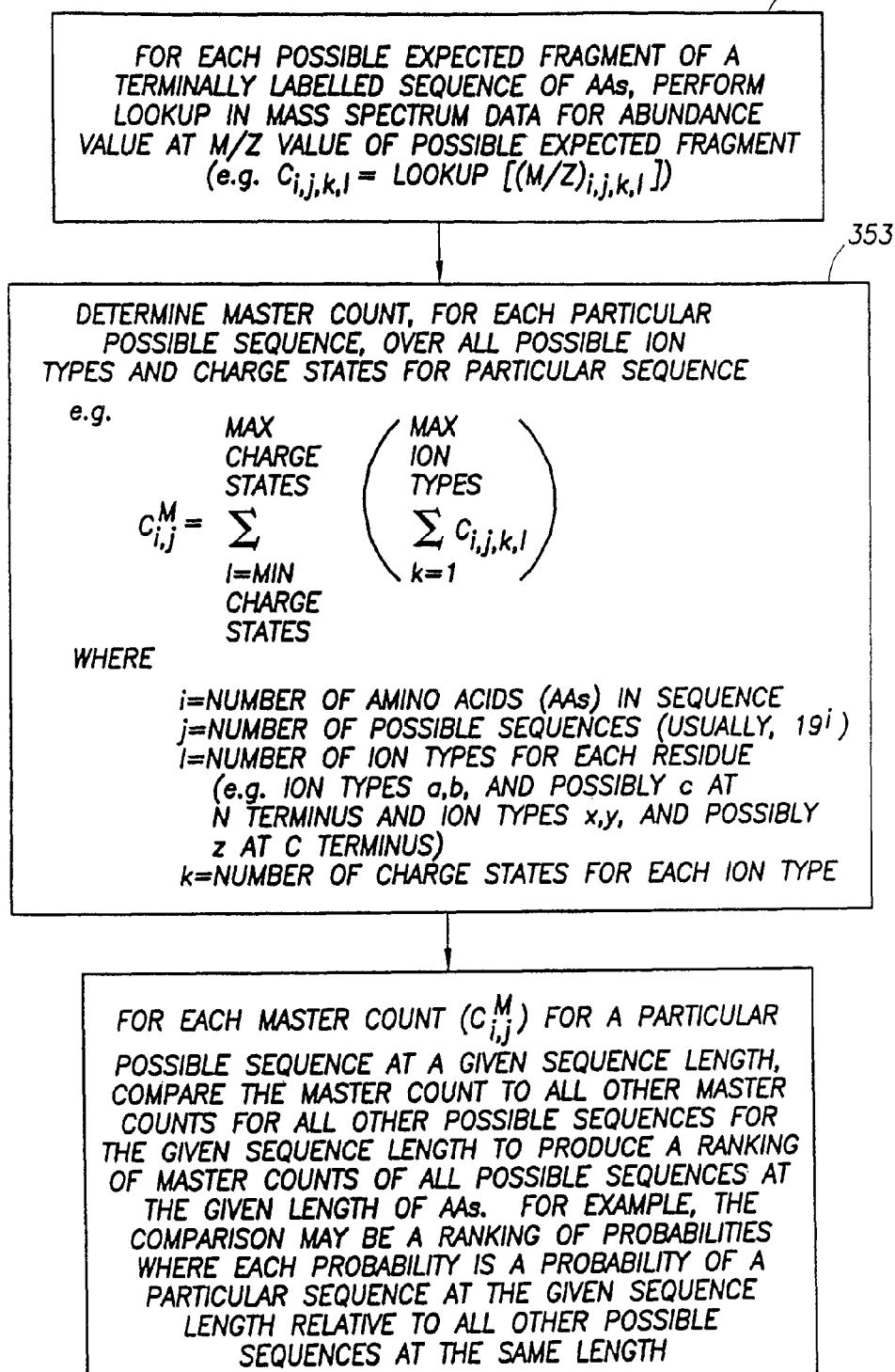

FIG. 7 shows an example of a computer readable media which is a form of a machine readable media, which may be used with the data processing system according to one embodiment of the present invention. The computer readable media contains data and executable software which when executed in the data processing system such as a digital processing system, cause the system to perform the various methods of the present invention. As noted above, this executable software and data may be stored in various places including, for example, the DRAM 111 and/or the mass memory 119 or in a remote data storage device which is coupled to the data processing system through a network interface. Portions of this software and/or data may be stored in any one of these storage devices. The media 151 may be, for example, primarily the DRAM 115 and the mass memory 119 which serves as virtual memory for the data processing system. The operating system 153 may be a Unix operating system or a Windows operating system or a Macintosh operating system as is well known in the art. The optional filtering software 157 includes the executable computer program instructions which filter, in one embodiment, the periodic noise from the mass spectrum data; FIG. 8 shows an example of one method for performing this filtering operation. The sequence determining software 163 includes computer program instructions which perform one of the various methods for determining the sequence of at least a portion of a protein, which is typically a terminal portion of the protein which has been labeled with a mass label. FIGS. 13, 14A, and 18B show examples of the sequencing methods which may be performed by the sequence determining software 163. The m/z data 155 is a set of data which represents a predetermined set of mass/charge values for amino acid sequences such as all possible mass/charge values for all possible expected fragments of labeled terminal portions of all possible proteins. This data may be determined both theoretically and empirically. FIG. 9 shows an example of the various possible expected fragments of labeled terminal portions of all possible proteins. This data is used in one embodiment in conjunction with the mass spectrum data 161 which is inputted from a mass spectrometer. As an alternative to storing all the necessary m/z data (e.g. as data 155), one embodiment of the invention determines the necessary m/z data on the fly (on an as-needed basis). that is, for each sequence which is to be looked up in the mass spectrum data (e.g. a lookup operation 351 of FIG. 14A), a processor determines, on an as-needed basis, all possible m/z data values for the given sequence (e.g. Label -Ala or Label -Ala-Tyr) including the "basic" molecular weight (MW) of the sequence and MWs for the various different ion types (e.g. a or b or x or y) and MWs for the various different charge states. This alternative is described further below in conjunction with FIG. 18.

In a typical embodiment which uses the computer readable medium of FIG. 7, the filtering software 157 performs a filtering operation on the mass spectrum data 161 to obtain filtered data. This filtered data is then processed by the sequence determining software 163 to derive an output of the protein sequence which is stored as the data 159.

Figure 10:
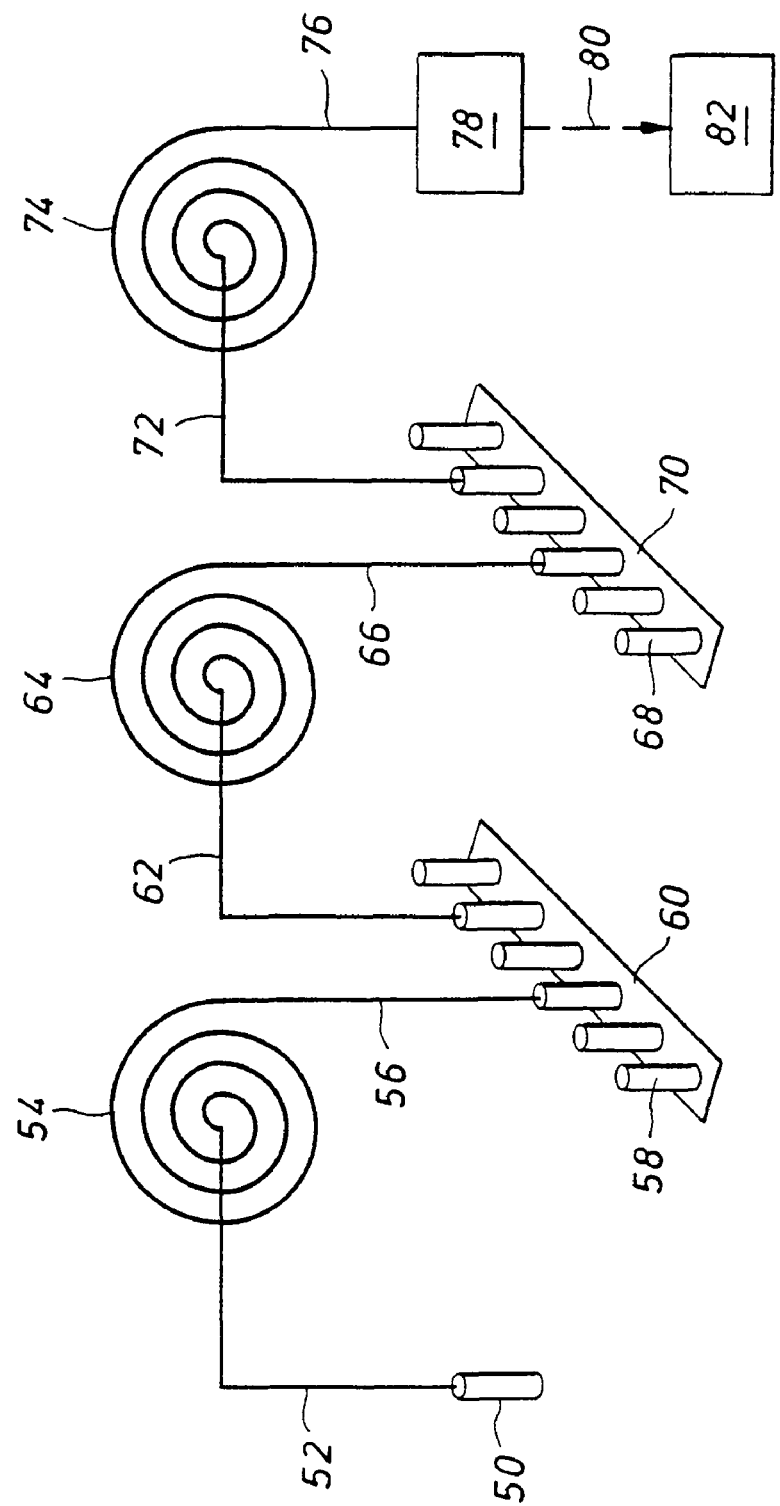
FIG. 10 shows an example of a separation method for separating several proteins in order to obtain isolated protein samples from a collection of proteins such as a cellular extract.

FIG. 10 shows an example of a system utilized with certain methods of the invention for isolating proteins. In one embodiment of the invention, a tissue extract from a biological material is obtained, and this tissue extract contains many proteins (e.g. from 100 to over 1,000 proteins). These proteins are separated so that a mass spectrometer can analyze each separated protein by itself. The particular example shown in FIG. 10 uses three independent methods (initial, intermediate, and final methods). The particular types and number of methods conducted can vary, although most typically, at least one electrophoretic separation method is used. The various methods which may be utilized in the system shown in FIG. 10 are further described in co-pending U.S. patent application Ser. No. 09/513,486 which was filed Feb. 25, 2000 and is entitled "Protein Separation Via Multi-Dimensional Electrophoresis," which application is hereby incorporated herein by reference. Other chromatography methods, such as reverse phase HPLC or size exclusion may be optionally used.

Figure 11:
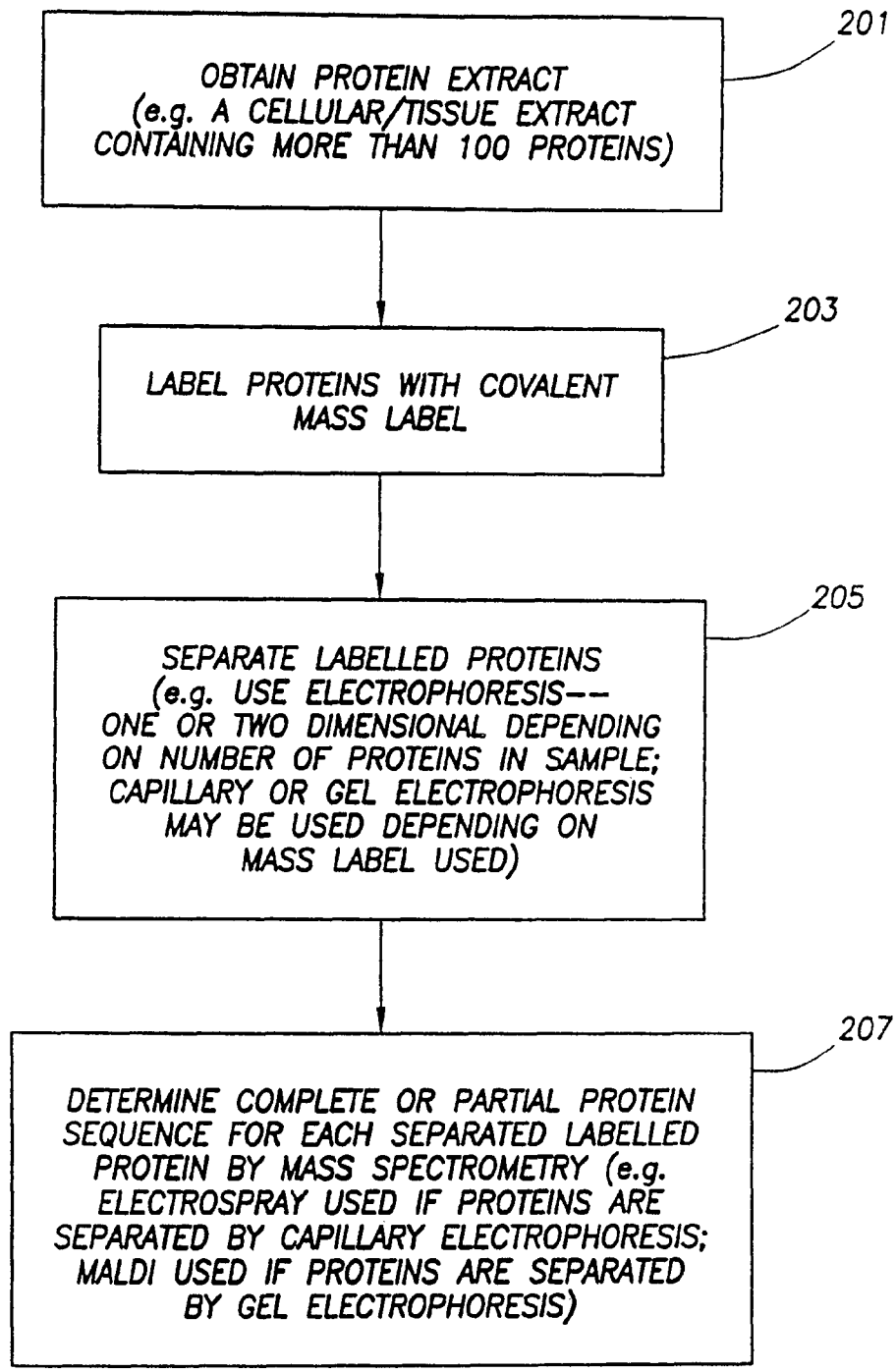
FIG. 11 shows a flowchart showing an overview according to one embodiment of the present invention.

FIG. 11 shows a general overview of certain embodiments of the present invention. Operation 201 represents the typical beginning of a method in which a cellular or tissue extract is obtained, where this extract contains more than 100 proteins. These proteins are labeled with a covalent mass label 203, such as the mass labels described above. These mass labels are typically designed to provide a unique mass which can be used to impart a unique mass signature to the fragments to which they are attached. In operation 205, the labeled proteins are separated. There are various conventional techniques which may be used, such as electrophoresis, to perform this separation operation. FIG. 10 shows a particular example of a separation operation. Then operation 207 determines the complete or partial protein sequence for each separated, labeled protein by performing mass spectrometry to obtain a mass spectrum data, such as the sample shown in FIG. 1.

Figure 12:
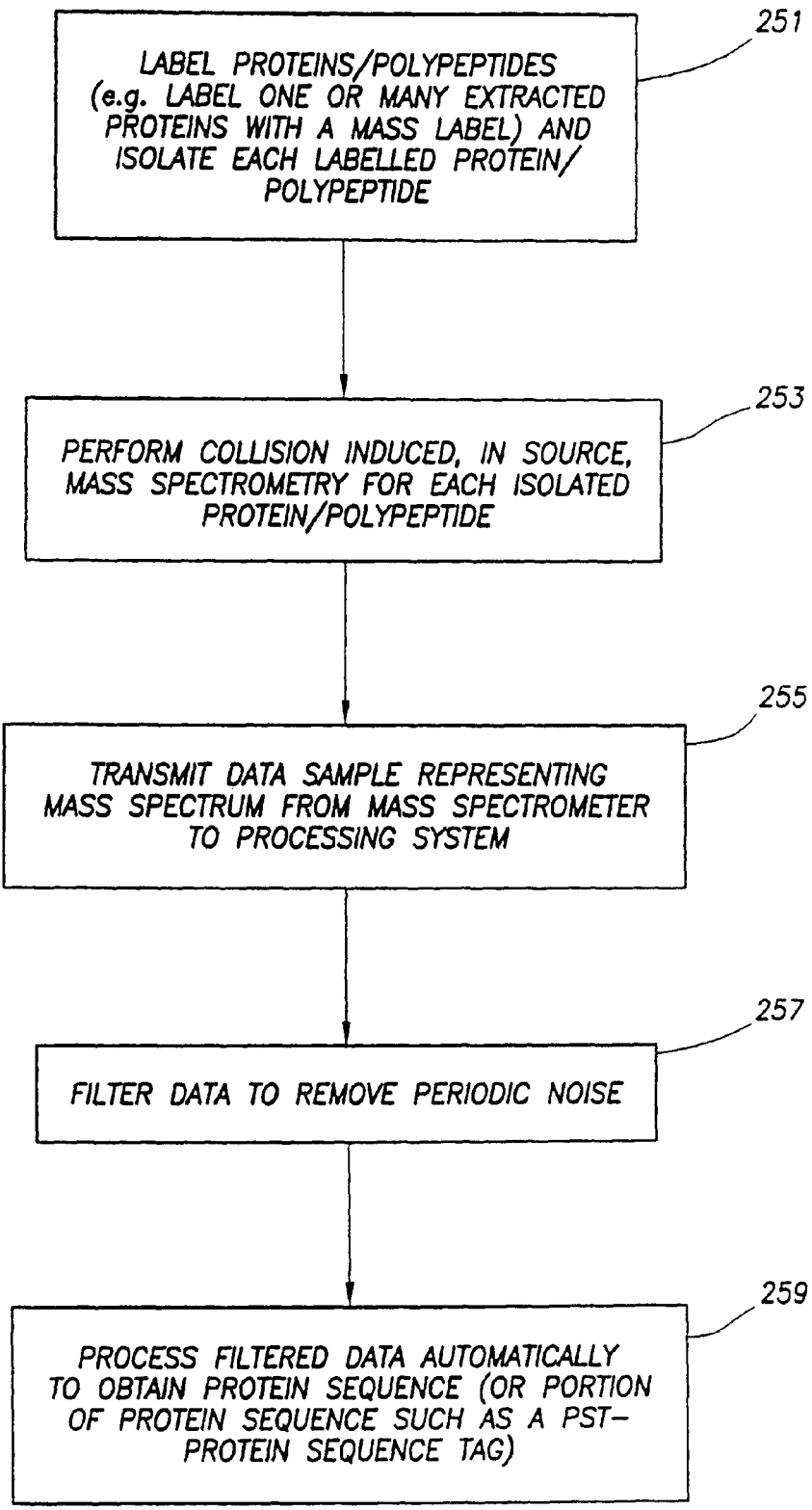
FIG. 12 shows a more particular example according to one embodiment of the present invention.

FIG. 12 shows a more particular example according to certain embodiments of the present invention in order to determine a protein sequence. Operation 251 labels the proteins or polypeptides and isolates each labeled protein or polypeptide. Operation 253 performs collision induced in source mass spectrometry for each isolated protein which has been labeled. Then the resulting mass spectrum data sample is transmitted from the mass spectrometer to a data processing system in operation 255. The mass spectrum data is filtered to remove periodic noise in operation 257. An example of a filtering method which may be used in operation 257 is shown in FIG. 8. Finally, as shown in FIG. 12, operation 259 processes the filtered data on a data processing system to obtain at least a portion of a protein sequence such as a protein sequence tag which may be used to infer the complete protein sequence. As is known in the art, if a 4 or 5 amino acid tag can be identified at a terminal portion of a protein, it is then possible to infer the complete protein sequence from the existing protein databases.

FIG. 9 illustrates how to determine a set of mass/charge values for amino acid sequences. This is shown as operation 301 in FIG. 13. The N-terminus portion 801 of a protein or polypeptide typically produces three fragments 802, 803, and 804 in a collision induced dissociation performed according to certain embodiments of the present invention. Each of these fragments 802, 803, and 804 includes a mass label such as the mass labels described above. The various different fragments which may be obtained from the first three residues of the N-terminus of the polypeptide 806 are also shown in FIG. 9. In particular, the first residue primarily produces fragments 807, 808, and 809, where the fragments 808 and 809 have the masses shown as 810. Fragments 811 and 812 represent the primary fragments generated from collision induced dissociation for a fragment that contains two amino acids/residues. These fragments 811 and 812 have the masses shown as 813. For those fragments having three amino acid residues, there are two primary fragments 814 and 815 which have the masses shown as 816. These mass/charge values are used to determine the predetermined set which is used in operation 301 in FIG. 13.

FIG. 13 shows one particular method according to one embodiment of the present invention for determining a sequence of amino acids, such as a terminally labeled portion of a protein. Operation 301 determines and optionally stores a predetermined set of mass/charge values. This typically involves determining and/or storing all possible mass/charge values for all possible expected fragments of the labeled terminal portions of all possible proteins. FIG. 9 shows an example for fragments having lengths of one amino acid, two amino acids, and three amino acids. It is noted that the expected fragments may be a subset of all possible fragments due to the fact that certain fragments are not found in appreciable quantities in empirical tests. Operation 303 involves a lookup wherein an abundance value is determined from the mass spectrum data for each mass/charge value in the predetermined set of mass/charge values. Next, in operation 305, a first ranking, such as a probability, is calculated based on the abundance values for each sequence of a set of amino acid sequences having a first number of amino acids. Operations 357 and 359 shown in FIGS. 14A and 14B respectively, represent one particular method for performing the operation 305. Operation 307 calculates a second ranking, such as a probability, based on the abundance values for each sequence of a set of amino acid sequences having a second number of amino acids. It will be appreciated that typically the second number is different than the first number. Operation 357 and 359 show a particular embodiment for calculating the second ranking when the number of amino acids in the sequence is the second number of amino acids. After operation 307, a cumulative ranking is performed in operation 309. This cumulative ranking is based upon both the first ranking and the second ranking and is done for each sequence of a set of amino acid sequences having at least the second number of amino acids. Operation 361 of FIG. 14B shows an example of a method for performing cumulative ranking. The results of the cumulative ranking may be evaluated to determine the most likely sequence which has the highest ranking (e.g. a cumulative probability). It will be appreciated that other methods may be taken in to account to corroborate the sequence determined as a result of the cumulative ranking. For example, electrophoresis data which specifies certain parameters of the protein may be compared against the determined sequence or determined protein in order to corroborate the sequence determination resulting from the cumulative ranking.

FIGS. 14A and 14B show a particular computational method according to an embodiment of the present invention. Operation 351 includes the lookup operation described in operation 303. This lookup would typically be performed for each mass/charge value in the predetermined set stored in operation 301. Because each fragment may include different ion types and different charge states, a master count is determined in operation 353 for each particular sequence. This master count is then used for each particular possible sequence at a given sequence length in the operations 357 and 359 which are used to perform the first and second rankings of FIG. 13. Then a cumulative ranking is performed in operation 361 and a sequence may be selected with the highest cumulative ranking in operation 363.

FIG. 15 shows an example of the use of multiple labels according to one embodiment of the present invention. For example, operations 1101, 1103, 1105, 1107, 1109, and 1111 are similar to the methods shown in FIGS. 14A and 14B for one label. Operations 1121, 1123, 1125, 1127, 1129, and 1131 are similar to operations shown in FIGS. 14A and 14B but they are performed for a different label (shown as label 2 in FIG. 15). A resulting cumulative ranking or probability for both labels may then be calculated in operation 1135, and the highest probability sequence may be determined from the list of probabilities derived from the operation 1135.

FIG. 8 shows a particular method for filtering the mass spectrum data prior to attempting to determine the sequence from the mass spectrum data, and this method will now be described with reference to FIGS. 2, 3, 16 and 17.

The mass spectrum (FIG. 2) is basically the number of ions (Counts) that strike a detector plate. The time at which the ions strike the detector plate determines the mass to charge (m/z) ratio of the ion striking the plate. The detector plate is calibrated with known m/z molecules before an unknown is run. Each time period on the detector plate is then assigned an average m/z value and collects ions with m/z ratios of a defined range in sizes.

The size range covered by each detector bin varies as the square root of the m/z value of the bin (about 0.000707 amu0.5). This means that the absolute mass precision of decreases with increasing m/z in the mass spectrometer. It is important to note that noise in a mass spectrometer is always positive. Therefore, the signal is always≧zero in each bin. This gives rise to a built in "feature" of the MS software that compresses the datafile by removing any zero count data that falls within a string of zero count data bigger than 3 consecutive zero counts long. Hence, we have incorporated a piece of code that reinserts these zeros. This is only an issue when datafiles are being added or subtracted from one another. Since bin calibrations can drift between runs, it is important to align the datafiles with a bin then perform the union operation with each aligned bin in the series.

A more detailed look at a sample mass spectrum (FIG. 2) shows that the "noise" is not random. There is an approximately 1 amu periodicity to the spectral noise. This "noise" is only apparent at higher nozzle potentials (increasing fragmentation conditions).

The spacing of this "noise" is slightly larger than 1 amu—as is evident from a overlay of all the peaks in the spectrum on a 1 amu spacing (FIG. 3)—and varies slightly from protein to protein. Since the mass spectrum is calibrated based on a carbon=12.000000 amu standard and the scaling factor varies from protein to protein, we suspect that the slight offset is due to the amino acid composition in the protein (differences in hydrogens, nitrogens, oxygens, and sulfurs).

The spacing between peaks, however, is constant. Therefore, it is possible to rescale the data to match a perfect 1 amu spacing by dividing the m/z values through by a scaling factor. The optimum rescaling factor (f) appears to vary from protein to protein.

It is this characteristic peak shape in the "noise" that we need to deconvolve or filter from the mass spec datafile. In order to define a characteristic peak shape (deconvolution kernel) and subtract this from the rest of the datafile, it is necessary to make the data evenly spaced in the m/z domain. To do this we define a starting m/z and increment the m/z by a constant value until it hits an ending m/z value. The best precision of our current MS is at the low end of the m/z range and is about 0.01 amu. Therefore, we believe that the spacing should be ≦0.01 amu. We showed that there is negligible difference in the sequencing results between 0.01 and 0.001 amu spacings, so 0.01 amu would appear to be close to the best value to use. Smaller spacings dramatically increase the datafile size and sequencing speed.

Once a m/z value is calculated, the Counts associated with that m/z value are obtained by linear interpolation between the closest adjacent values (bracketing that m/z) in the original datafile.

$$\text{Counts}|_{new} = \frac{(m/z_{new} - m/z_{low}) \times (\text{Counts}|_{high} - \text{Counts}|_{low})}{(m/z_{high} - m/z_{low})} + \text{Counts}|_{low}$$

It is possible that better interpolation results might be obtained using a nonlinear interpolation method based on the characteristic peak shape.

Some obvious characteristics of the MS datafile (FIGS. 1 and 2) are the shifting baseline. The baseline shift primarily appears to be due to the presence of unfragmented protein and/or larger protein fragments. Since the sequencing algorithm ranks sequence alternatives based on their relative peak heights, it is desirable to remove background shifts in the baselines. It can be noted in the mass spectrum that there are both long range baseline shifts and shorter range shifts.

Again, the intrinsic periodicity in the data is used to normalize the Count data. To do this we first find the local minimum and maximum counts within a each 1 amu block of MS data. We then subtract the local minimum from each Count value within the same 1 amu block to pull each peak back to a zero baseline. Again, it may be better to define a minimum based on the characteristic peak shape rather than a single value to avoid random noise issues, particularly for smaller peaks.

Once the datafile is normalized it is possible to determine the characteristic peak shape, which will become the deconvolution kernel. Since each peak has a different height (even after baseline correction), it is necessary to rescale the Count data within each 1 amu block between the minimum and maximum values. Starting from the normalized data this is accomplished by:

$$Kernel_i = \frac{\sum_{j\ blocks} \frac{\text{Normalized } Counts_{i,j}}{(Counts_j^{Max} - Counts_j^{Min})}}{\text{total \# of blocks}}$$

FIG. 16 shows the shape of the average deconvolution kernel determined as a function of the strength of the protein fragmentation conditions (nozzle potential).

Obviously, the average kernel shape depends on the factor used for rescaling the data. We optimize the scaling factor by minimizing the sum of standard deviations (Error) over all the bins of the kernel.

$$Error = \sum_{i\ bins} \sqrt{\frac{\sum_{j\ blocks}\left[\frac{\text{Normalized } Counts_{i,j}}{(Counts_j^{Max} - Counts_j^{Min})}\right]^2 - \frac{\left[\sum_{j\ blocks} \frac{\text{Normalized } Counts_{i,j}}{(Counts_j^{Max} - Counts_j^{Min})}\right]^2}{\text{total \# of blocks}}}{(\text{total \# of blocks} - 1)}}$$

Figure 17:
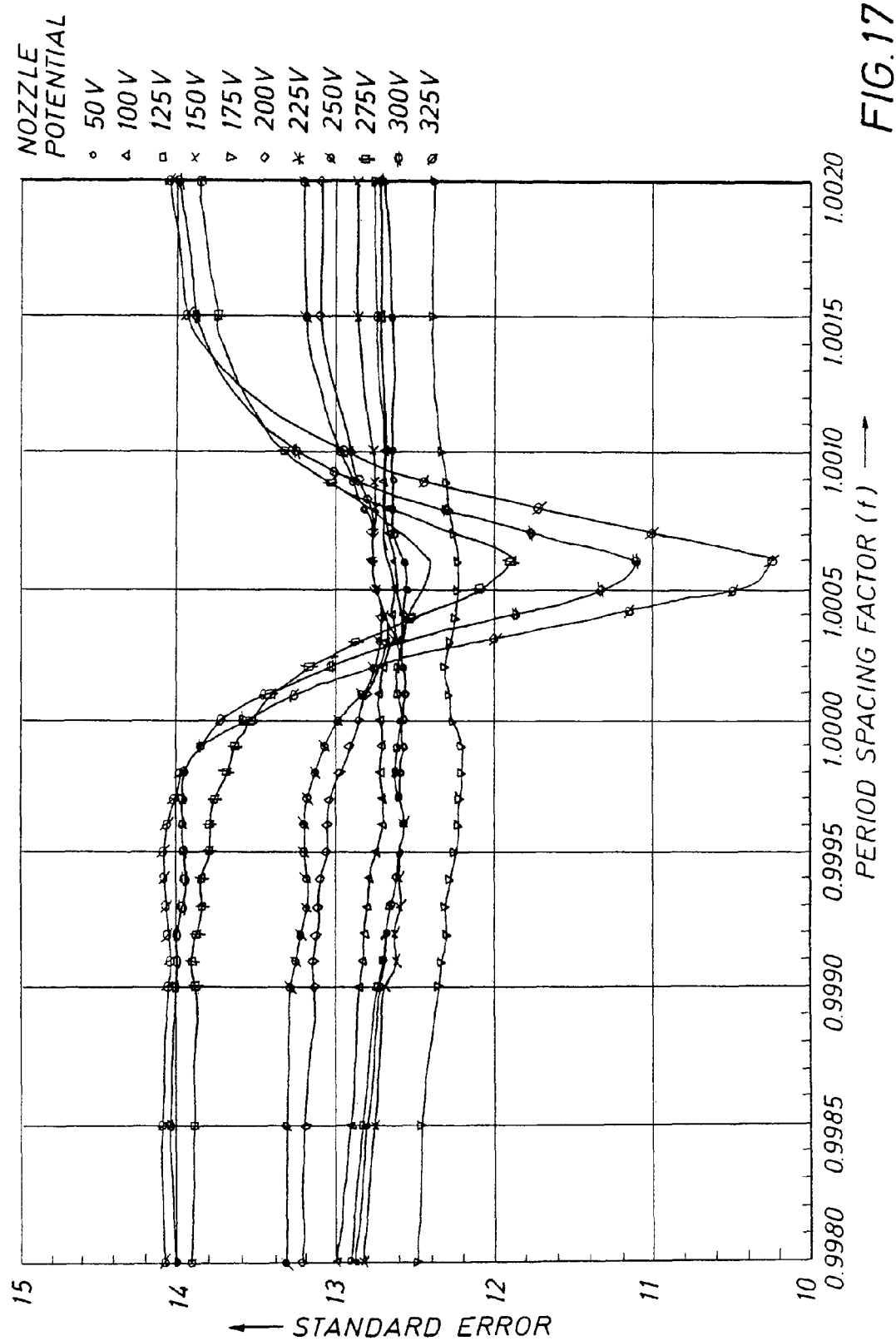

We have tried two approaches to determine the optimum scaling factor: bisection and Newton-Raphson methods. The bisection approach appears to hone in on the optimum scaling factor more robustly than the Newton-Raphson method. There appears to be lots of shallow local minima that causes the Newton-Raphson method to get trapped. Fortunately, the global minima appears to be very sharp at the higher fragmentation conditions (nozzle potentials) that are of the most concern (FIG. 17).

Figure 18A:
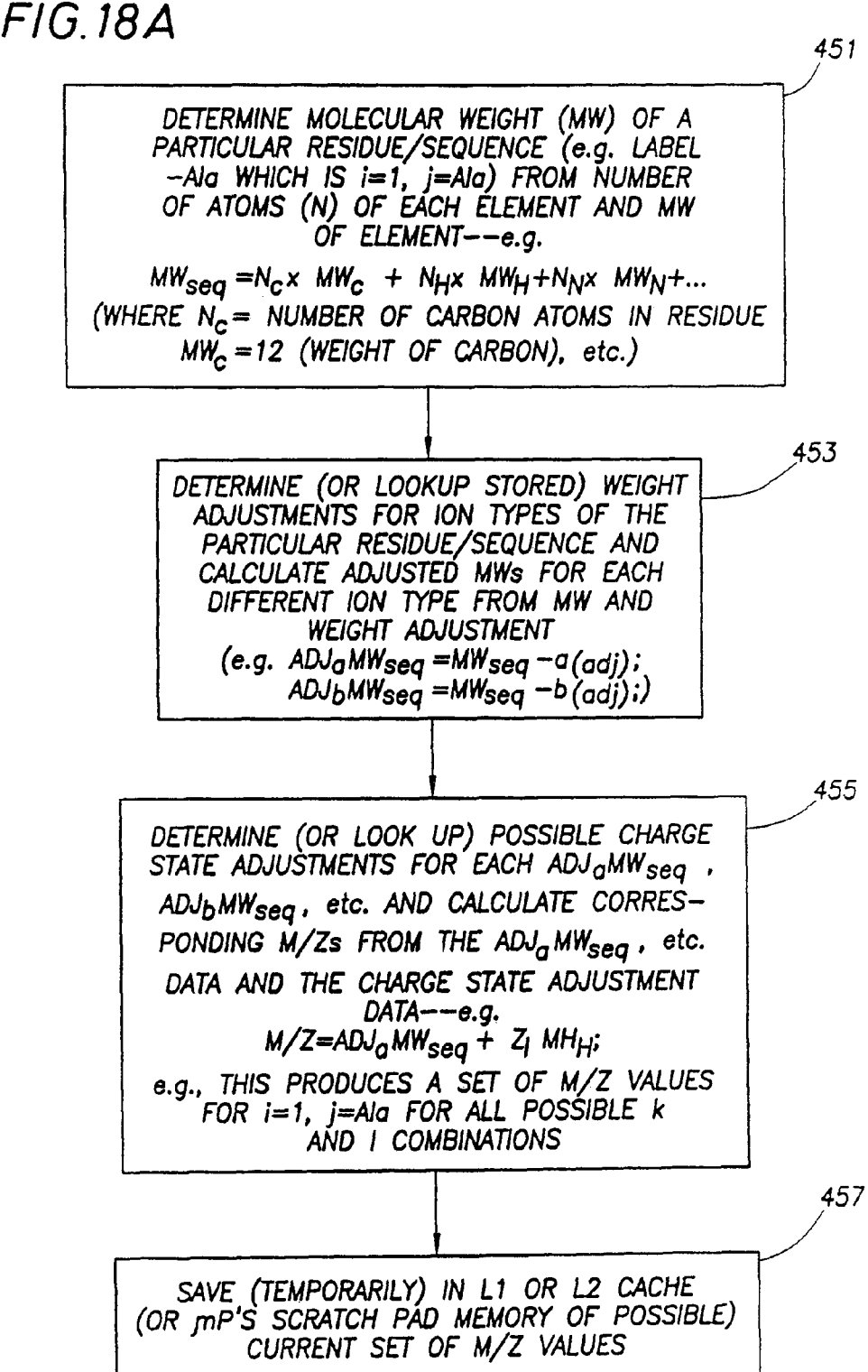
FIGS. 18A and 18B illustrate an example according to one embodiment of a computational method in which a set of m/z values are calculated on an as-needed basis rather than being stored and retrieved from a storage device to a bus.
Figure 18B:
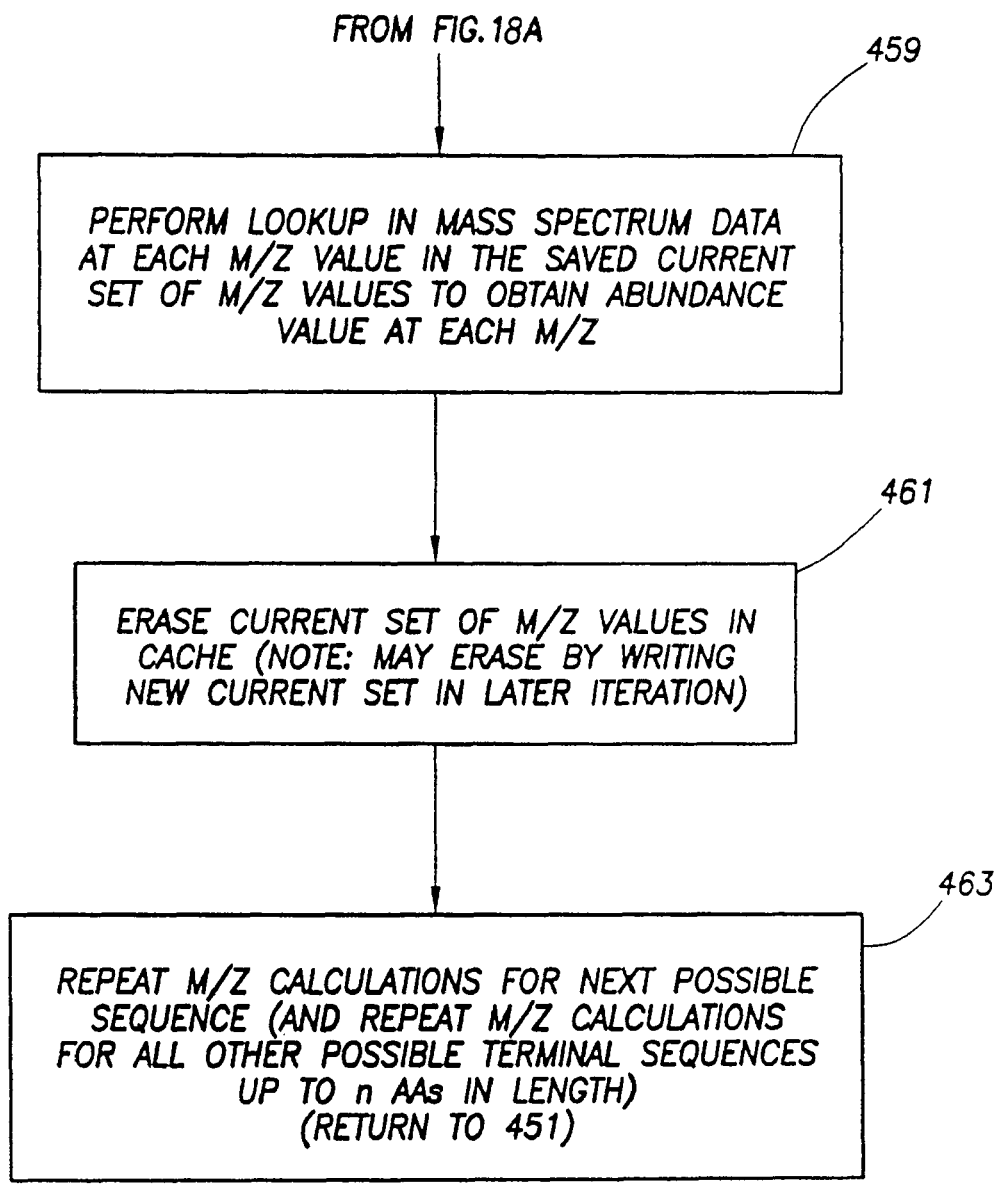

FIGS. 18A and 18B show a particular computational method in which, according to a preferred embodiment, the entire mass spectrum data is loaded into an L2 cache of a microprocessor and only the necessary values of the set of the m/z values are calculated and used on an as-needed basis and stored in the L2 cache. This is done to avoid accessing a large data file which would contain all possible m/z values. It has been determined that storing all possible m/z values in RAM or a hard drive would require over 20 gigabytes of storage space. Accessing such a data file in a hard drive and over a computer's bus takes considerably more time than calculating on an as-needed basis the m/z values in order to perform the lookup operations as described herein. Accordingly, the methods shown in FIGS. 18A and 18B calculate the molecular weight of a particular residue sequence on an as-needed basis by computing a basic molecular rate value for the particular sequence and then adjusting the weight by using a weight adjustment factor as shown in operation 453 and by adjusting the weight with charge state adjustments in operation 455 to derive a complete set for the current sequence which is then temporarily saved in operation 457 in an L2 or L1 cache. Then a lookup operation is performed in operation 459 by using the just calculated tm/z values to lookup into the mass spectrum data in the L2 cache the abundance values for the corresponding m/z values. Then in operation 461, the current set of m/z values is erased now or in a subsequent iteration by writing new current m/z data. Operation 463 follows in which the m/z calculations for the next possible sequence are performed in order to perform the lookup operations associated with those m/z values. Thus, rather than storing all possible m/z values in a hard drive or in main memory (e.g. DRAM), the values are calculated on an as-needed basis and stored temporarily in the L2 cache. These operations are repeated for all possible terminal sequences up to a desired length of amino acids, such as 7 amino acids. Thus the operation from operation 463 returns back to operation 451 for each subsequent sequence up to a given length of amino acids.

The methods shown in FIGS. 18A and 18B greatly increase the speed of the computation overall, even though the microprocessor must perform the necessary m/z calculations repeatedly rather than retrieving previously calculated values from a storage device.

Figure 19:
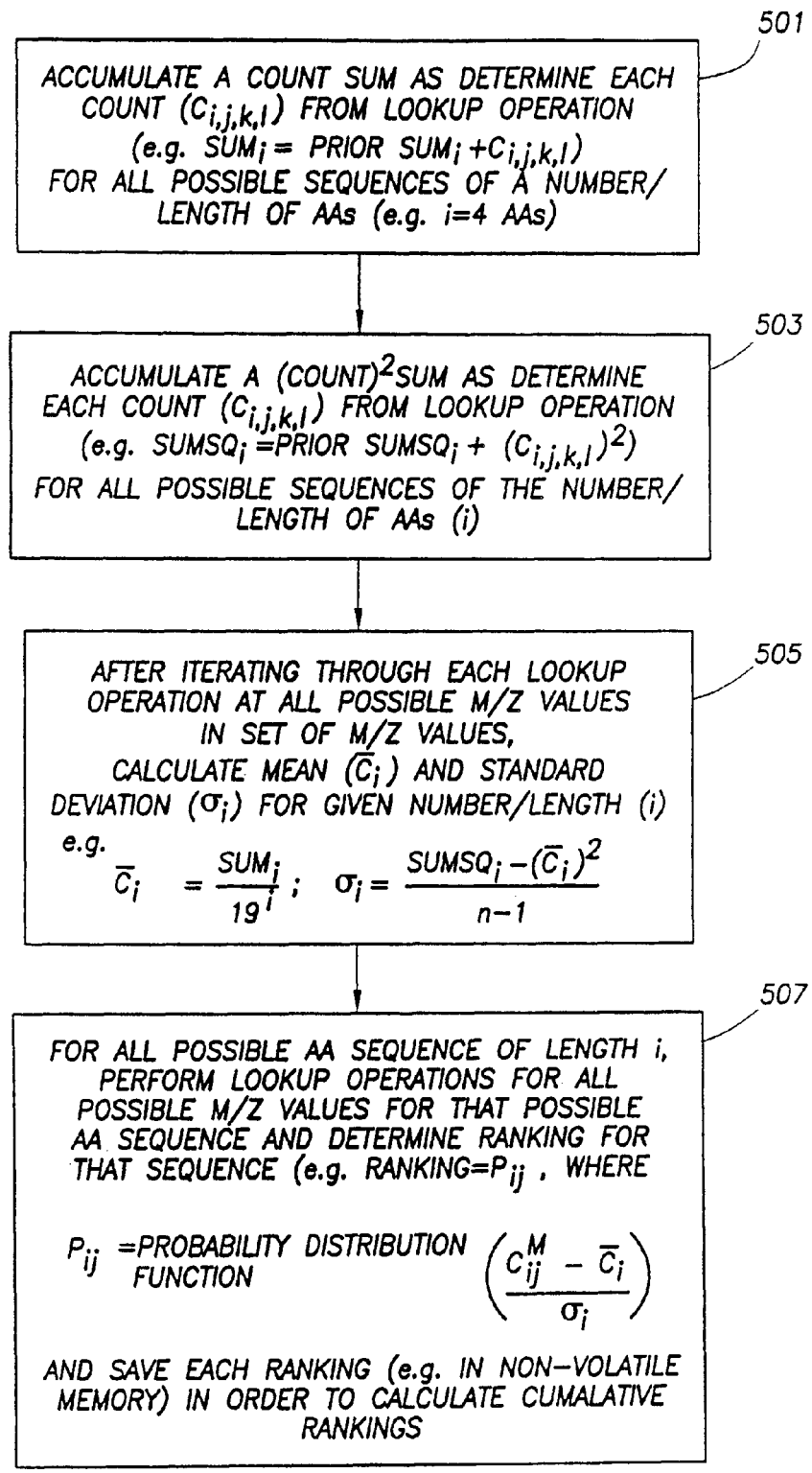
FIG. 19 shows another embodiment of a computational method according to the present invention in which count data is obtained from the mass spectrum directly from a cache of a microprocessor rather than from main memory or from a hard drive.

FIG. 19 shows a method for minimizing the storage required for the intermediate results. In this method, the m/z values are used twice to retrieve the abundance values in two different lookup operations. Thus, the operations depicted in FIGS. 18A and 18B would be repeated twice for both sets of lookup operations.

The first set of lookup operations is performed in operations 501 and 503 in which a count sum and a count squared sum are accumulated. It can be seen that these values can be stored in an L2 cache as there will only be 4 sum values in the case when the maximum length is 4 amino acids and 4 sum squared values. After iterating through each lookup operation for all possible m/z values, operation 505 computes the mean standard deviation which is then used in operation 507 to determine the ranking. Operation 507 is the second pass through the lookup operations, again computing the m/z values on the fly on an as-needed basis as shown in FIGS. 18A and 18B in a preferred embodiment. The ranking for each possible sequence is saved in order to calculate the cumulative rankings as described above.

Figure 20A:
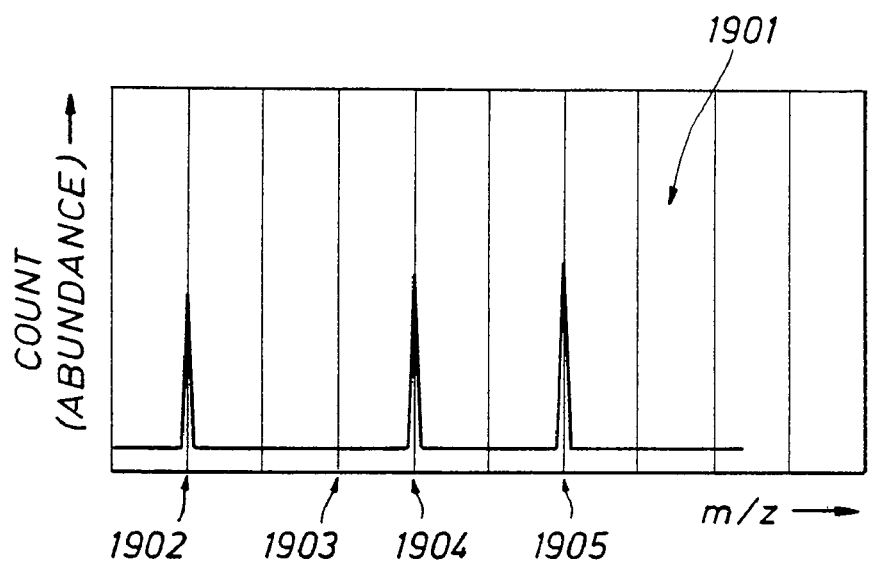
FIGS. 20A and 20B illustrate another filtering technique for filtering mass spectrum data, which technique may be used in conjunction with multiple labels.
Figure 20B:
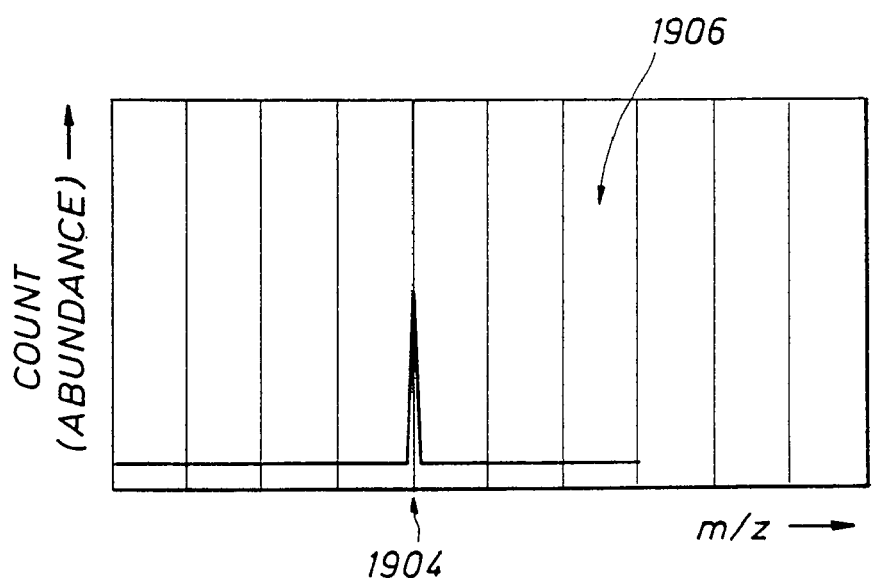

FIGS. 20A and 20B represent a technique for using multiple labels to provide doublets which can be used to remove noise. The mass spectrum data 1901 includes a doublet 1904 and 1905 which represents true data while the signal at location 1902 is false. This is detected by noting the distance which should exist between a doublet and by searching for the distance in the data. In particular, the peak at location 1902 is compared to the abundance data at location 1903; when it is determined that no peak exists at 1903, the peak at 1902 is given a rank of 0 which causes this noise to be removed from the signal or mass spectrum shown as 1906 in FIG. 20B. On the other hand, the peak at m/z value 1904 is separated from the predetermined doublet distance shown by the location 1905, and this causes the filtering algorithm to recognize the valid presence of a signal which is given a rank of 1, thereby causing the filtered mass spectrum data shown as signal 1906 to retain the peak at location 1904 as shown in FIG. 20B.

EXAMPLES

Example 1

In this example a high mannose type oligosaccharide is sequenced using the method of this invention. In a modification of the method described by Parekh et al (U.S. Pat. No. 5,667,984) the mass defect label 2-amino-6-iodo-pyridine (Label 1) is conjugated to the reducing terminus of the oligosaccharide in the presence of sodium cyanoborohydrin ($NaBH_3CN$). This incorporates a single mass defect element (I) into the parent oligosaccharide. The addition of the mass defect element allows the labeled oligosaccharide fragments to be distinguished from unlabeled fragments and matrix ions in the mass spectrum.

The Label 1 conjugated oligosaccharide is then aliquoted to reaction tubes containing different saccharases (as described in Tables 2 and 3) in appropriate reaction buffers. The reactions are allowed to proceed to completion. Upon completion the reaction products are subsequently conjugated at the reducing ends of the fragments generated by reaction with the mass defect labels shown for each enzyme (Table 3) in the presence of sodium cyanoborohydrin. Since these labels contain different numbers of mass defect elements, the digest fragments may be distinguished from the terminal fragment of the original oligosaccharide.

TABLE 2

Oligosaccharase Enzymes

| ENZYME # | SPECIES | Enzyme |
|---|---|---|
| 1 | ASPERGILLUS SAITOI | alpha-mannosidase I |
| 2 | Jack bean | alpha-mannosidase |
| 3 | Achatina saitoi | alpha-mannosidase II |
| 4 | Jack bean | beta-hexosaminidase |
| 5 | Prevotella sp. | beta-hexosaminidase |
| 6 | Achatina fulica | beta-mannosidase |
| 7 | Streptococcus pneumonae | N-acetyl beta-hexosaminidase |
| 8 | Helix pomatia | beta-mannosidase |

TABLE 3

Reaction and Label Combinations

| Enzyme* | Action | Mass Defect Label Used |
|---------|--------|------------------------|
| None | None | 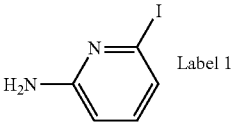 Label 1 |
| 1 | Cleaves 1 α 2 mannoses at any site | 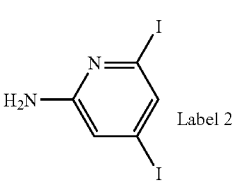 Label 2 |
| 3 | Cleaves 1 α 3, 6 mannoses to any site<br>Cleaves 1 α 3 mannoses when linked to a branched sugar | 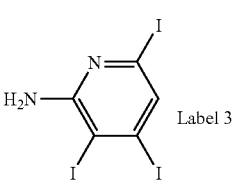 Label 3 |

*Enzyme number corresponds to the description in Table 2

An aliquot of the Label 3 conjugated reaction mixture (i.e., digested with Enzyme #3) is further digested with Enzyme 1. The reaction reducing sugar termini generated by this reaction are subsequently conjugated to Label 2 as previously described.

Aliquots from all these reactions are then mixed, acidified by the addition of a 50% v/v mixture of 2% acetic acid in methanol and subjected to mass spectral analysis. Because of the low stability of the acetal conjugate in acid solutions mass spectral analysis must be conducted immediately after acidification. Alternatively, a different label series that incorporates a hard charge (e.g., an N-alkyl-iodo-pyridium series) may be subjected to mass spectral analysis without acidification. The resulting mass spectrum is deconvolved to remove all chemical noise that does not contain a mass defect labeled peak by the methods of this invention. The resulting deconvolved mass defect spectrum is then algorithmically searched by the methods of this invention by predicting all the possible oligosaccharide sequences that could be attached to each mass defect label used.

Figure 21:
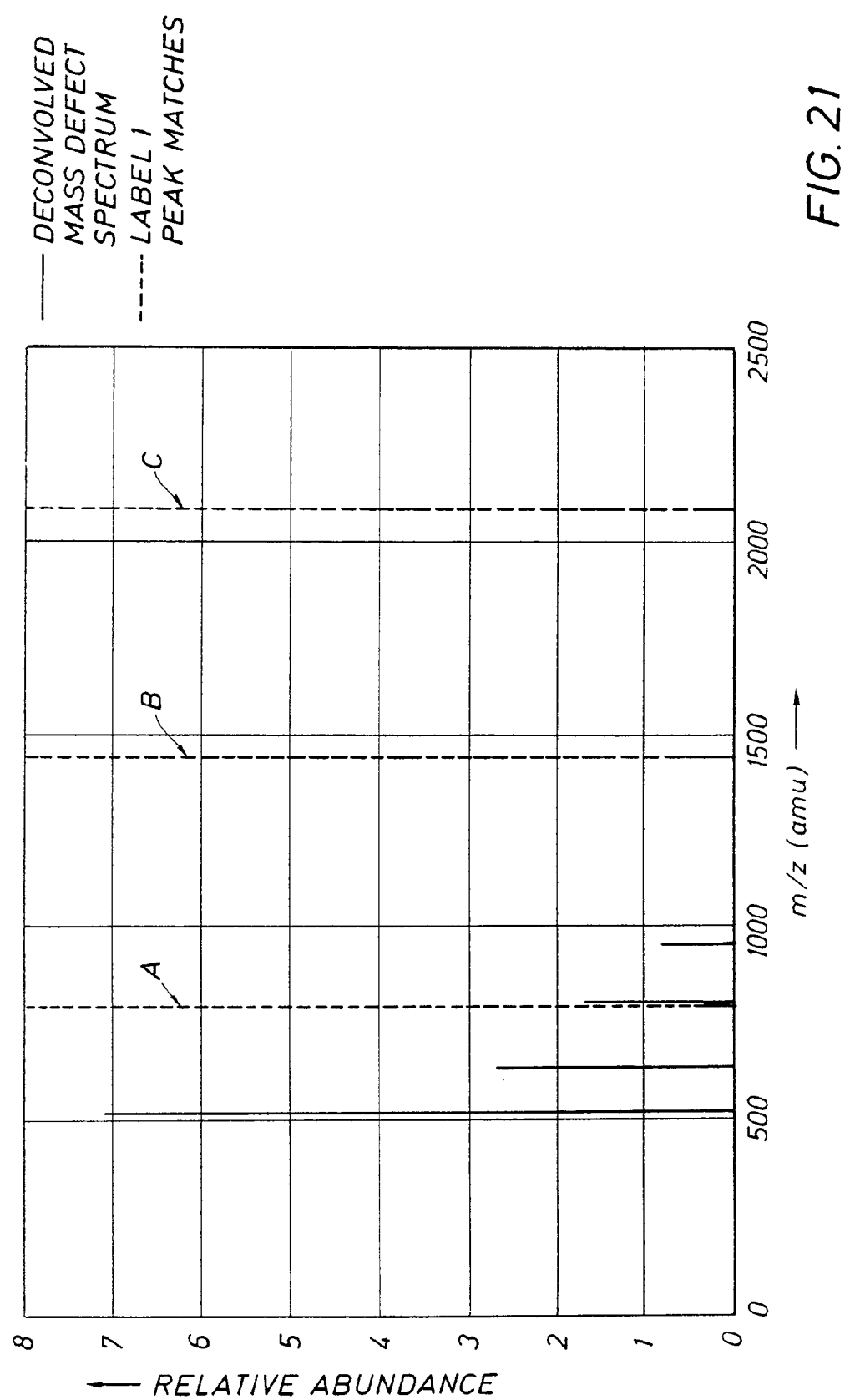
FIG. 21 illustrates an exemplary oligosaccharide composition of mass spectrum peaks matching label 1 of Table 3.
Figure 22:
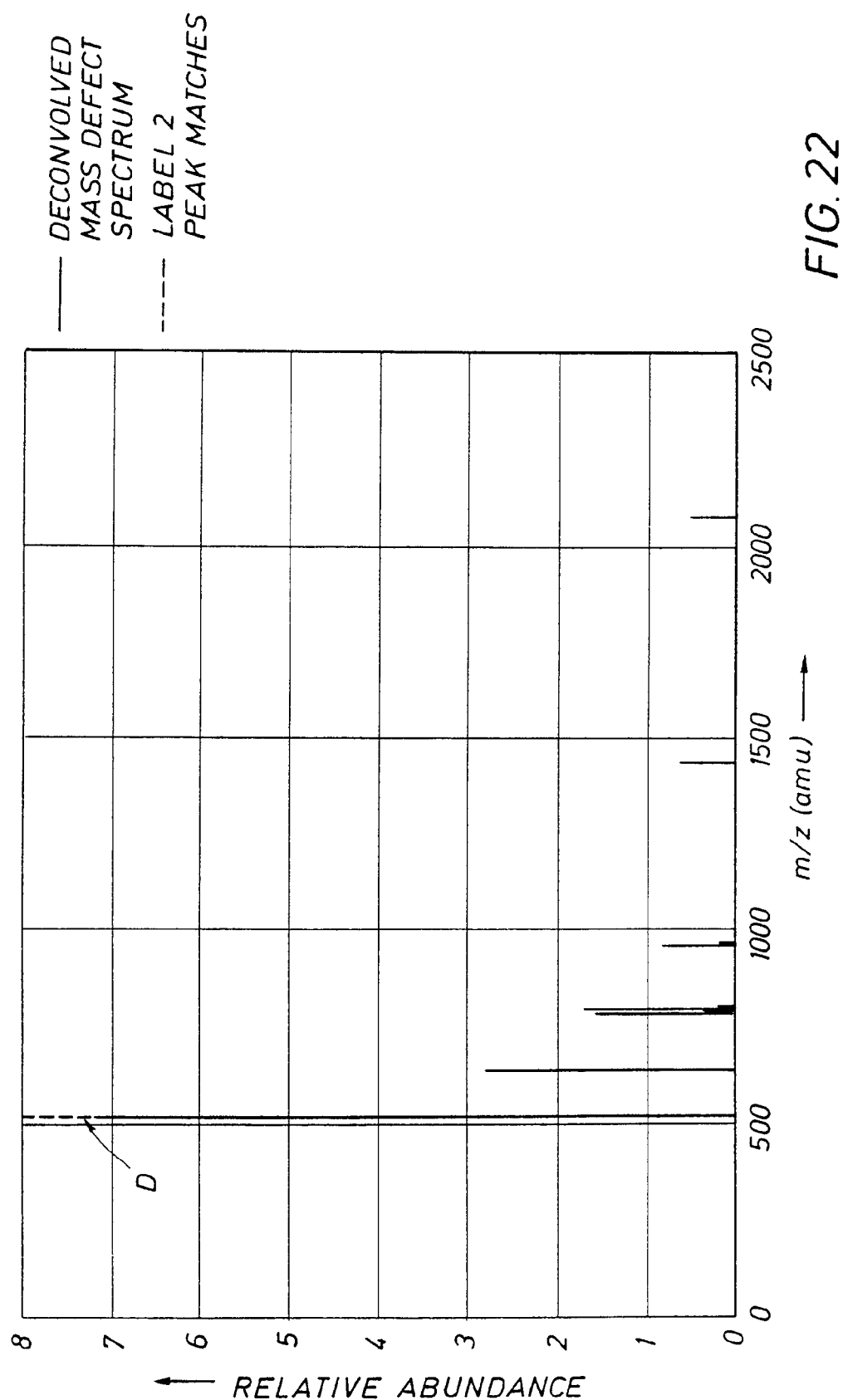
FIG. 22 illustrates an exemplary oligosaccharide composition of mass spectrum peaks matching label 2 of Table 3.
Figure 23:
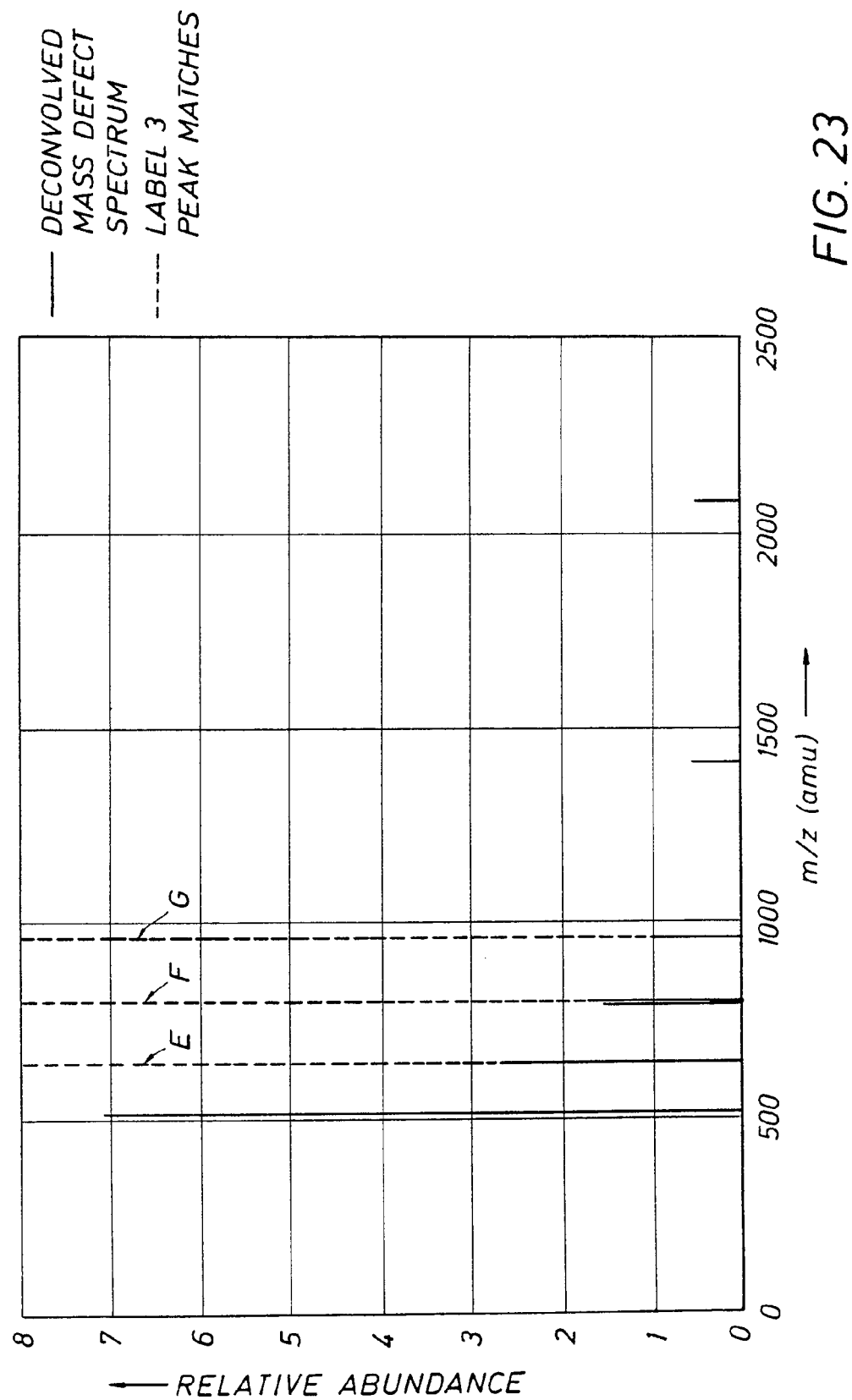
FIG. 23 illustrates an exemplary oligosaccharide composition of mass spectrum peaks matching label 3 of Table 3.

The search algorithm calculates the mass for every branch combination of hexose (Hex), and N-acetylaminohexose (HexNAC). Each Hex monomer unit adds a monoisotopic mass unit of 179.055565 amu to the weight of the estimated fragment mass. Each HNAC monomer unit adds a monoisotopic mass of 220.082114 amu to the estimated fragment mass. There is a net loss of (n−1) times 17.00274 amu for each sugar (n) contained in the fragment. The oligosaccharide composition of the peaks matching the search criteria for Labels 1, 2, and 3 are shown in FIGS. 21, 22, and 23, respectively. The number of hexoses and N-acetylaminohexoses corresponding to these peaks are shown in Table 4.

TABLE 4

Number and Type of Hexoses Corresponding the FIG. 1 (A, B, and C) Peaks

| Peak | Composition HNAC | H |
|------|------|---|
| A | 2 | 1 |
| B | 2 | 5 |
| C | 2 | 9 |
| D | | 1 |
| E | | 1 |
| F | | 2 |
| G | | 3 |

The mass ladder formed from the fragments conjugated to Label 1 suggest that the outer most sugars must be hexoses. Since the highest mass fragment conjugated to label 1 must correspond to the parent oligosaccharide, then we can deduce that the 4 hexose mass difference to the first label 1 conjugated fragment must correspond to 4 α-mannoses since both enzyme 1 and enzyme 3 only cleave α-mannoses. Since peak D is the only label 2 conjugate match in FIG. 22, we can deduce that 4 of the outermost sugars from the reducing terminus are 1α2 linked mannoses and that there are no internal 1α2 mannoses.

The next fragment in the label 1 mass ladder (FIG. 21, Peak A) differs by an additional 4 hexoses from the previous fragment. This must correspond to a sample digested with enzyme 3. The only matching label 3 conjugated fragments (FIG. 23) are E (a 1 hexose fragment), F (a 2 hexose fragment) and G (a 3 hexose fragment). Since peaks F and G total 5 hexoses, we can deduce that at least one of these fragments must contain a 1α2 linked mannose. Since enzyme 3 only cleaves 1α3 and 1α6 linkages, therefore, we can further deduce that there must be at least two separate 1α3 and/or 1α6 linked mannoses in the structure and that these mannoses must be interior to the 4 1α2 linked mannoses. From this information we can deduce the following partial sequence:

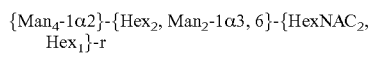

where r indicates the reducing end of the oligosaccharide.

This process is repeated with different enzymes from Table 2 until the complete sequence is determined. For example, digestion with enzyme 3 followed by enzyme 8 allows the determination that the initial sequence is:

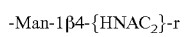

The full sequence of the reducing end of the oligosaccharide is determined by reaction with enzyme 3 followed by enzyme 7.

Example 2

In this example we use the mass defect label for the identification of the fatty acid composition and arrangement in lipids, which we herein define as lipid sequencing. The present example is limited to phosphatyidylcholine; however, it should be apparent to those skilled in the art that with alternative separation methods, spot, and lipase selections that the techniques can be applied to any of the saponifiable lipids as defined by Lehninger (Biochemistry (Worth, N.Y., 1975)).

Figure 24:
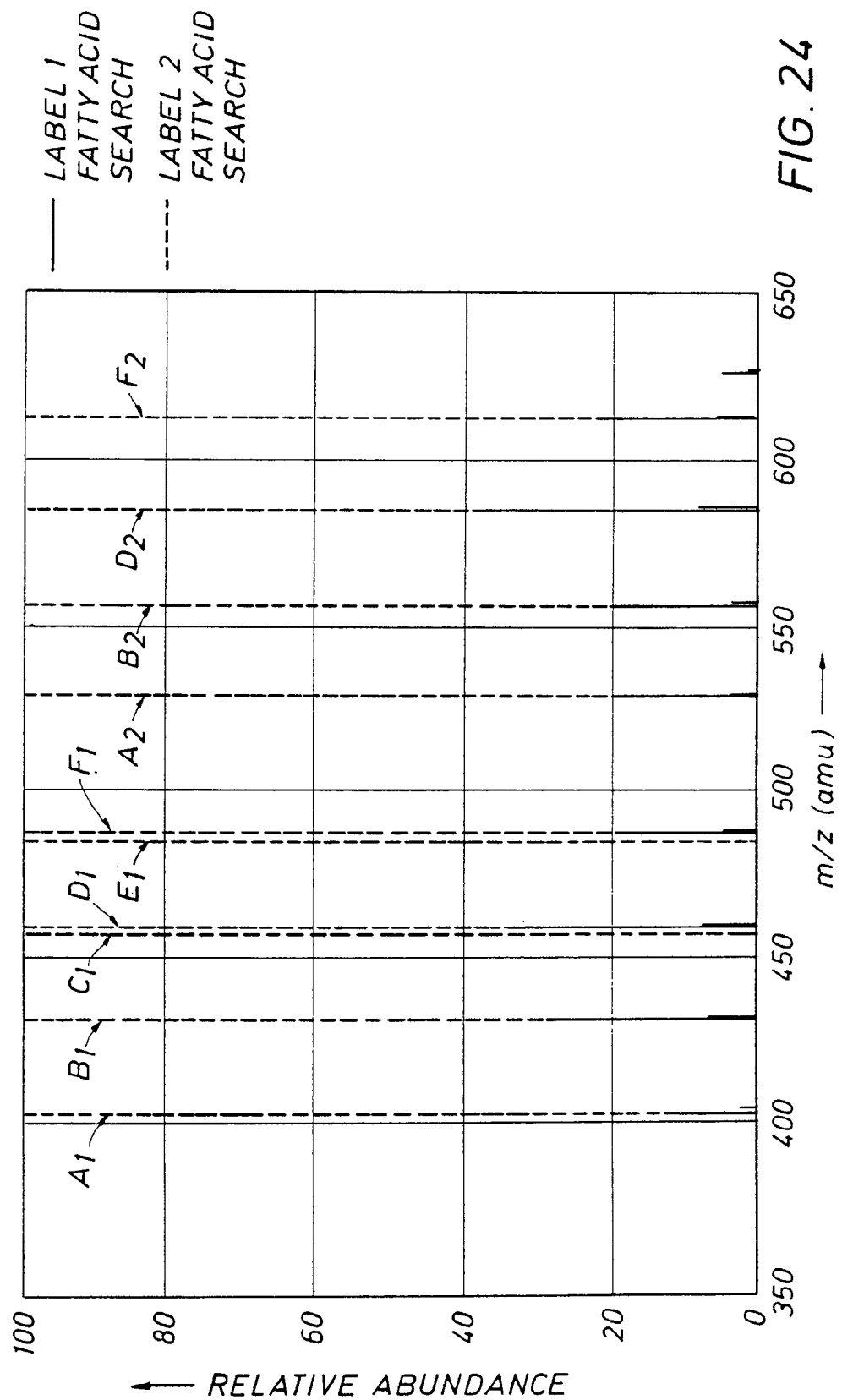
FIG. 24 illustrates an exemplary fatty acid composition of mass spectrum peaks matching label 1 and label 2.

A lipid extract is made by ether extraction of an *E. coli* K-12 cell pellet by the method of Hanson and Phillips (In: Manual of methods for general bacteriology, p328, (Amer. Soc. Microbiol., Washington, D.C., 1981)). The ether was removed by evaporation and the lipid pellet resuspended in a 65:25:5 methanol:chloroform:formic acid solvent system (containing 0.1% butylated hydroxytoluene to inhibit oxidation. Half the volume was spotted in each of two lanes of a scribed silica HL plate (Altech, Deerfield, Ill.) and allowed to dry. The lipids were separated using the same solvent system by the method described by Waters and Huestis (Amphipathic Interactions with erythrocytes and platelets, Doctoral Dissertation (Stanford University, Stanford, Calif., Dept. of Chemistry, 1992)). This process separates the lipids by head groups. One lane was removed and exposed to iodine vapor to determine the relative positions of each of the lipid fractions (FIG. 24). The silica matrix was scraped from the region in the undeveloped lane corresponding to the phosphatidylcholine spot and was placed into a microfuge tube.

The silica pellet was resuspended in 100 µl of phospholipase reaction buffer (100 µl) as described by Cottrell (Meth. Enzymology, 71:698 (1981)) and vortexed vigorously. An aliquot (50 µl) of the silica suspension was removed to a second microfuge tube. The first aliquot was treated by the addition of 1 IU of phospholipase A2 from *Apis mellifera* (Sigma-Aldrich, St. Louis, Mo.), which selectively hydrolyzes the C2 fatty acids. The second aliquot was treated by the addition of 1 IU of Novozyme 871 (Sigma-Aldrich, St. Louis, Mo.), which selectively hydrolyzes the C3 fatty acids of phosphoglycerides. Both reaction mixtures were incubated at room temperature overnight.

The reaction mixtures were evaporated to dryness under vacuum, and resuspended in approximately 25 µl of dichloromethane. Mass defect Label 1 (2-amino-5-iodo-pyridine) was added (20 µl of a 1 M solution in dichloromethane) to the phosphorylase A2 reaction mixture. Mass defect Label 2 (2-amino-3,5-iodo-pyridine) was added (20 µl of a 1 M solution in dichloromethane) to the Novozyme 871 reaction mixture. An aliquot (20 µl of a 1 M solution of 1,3-dicyclohexylcarbodiimide) was then added to both tubes and incubated for 2 hours. The carbodiimide catalyzed the conjugation of the enzyme liberated fatty acids to the mass defect labels. The reaction mixtures were acidified by addition of 1% formic acid (v/v) and mixed immediately prior to mass spectrometric analysis by microspray on an ABI Mariner MS.

The chemical noise was deconvolved from the resulting mass spectrum by the algorithms of the present invention, leaving the deconvolved mass spectra shown in FIG. 24. The identities and relative abundances of the various fatty acids at C2 and C3 on the phosphatidylcholine lipid backbone were determined by mass addition to each label. The lengths of the natural fatty acid tails occur in multiples of either —CH$_2$CH$_2$- (28.031300 amu) or —CH═CH— (26.015650) units. The mass of one H (1.007825 amu) is added to each predicted chain length to complete the stoichiometry of the terminal methyl group. Branched fatty acids can not be distinguished from single chain analogs because the loss of one hydrogen from the mass at a branch point is recovered by the extra H needed to complete the stoichiometry at the terminus of the new branch.

Figure 25:
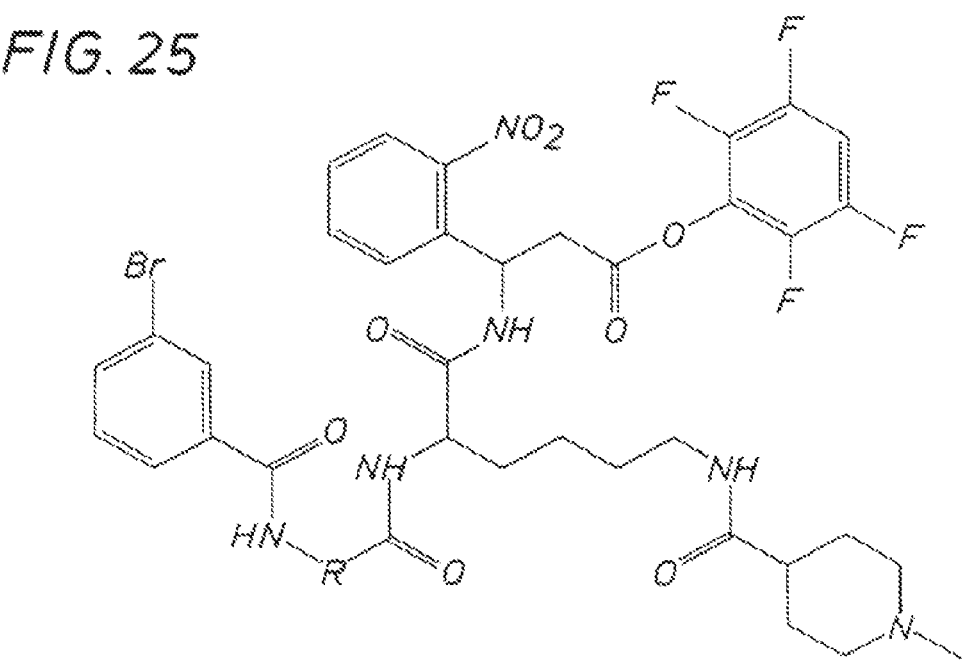
FIG. 25 illustrates the general structure of the photocleavable mass defect tag where Br is the mass defect element that is linked through the amino acid (R) to the remainder of the tag.

The relative abundance of the various fatty acids at the C2 position can be estimated from the monoisotopic peak heights for the various Label 1 conjugated peaks ($A_1 \rightarrow F_1$, FIG. 25). The relative abundance of the various fatty acids at the C3 position of phosphatidylcholine can be estimated from the monoisotopic peak heights for the various Label 2 conjugated peaks ($A_2 \rightarrow F_2$, FIG. 24). Therefore, the average sequence of the phosphatidylcholine of *E. coli* is shown in Table 5.

It is obvious to those skilled in the art that further lipid sequence resolution may be obtained through the use of a second thin layer chromatography dimension or other separation methods in which the hydrophobiciity of the fatty acids is used to resolve the lipids (See Morris, L. J., J. Lipid Res., 7:717-732 (1966)).

TABLE 5

*E. Coli* Phosphatidylcholine Sequence Composition

| | | Approximate Abundance (%) | |
|---|---|---|---|
| Peak | Fatty Acid | C3 (Label 2) | C2 (Label 1) |
| A | n-dodecanoic | 20 | 10 |
| B | n-tetradecanoic | 20 | 30 |
| C | Palmitoleic | — | 2 |
| D | n-hexadecanoic | 37 | 35 |
| E | Oleic | — | 2 |
| F | n-octadecanoic | 22 | 20 |

The present application includes as an appendix a software listing and associated data files which may be used to perform one embodiment of the invention. In particular, a sequencer code is included which performs one embodiment of the sequencing algorithms. A filtering code is also included for performing the filtering algorithm according to one embodiment of the invention. The appendix also includes a sequencer input/output specification which specifies the inputs and outputs associated with the sequencer code and also includes certain example files which indicate data files which are used in conjunction with the sequencer code.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

Example 3

Exemplified is one embodiment of the preparation of photocleavable mass defect labels of the brominated or iodinated aryl ether variety. Such labels are useful for quantifying the relative abundances of biomolecules (e.g., nucleic acids, proteins, or metabolites) that may otherwise exhibit low ionization or detection efficiencies in the mass spectrometer. The mass defect label serves as a surrogate marker for its conjugate biomolecule in the mass spectrometer. Variations of the terminal chemistry provide means for attachment to primary amine, sulfhydryl, and carboxylic acid containing biomolecules. The inclusion of the mass defect element in the label allows the label to be unambiguously resolved from overlapping chemical noise that may be present in the sample and two samples from one another when different numbers of mass defect elements are incorporated into two labels.

The synthesis starts with the compound 4-(tert-butyldimethylsilyl)-phenylborate ether (FT106), which is prepared as described by Schmidt et al. [WO 99/32501 (Jul. 1, 1999)]. This starting material is mixed with one of the corresponding commercially-available bromo- or iodo-phenols shown in Table 3.1 and reacted by the method described by Schmidt et al. [WO 99/32501 (Jul. 1, 1999)] to form the corresponding brominated or iodinated mass defect label precursors. It is obvious from Schmidt, et al. [WO 99/32501 (Jul. 1, 1999)] that additional aryl ether linkages may be inserted between FT106 and the terminal mass defect containing aryl group through the addition of the commercially-available hydroquinone or 4,4'-dihyroxydiphenyl ether with subsequent reactivation of the terminal phenol through creation of a phenolboronic acid terminus by the same method used to create FT106. Similarly, branched aryl ethers may be created by addition and reactivation of the commercially-available 1,2,4-benzenetriol.

conjugated to molecule or macromolecule through the free amine, carboxylic acid, or thiol group by any suitable, generally recognized, conjugation methods to yield a photocleavable mass defect tag conjugated molecule.

TABLE 6

Commercially-Available Bromo- and Iodo-Phenols

| Substitued Phenol | Code | Mass Defect Label Precursor |
|---|---|---|
| 2,4,6-Triiodo-phenol | MDP1 | tert-Butyl-dimethyl-[4-(2,4,6-triiodo-phenoxy)-benzyloxy]-silane |
| 4-Iodo-phenol | MDP2 | tert-Butyl-[4-(4-iodo-phenoxy)-benzyloxy]-dimethyl-silane |
| 3-Bromo-phenol | MDP3 | [4-(3-Bromo-phenoxy)-benzyloxy]-tert-butyl-dimethyl-silane |
| 2,6-Dibromo-4-nitrophenol | MDP4 | [4-nitro-(2,6-dibromo-phenoxy)-benzyloxy]-tert-butyl-dimethylsilane |
| 4-Bromo-2-nitrophenol | DMP5 | [2-nitro-(4-bromo-phenoxy)-benzyloxy]-tert-butyl-dimethylsilane |

The tert-butyl-dimethyl silane protecting group of the mass defect label precursor (MDP™ through MDP5, Table 3.1) is removed with a molar excess of trimethylsulfonium fluoride in methylene chloride or other suitable means generally known in the art. The corresponding deprotected phenol is further reacted with an appropriately-blocked amino linker [See GB 9815163.2 (Jul. 13, 1998)] which is subsequently converted to the primary amine as described by Schmidt et al. [WO 99/32501 (Jul. 1, 1999)]. The amine is further reacted with any appropriate phenyl vinyl sulfone. Examples of appropriate phenyl vinyl sulfones include, but are not limited to those with blocked primary amine (e.g., a nitro group that can subsequently be reduced to aniline), carboxylic acid (e.g., trifluoroacetate ester), or thiol (e.g., a disulfide linkage) substitution on the phenyl ring. The 2° amino group of the linker is then reacted with trifluoroacetic anhydride or methane sulphonyl chloride to render the label photocleavable. Finally, the blocking agent is removed by methods generally recognized in the art and the photocleavable mass tag is Example 4

This example demonstrates how the present invention can be incorporated into affinity-coupled mass labels for the rapid and quantitative analysis of affinity purified mass defect labeled compounds obtained from different samples (See Aebersold et al. WO 00/11208 (Mar. 2, 2000)). This example uses proteins, but it is obvious to those skilled in the art that it can be extended to the analysis for comparison of any molecules co-purified from different samples.

The synthesis of the label starts with any suitable heterobifunctional aryl bromide or iodide (such as the commercially-available examples shown in Table 7). MDP4 and MDP5 (Table 6) provide additional examples. The aniline precursors are reacted with a stoichiometric excess of an N-hydroxysuccimide (NHS) ester of an affinity reagent, such as the commercially-available NHS-iminobiotin or biotin molecules in anhydrous acetonitrile. The reaction mixture is incubated for at least 2 h before the addition of water to hydrolyze any unreacted NHS-ester. The solvent is evaporated to dryness.

The nitrophenyl functionality is then reduced to the primary amine using by methods generally recognized in the art, such as dilute HCl with 5 $nCl_2$ added as a catalyst. The reaction product (Formula I) is purified by affinity chromatography and evaporated to dryness. The second aniline group (produced by reduction of the nitrophenol) is then reacted with another suitable crosslinker (e.g., iodoacetic anhydride) or may be used directly for linkage to carboxylic acid containing target molecules using carbodiimide chemistry. It is obvious to those skilled in the art that many such linkage chemistries are possible to primary amines.

Optionally, the second aniline terminus can be extended by reaction with hydrogenated and perdeuterated polyethylene glycols, as described by Aebersold et al. [WO 00/11208 (Mar. 2, 2000)] to produce a series of isotopically-distinct mass defect tags for differential labeling. Similarly, isotopically pure aryl bromide or iodide starting materials may be used to generate isotope-coupled affinity tags directly.

Formula I illustrates a mass defect label iminobiotin affinity tag where X represents a mass defect element (e.g., bromine or iodine) and n represents the number of mass defect elements. The Linker is any linkage chemistry that can be used to attach the mass defect affinity-coupled tag to a target molecule. Examples include aniline (which can be linked to carboxylic acids through carbodiimide chemistry), and iodoacetamide (formed by reaction of aniline with iodoacetic anhydride).

Formula I

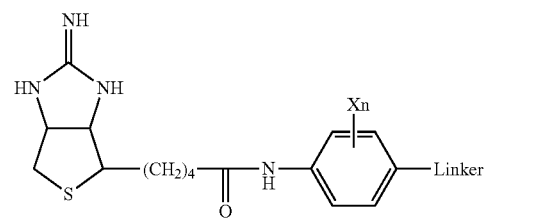

TABLE 7

Formula I

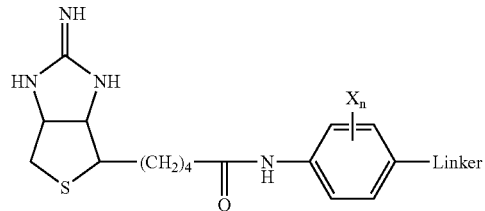

Examples of Affinity-Coupled Mass Defect Labels

| Heterobifunctional aryl bromide or iodide | Code | Affinity-Coupled Mass Defect Label |
|---|---|---|
| 2-bromo-4-nitroaniline | MDA1 | |
| 2,6-dibromo-4-nitroaniline | MDA2 | |

TABLE 7-continued

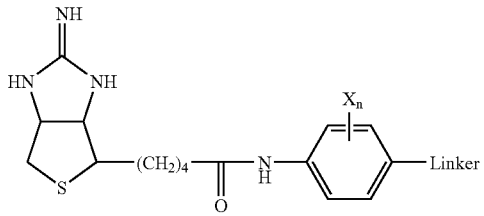

Formula I

Examples of Affinity-Coupled Mass Defect Labels

| Heterobifunctional aryl bromide or iodide | Code | Affinity-Coupled Mass Defect Label |
|---|---|---|
| 2,6-diiodo-4-nitroaniline | MDA3 | |

Blood plasma samples (1 ml) are obtained from each of two patients and placed into separate microfuge tubes. Each tube is treated as follows. The macromolecules are precipitated by the addition of trichloroacetic acid to a final concentration of 10% w/v and the tubes are incubated on ice for 20 min. The precipitate is pelleted by centrifugation (14,000 g) and the supernatant removed. The pellet is dried under vacuum. The dried pellet is resuspended in 100 microliters of a suitable tryptic digestion buffer containing 100 IU of trypsin and 0.1% w/v tris(2-carboxyethyl) phosphine hydrochloride. The solution is incubated overnight at 37 C.

Isotopically pure aliquots of MDA1 are prepared with an iodoacetamide linker. An aliquot (50 microliters) of the tryptic digest of sample 1 is added to a microfuge tube containing 10 mg of [79Br]-MDA1. A similar 50 microliter aliquot of the tryptic digest of sample 2 is added to a microfuge tube containing 10 mg of [81B]-MDA1. Both tubes are incubated for 3 h prior to mixing the contents together. The affinity-labeled molecules are purified by chromatography through a streptavidin-agarose affinity column (Sigma-Aldrich, St. Louis, Mo.) following the manufacturer's recommended procedure. The recovered tagged peptide mixture is analyzed by mass spectrometer with the mass defect peaks deconvolved from the chemical noise generated from unlabeled peptides by the methods of the present invention. All remaining isotopically-distinct pairs of peaks were quantified for their relative abundance.

Example 5

Ness et al. (U.S. Pat. No. 6,027,890 (Feb. 22, 2000)) describe a class of photocleavable mass tags, based on 2-aminomethyl-nitrophenyl acids (e.g., benzoic or phenylacetic acid), that provide an alternative to that described in Example 3, for surrogate analysis of tagged molecules by mass spectrometers. While Ness et al. allow the incorporation of iodine into the weight range adjuster component of the label as part of an allowable list of elements including C, N, O, H, F, S, and P, they fail to teach the importance of iodine as a mass defect element. Specifically, they teach that H, F, and I are added as a means to satisfy the valency requirements of the mass weight range adjustment moiety of their mass tag. Ness et al. also eliminate potential mass defect elements such as bromine and europium for incorporation into their mass tags because these elements have high natural stable isotope abundances. Ness et al. claim that . . . "it is relatively difficult to distinguish tags by mass spectrometry when those tags incorporate atoms that have more than one isotope in significant abundance."

Using the methods of the present invention we specifically incorporate mass defect elements, such as bromine and europium, into the weight range adjuster component of the photocleavable mass tags described by Ness et al. The mass defect provided by these elements allows us to deconvolve mass defect labels from the chemical noise generated from other organic molecules that may be present in the sample. In addition, this example shows how the use of peak pairing deconvolution algorithms, described herein, allows us to further qualify low signal peaks in the spectrum when mass defect elements with high natural abundances of stable isotopes are used.

The synthesis is exactly as described in Example 5 of Ness et al. (U.S. Pat. No. 6,027,890 (Feb. 22, 2000)) with the exception that the $R_{1-36}$ compounds added at step H consist of bromophenylamide derivatives of amino acids with varying chain lengths. The bromophenylamide derivatives are prepared as follows. About 5 g of 3-Bromobenzoic acid and 5 g of 1,3-dicyclohexylcarbodiimide is dissolved in 100 ml of dry toluene. About 10 ml of this solution is aliquoted into each of 10 reaction vials. To each 10 ml aliquot a stoichiometric quantity of one of the tert-butyl esters of the amino acids in Table 8 is added relative to the bromobenzoic acid. A different amino acid tert-butyl ester is added to each tube. The tert-butyl esters are prepared by methods commonly known in the art. The reaction is allowed to proceed overnight at room temperature. The tert-butyl ester is removed by the addition of trifluoroacetic acid. The solvent is removed by evaporation and the bromophenylamide derivatives are purified by preparative reverse phase HPLC using reverse-phase chromatography with gradient elution.

The bromophenylamide derivatives are dissolved and chromatographed using a YMC brand $C_8$ or $C_{18}$ stationary phase (dimensions ~25 cm×6 mm I.D., 5-15 μm, 120-150 Å) and a gradient mobile phase consisting initially of a mixture of acetonitrile and/or methanol with water in a 50/50 ratio; flow rate and gradient are adjusted by the analyst for the specific bromophenylamide derivative. The water phase may optionally be modified to contain 0.1 molar ammonium acetate, diethylamine, triethylamine, or ammonium hydroxide to aid in solubility of the analyte in the mobile phase in cases where extreme tailing or peak broadening has occurred. The organic portion may optionally be modified in strength via adding 1-10% (by volume) of isopropyl alcohol, diisopropyl alcohol, or tetrahydrofuran to effect changes in selectivity between the constituents in the analyte mixture and enable to isolation of the desired bromophenylamide label material from its impurities. The gradient is implemented by changing the total solvent strength from ~50% organic (by volume) to around 90-100% organic over the course of 10 to 20 minutes. Refinement of the mobile phase constituents, flow rate, initial and final solvent strengths, and gradient velocity are made for each derivative as would normally be done by one skilled in the art. Isolated fractions of the desired bromophenylamide material are combined and evaporated prior to incorporation into the mass tag.

This procedure generates a series of labels with the general composition show in FIG. 25, which can be reacted with any primary amine containing target molecule(s) through the tetrafluorophenyl-blocked acid moiety as described by Ness et al.

TABLE 8

Amino Acids for Use in Preparation of Group VI
Variable Weight Components for Mass Tags

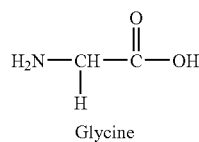

Glycine

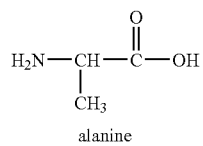

alanine

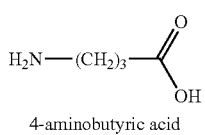

4-aminobutyric acid

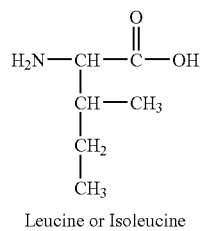

Leucine or Isoleucine

TABLE 8-continued

Amino Acids for Use in Preparation of Group VI
Variable Weight Components for Mass Tags

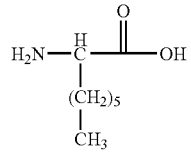

2-Aminooctanoic acid

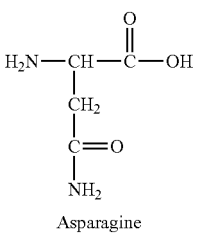

Asparagine

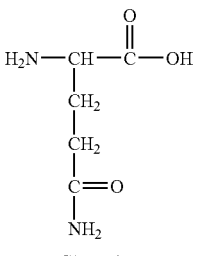

Glutamine

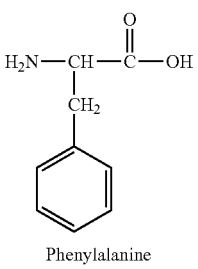 [SMILES: NC(Cc1ccccc1)C(=O)O]

Phenylalanine

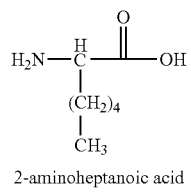

2-aminoheptanoic acid

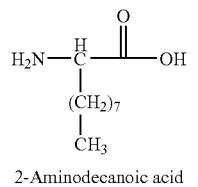

2-Aminodecanoic acid

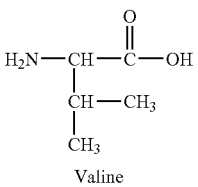

Valine

57

TABLE 8-continued

Amino Acids for Use in Preparation of Group VI
Variable Weight Components for Mass Tags

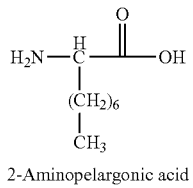

2-Aminopelargonic acid

Example 6

This example shows the utility of the photocleavable mass defect labels generated in Example 5. In this example the 3-bromobenzoic acid and alanine conjugate mass tag label is attached to the N-terminus of the peptide bradykinin using methods generally recognized in the art. The labeled peptide is diluted to about 1 ng per microliter into a 50:50:1 by volume acetonitrile:water:triethylamine solution. The solution was injected at about 1 microliter per minute into an Applied Biosystems Mariner ESI-TOF mass spectrometer equipped with the standard microspray head and run in negative ion mode. The spray and mass spectrometer settings were optimized for the highest relative abundance of the 3" charge state of the oligonucleotide $dT_6$ that could be achieved with a peak resolution greater than 5000. An Ar-pumped standing wave dye laser (Coherent), which was tuned to 350 nm, was directed at the gap between the spray tip and the nozzle of the mass spectrometer, such that the sample spray would be fully exposed to the laser light to cleave the mass tag.

Figure 26:
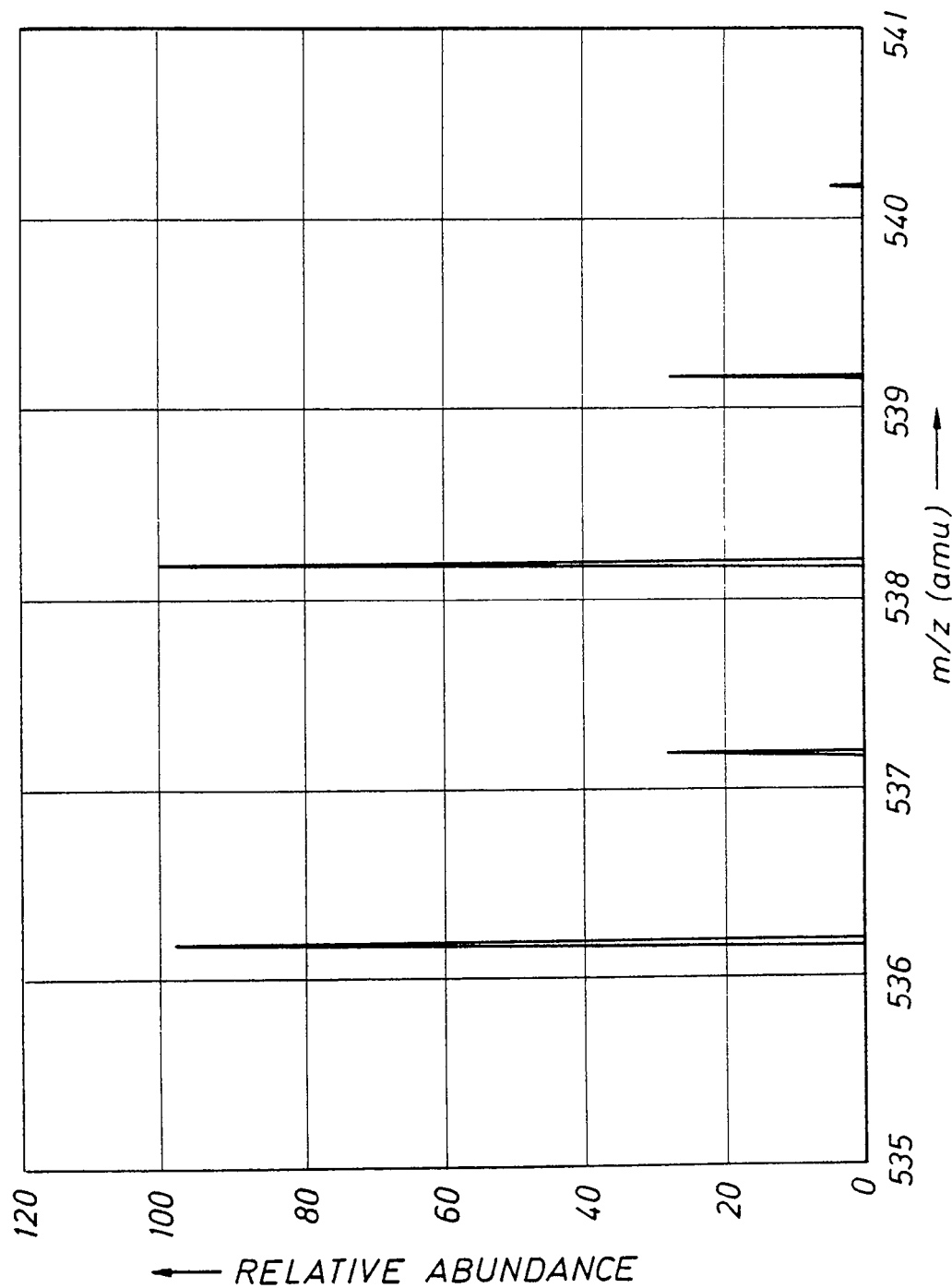
FIG. 26 illustrates an exemplary mass spectrum having in which the chemical noise was deconvolved using the algorithms of the current invention, leaving the mass defect label peaks.

The mass tag labeled sample was analyzed by accumulating 30 scans of 3 seconds duration. The chemical noise in the mass spectrum was deconvolved using the algorithms of the current invention, leaving the mass defect label peaks (FIG. 26).

These deconvolved peaks were fiter qualified by the relative abundances of their isotope pairs using the algorithm:

$$\beta = \left( \frac{(Counts_{[79_{Br}]} + Counts_{[81_{Br}]})}{2} \right) \left[ 1 - \frac{|Counts_{[79_{Br}]} - Counts_{[81_{Br}]}|}{(Counts_{[79_{Br}]} + Counts_{[81_{Br}]})} \right]$$

Figure 27:
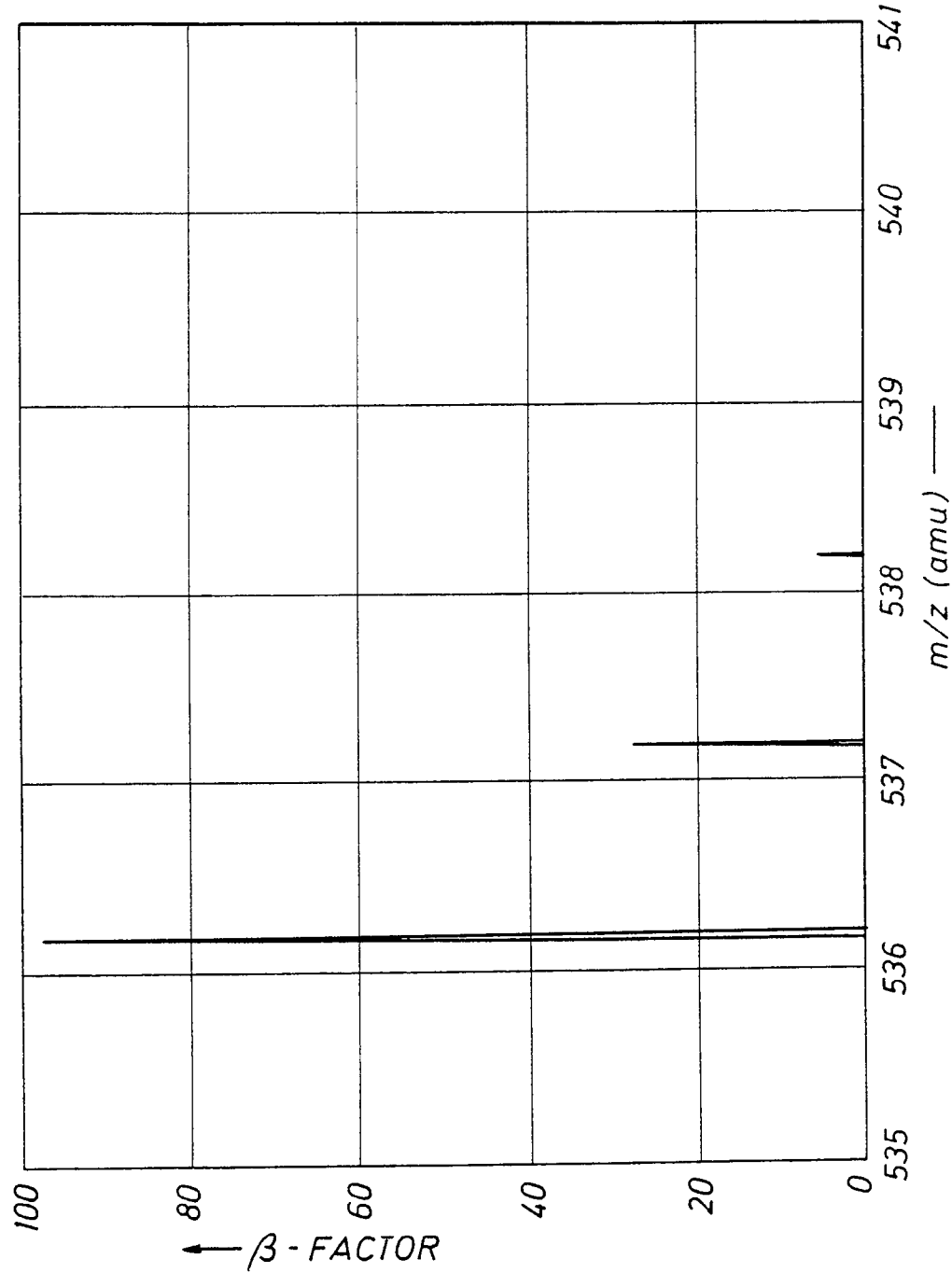
FIG. 27 illustrates a deconvolved and peak-qualified mass spectra of a mass tag region.
Figure 28:
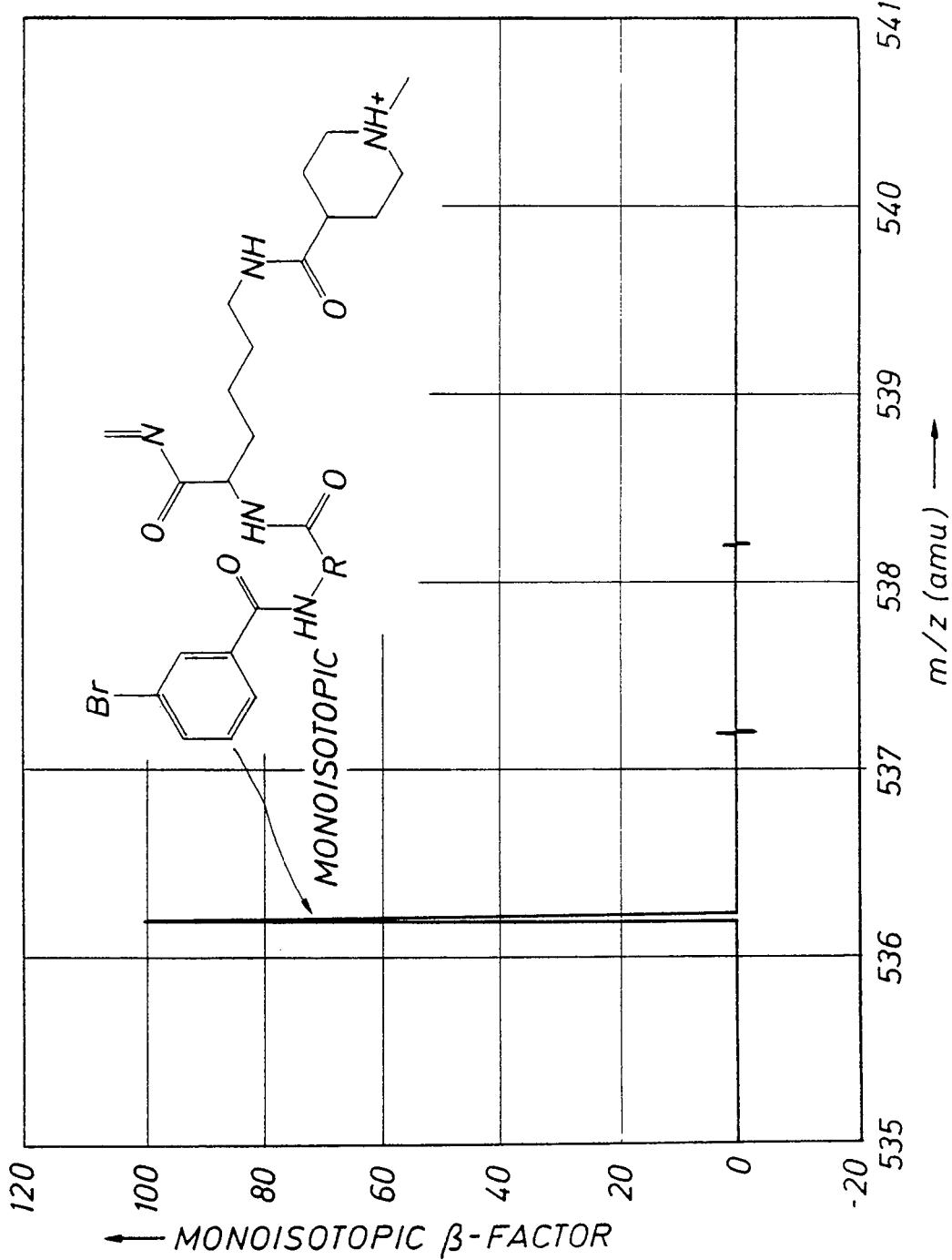
FIG. 28 illustrates an isotope series in the β-Factor spectrum that was further deconvolved to a single monoisotopic peak.

The relative abundance of the lower mass peak was replaced with the β-factor from this calculation. The resulting deconvolved and peak-qualified mass spectra of the mass tag region are shown in FIG. 27. Finally, the isotope series in the β-Factor spectrum (FIG. 28) was further deconvolved to a single monoisotopic peak using algorithms generally known in the art as implemented in the BioSpec Data Explorer software (version 4.0, Applied Biosystems, Framingham, Mass.).

Example 7

This example illustrates the conjugation of a mass-defect label, the N-hydroxysuccinimide (NHS) ester of 5-bromonicotinic acid, to horse apomyoglobin (Myo).

Myo (sequencing grade) (Cat #A8673), 5-bromonicotinic acid (5-BrNA) (Cat #228435), sodium dodecyl sulfate (SDS) (Cat # L6026), and urea (Cat #U0631) were purchased from Sigma-Aldrich and used as supplied. Anhydrous dimethylsulfoxide (DMSO) (Cat #20864), 1-ethyl-3-(3-dimethylaminopropyl)-carbodiimide hydrochloride (EDC) (Cat #22980)), and NHS (Cat #24500) were purchased from Pierce and used as supplied.

The NHS-ester of 5-BrNA was prepared in situ by dissolving 20.8 mg 5-BrNA, 52.7 mg NHS, and 154.1 mg EDC in 0.657 mL DMSO. The sample was briefly sonicated in a bath sonicator to quickly dissolve all the solids. The mixture was incubated overnight at 4° C. Mass spectral analysis of the resulting mixture indicated 93% conversion of the 5-BrNA into the NHS ester (NHS-5-BrNA) by standard addition.

Myo was denatured by heating at 95° C. for 20 mM at a concentration of 5.35 mg/mL in 5% (w/v) aqueous SDS solution. After cooling to ambient temperature, Myo was diluted to 1.07 mg/mL in 80 mM sodium phosphate buffer, pH 7.0, containing final concentrations of 1% (w/v) SDS and 6.4 M urea. Myo was labeled with NHS-5-BrNA by adding 0.353 mL (50 micromoles) NHS-5-BrNA prepared as described above to 2 mL (2.14 mg) of the denatured myoglobin. The sample was incubated overnight at ambient temperature in the dark. The sample was then extensively dialyzed with 50% (v/v) aqueous acetic acid to remove urea and SDS, which has a deleterious effect on electrospray mass spectral analysis. Loss of protein was evident during the extensive dialysis but was not quantified. After the final dialysis, the sample was dried to completion in a speed vac (Savant).

Example 8

This example illustrates the generation of sequencing mass spectral fragment ion species from 5-BrNA labeled myoglobin by IMLS that are shifted from the periodic chemical noise.

A sample was prepared for mass spectrometry by dissolving the dried 5-BrNA labeled myoglobin in 0.1 mL of a 50% aqueous acetonitrile solution containing 1% by volume acetic acid. The labeled protein was subjected to in-source fragmentation in an electrospray-time-of-flight mass spectrometer (Mariner™, PE Biosystems, Inc.) as described by Schneider et al. (WO 00/63683, Oct. 26, 2000). The mass spectrometer settings were optimized and the instrument was calibrated immediately prior to injecting the sample according to the manufacturer's instructions. The sample was infused continuously via a 50 μm I.D. capillary into the electrospray source at a rate of 1 μL/min. The nozzle potential was set at 300 V to induce in-source fragmentation. Spectra were accumulated and summed for 345 s in the range of 50-2000 mass-to-charge units.

Figure 29:
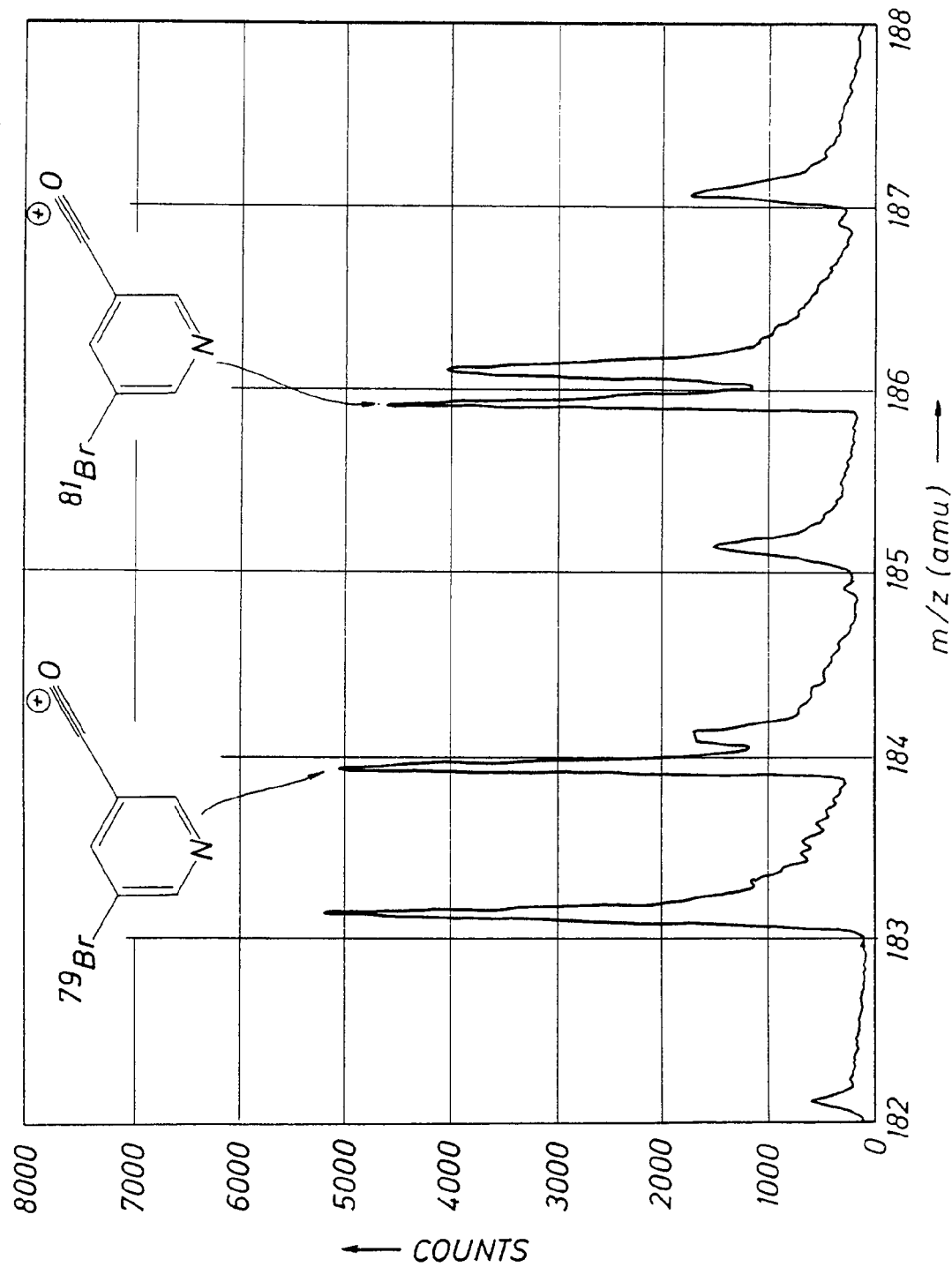
FIG. 29 illustrates a raw mass spectral data showing evidence of a shifted, singly-charged b-type ion.

Examination of the raw mass spectral data shows clear evidence of the singly-charged b-type ion of the label itself (monoisotopic mass 183.94) that is shifted approximately 0.15 amu to the left of peaks that are part of the periodic chemical noise appearing on a period of approximately 1 amu (FIG. 29). The identity of this peak is corroborated by the appearance of a second peak (185.94) that is approximately 2 amu upstream of the first peak, which corresponds to the label fragment ion that incorporates the higher-mass isotope of bromine ($^{81}Br$). The relative intensities of these two peaks are nearly equivalent, reflecting the approximately 1:1 natural abundance of bromine isotopes. Thus, the feasibility of generating label-specific fragment ions incorporating mass defect elements (e.g., bromine here) that can be resolved from chemical noise generated from proteins (which are composed of elements that do not exhibit strong mass defects) during IMLS is demonstrated.

Figure 30:
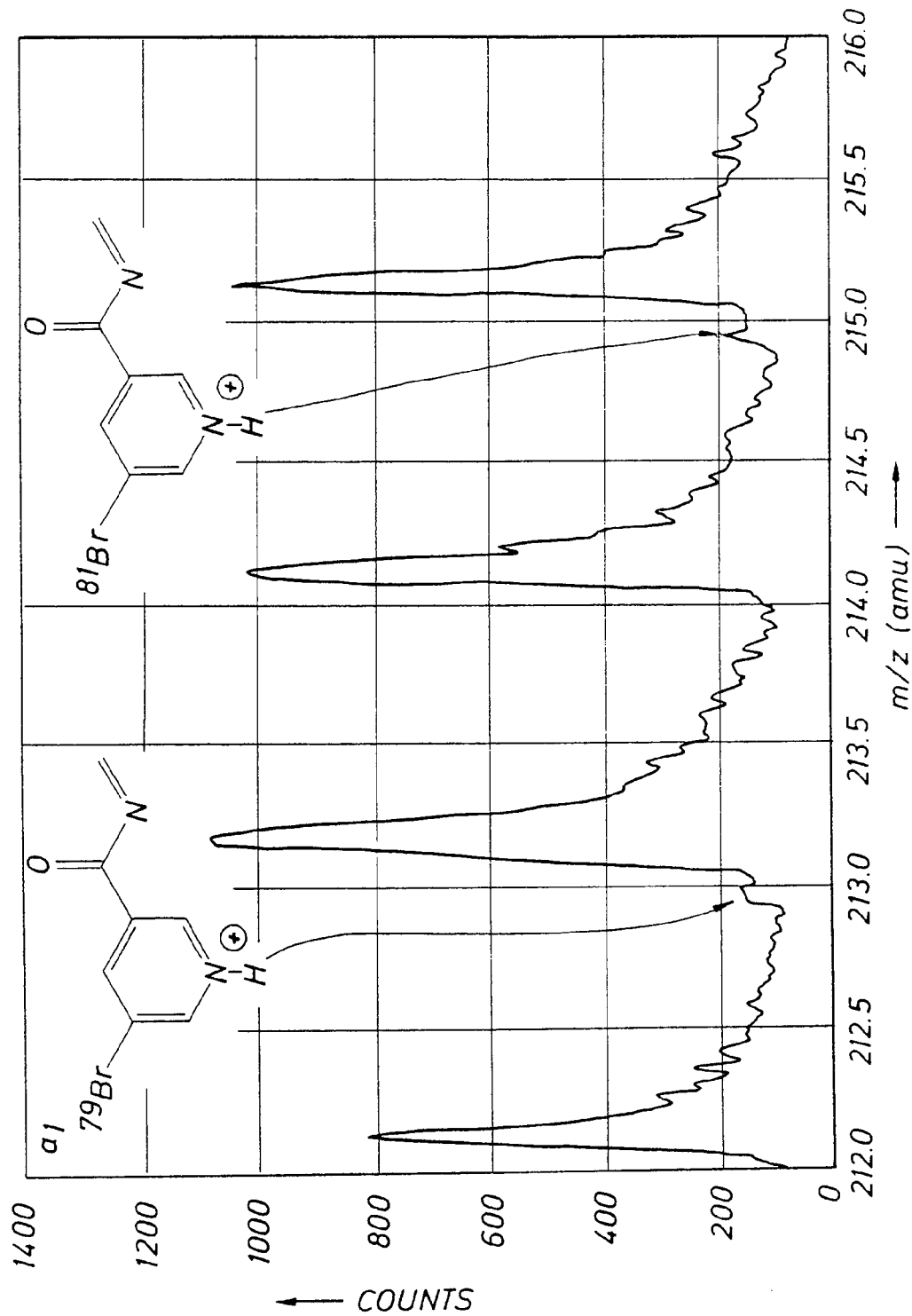
FIG. 30 illustrates a singly-charged al ion doublet (glycine).
Figure 31:
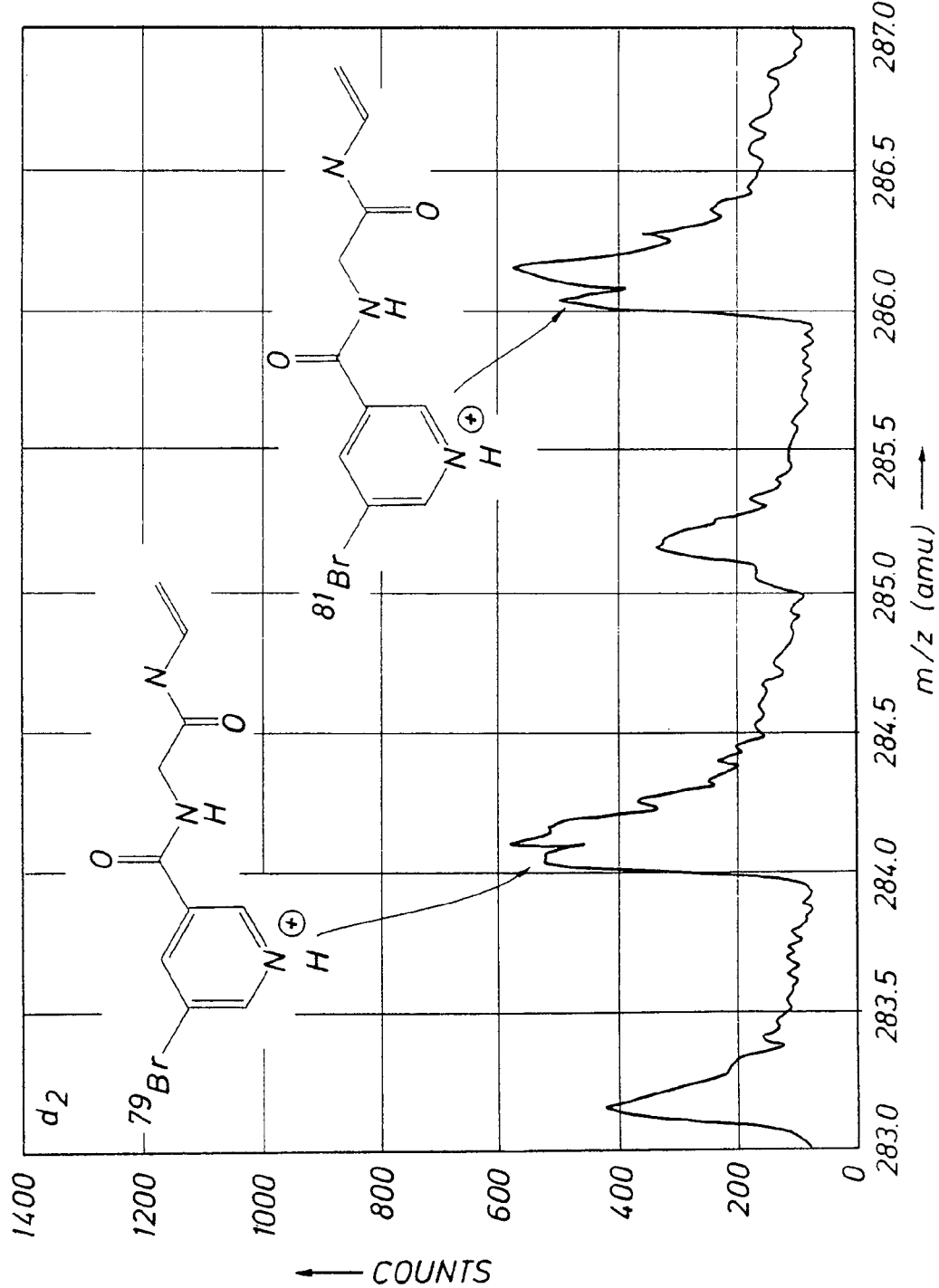
FIG. 31 illustrates a doublet corresponding to the calculated masses of the d2 ion (glycine-leucine).

The spectral data were examined for evidence of mass defect-shifted peaks that correspond to fragment ions of the myoglobin N-terminus. The singly-charged a1 ion doublet (glycine) is apparent at 212.97 and 214.96 m/z (FIG. 30). Furthermore, a doublet corresponding to the calculated masses of the $d_2$ ion (glycine-leucine) (284.05 and 286.05 m/z) is apparent (FIG. 31). Thus, some sequencing ions are generated. The generally low abundance of sequencing ion peaks observed with this label is a result of the high intensity of the ion generated of the label itself which is highly stabilized by conjugation of the label carbonyl with the pydridyl ring (FIG. 29). As is obvious to those trained in the art the generation of this highly conjugated species will lead to preferential cleavage of the label amide linkage over the protein amide backbone, leading to a loss of significant sequencing ions. Therefore, it would be preferable to separate the label carbonyl from the aromatic ring by one or more methylenes to make the label amide linkage of similar bond energy to that of the protein amide backbone.

Example 9

This example illustrates the conjugation of a mass-defect label, the N-hydroxysuccinimide (NHS) ester of 5-bromo-3-pyridylacetic acid (5-Br-3-PAA), to horse apomyoglobin (Myo).

5-Br-3-PAA (Cat #13579) was purchased from Lancaster Synthesis and used as supplied. Myo (sequencing grade) (Cat #A8673), sodium dodecyl sulfate (SDS) (Cat # L6026), and urea (Cat # U063 1) were purchased from Sigma-Aldrich and used as supplied. Anhydrous dimethylsulfoxide (DMSO) (Cat #20864), 1-ethyl-3-(3-dimethylaminopropyl)-carbodiimide hydrochloride (EDC) (Cat #22980)), and NHS (Cat #24500) were purchased from Pierce and used as supplied.

The NHS-ester of 5-Br-3-PAA (NHS-5-Br-3-PAA) was prepared in situ by dissolving 12.7 mg 5-Br-3-PAA, 7.4 mg NHS, and 12.5 mg EDC in 0.235 mL DMSO. The mixture was incubated for 24 h at ambient temperature in the dark Mass spectral analysis of the resulting mixture indicated 53% conversion of the 5-Br-3-PAA by standard addition. Since conversion was not near completion, additional NHS (7.2 mg) and EDC (7.5 mg) were added and incubated for another 24 h. Mass spectral analysis of the resulting mixture after this second incubation period indicated 93% conversion of the starting material.

Myo was denatured by heating 1.89 mg in 0.54 mL 5% (w/v) aqueous SDS solution at 95° C. for 20 min. After cooling to ambient temperature, 1.89 mL of 9M urea in 20 mM sodium phosphate buffer, pH 7.0, was added to the sample. NHS-5-Br-3-PAA (0.24 mL, approx. 19 mM final concentration) was added to the denatured myoglobin. The sample was incubated overnight at ambient temperature in the dark. The reaction mixture was spin dialyzed against 25 mM Tris, pH 8.3 buffer containing 0.1% (w/v) SDS to remove urea and NHS-5-Br-3-PAA reaction by-products. The final retentate (~0.6 mL) containing the labeled myoglobin was subjected to a chloroform extraction procedure to remove bound SDS (Puchades et al. (1999), Rap. Comm. Mass. Spec. 13, 344-349). To the sample, 2.4 mL methanol, 0.6 mL chloroform, and 1.8 mL water were added. The sample was mixed by inverting the tube once. The sample was centrifuged (3743 g, 20 min, ambient temperature) to aid in phase separation, and most of the top layer was discarded. Methanol (1.8 mL) was added to the remaining lower phase and the protein that had precipitated at the interface. The tube was vortexed vigorously and the precipitated protein was pelleted by centrifugation (3743 g, 40 min, ambient temperature). The supernatant was decanted and discarded and the residual protein pellet was dried with a stream of nitrogen gas. The dried labeled Myo was resuspended in 0.4 mL 10% (v/v) aqueous acetic acid solution. The protein concentration (2.6 mg/mL) was measured by BCA assay using BSA as a standard.

Example 10

This example illustrates the use of the automated deconvolution and sequencing algorithms of this invention to find the N-terminal sequence of 5-Br-3-PAA labeled myoglobin fragmented in-source in an ESI-TOF mass spectrometer as described above.

Figure 32:
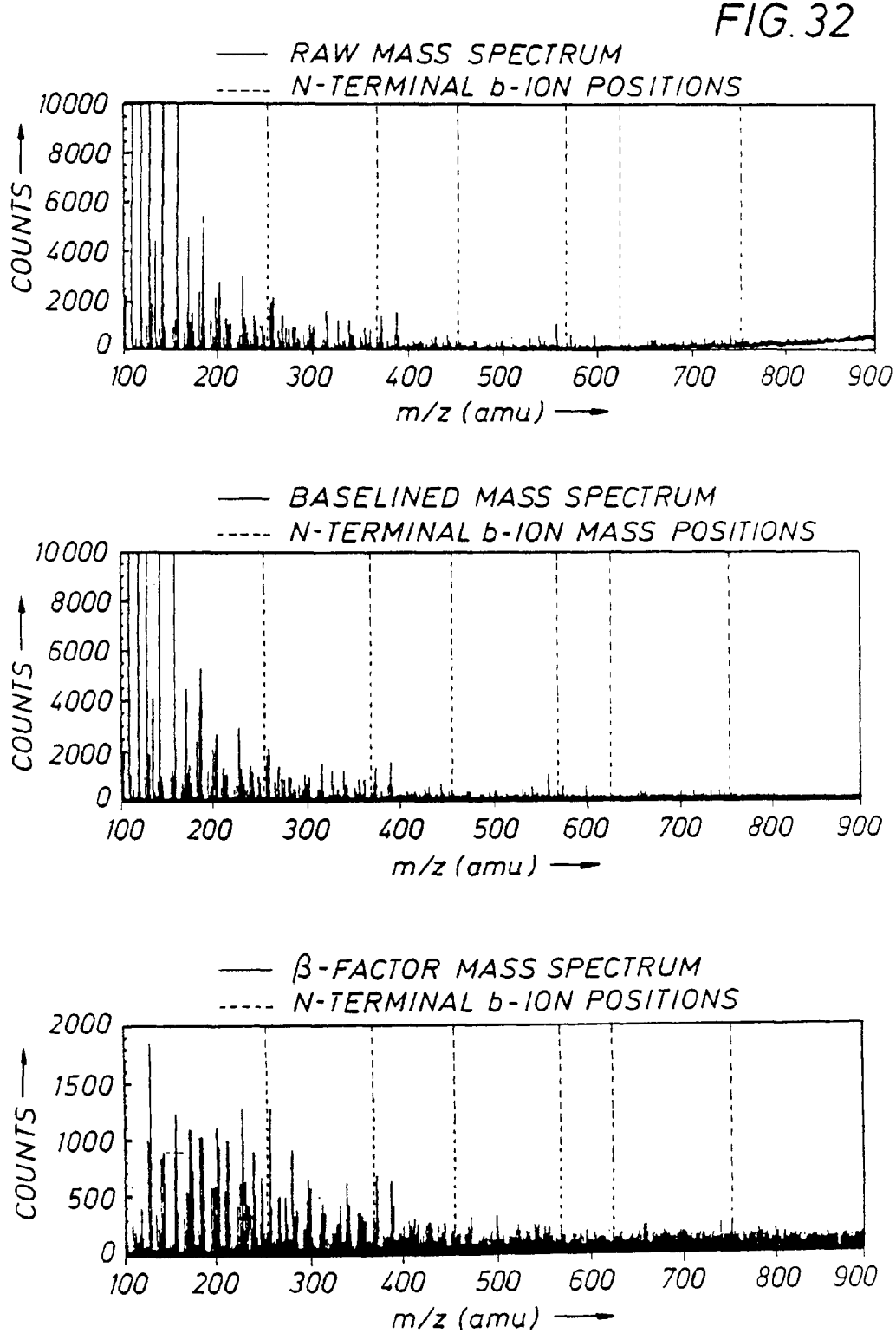
FIG. 32 illustrates the deconvolution of an exemplary mass spectrum.

The raw data used to generate the mass spectrum is exported in ASCII format from the data acquisition system. The natural period of the chemical noise is determined from this raw data using the "deconvolver" code shown in the appendix and is determined to be 1.000575 amu. Using this natural period the spectrum is baselined (output file *.bsl) to correct for instrument error, which is always positive in MS (FIG. 32). Baselining means that the minimum data value in each 1.000575 amu block of data is adjusted to zero by subtracting through every data point in the block of data. The baselined data file is subsequently processed with the "betafactor" as a way to qualify mass defect (Br-containing) peaks, which should always have a matching [$^{81}$Br] peak 1.997954 amu upstream from the [$^{79}$Br] peak (FIG. 32). The resulting *.bfc file is then processed through the "sequencer" code shown in the appendix, with the true N-terminal myoglobin sequence (5-Br-3-PAA-GLSDGE) (SEQ ID NO: 26) being the top ranked solution through the first four residues. In this example the "sequencer" code was limited search for the first charge state of b-ions.

Figure 33:
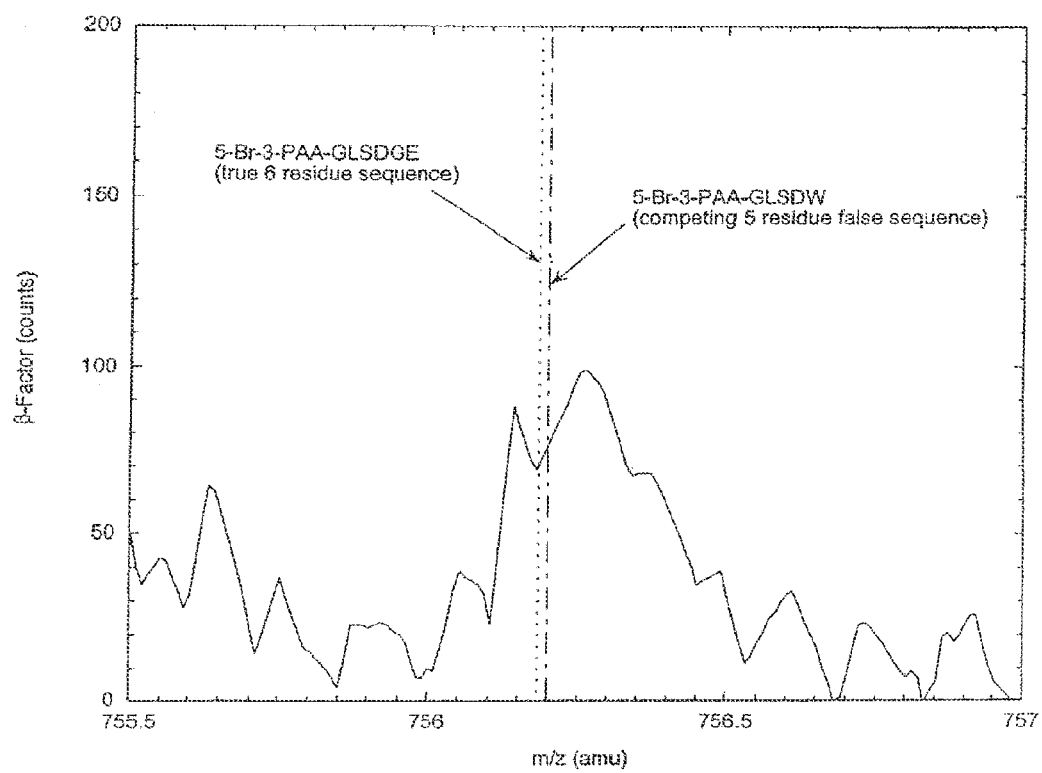
FIG. 33 illustrates an overlap of a true 6-residue sequence and a competing 5-residue false sequence.

When the "sequencer" code is run to determine the sequence of the first five residues, the sequence GLSDW (SEQ ID NO: 27), which yields a theoretical mass of 756.1993 overlaps (FIG. 33) the peak corresponding to the mass defect position of the sixth residue of the true sequence (GLSDGE (SEQ ID NO: 26) at 756.1840). This results in GLSDW (SEQ ID NO: 27) being the top ranked sequence at five residues. However, when "sequencer" is run through six residues the true sequence GLSDGE (SEQ ID NO: 26) becomes top ranked again because GLSDW (SEQ ID NO: 27) fails to propagate a competing sequence at the sixth residue. This shows the advantage of a cumulative probability algorithm.

Example 11

Figure 34:
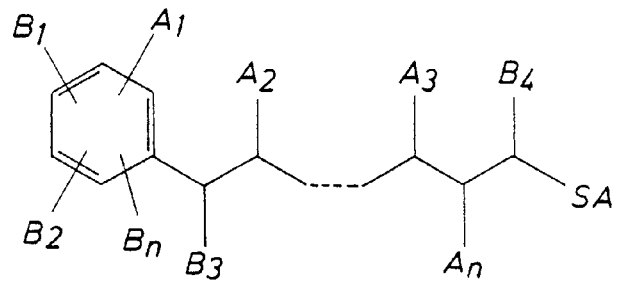
FIG. 34 illustrates a general chemical structure exemplifying a core succinic anhydride reactive moiety with a combination of ionizable groups and mass defect elements.

This example illustrates the synthesis of a generic mass-defect label that incorporates a mass-defect element of this invention (i.e., bromine), an ionizable group (i.e., pyridyl) and a succinic anhydride linking moiety for attachment to the N-terminus or other desired primary or secondary amino group of a polypeptide or other species. It has been demonstrated that succinic anhydride, and ostensibly its derivatives, react with nearly quantitative efficiency towards polypeptide amino groups (Munchbach et al., Anal. Chem. 72: 4047-4057 (2000)). It is clear to those skilled in the art that other comparable aliphatic/aromatic species can be readily synthesized that contain any combination of ionizable groups (A1 . . . An), mass defect elements (B1 . . . Bn), and a core succinic anhydride reactive moiety (SA) (FIG. 34).

Figure 35:
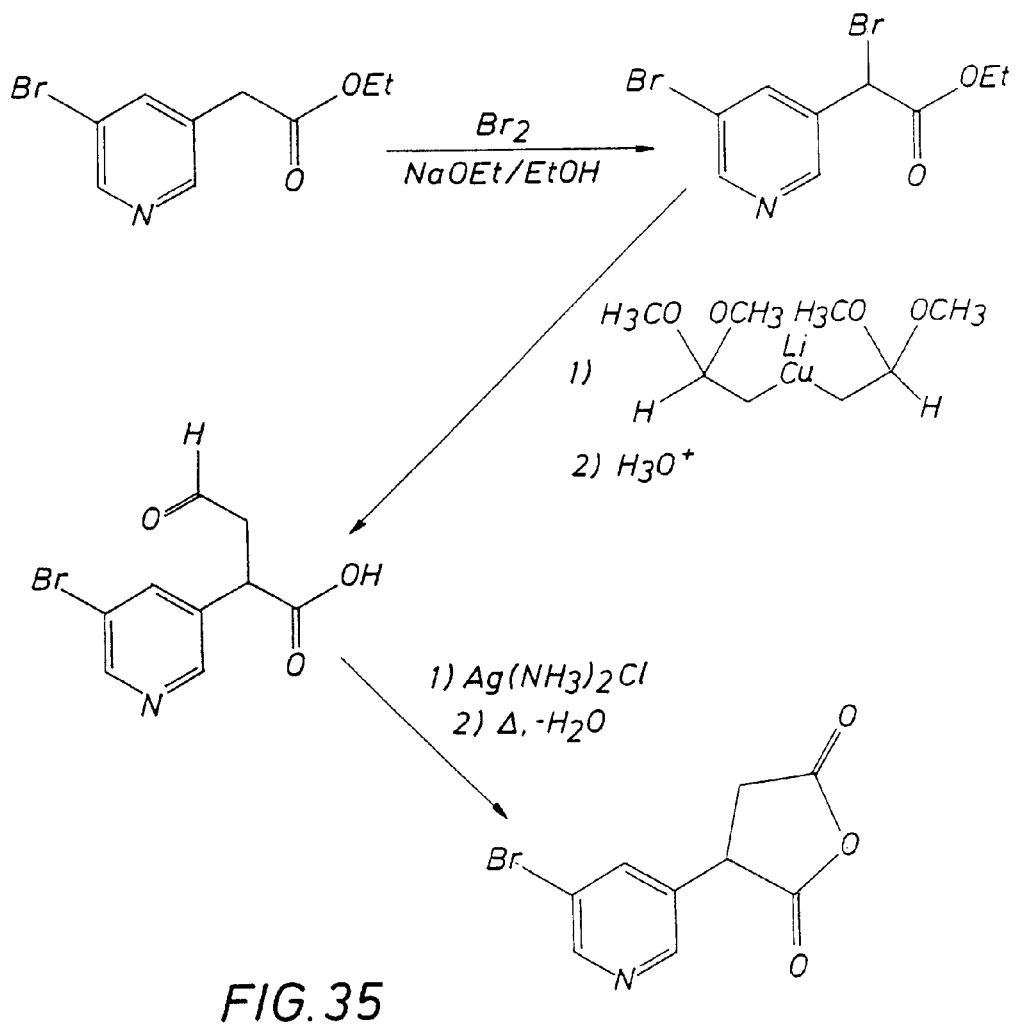
FIG. 35 illustrates an exemplary synthetic scheme for producing an exemplary succinic anhydride represented in FIG. 34.

As an exemplary but not exclusive strategy, FIG. 35 outlines an overall synthetic scheme for a plausible [(A1 . . . An)-(B1 . . . Bn)-SA] mass defect label. 5-bromo-3-pyridyl acetic acid (Lancaster, Cat #13579) is initially converted to the ethyl ester by reaction with ethanol in the presence of an acid catalyst with removal of water. The resulting ester is then α-brominated by reaction with elemental bromine in a basic solution of sodium ethoxide in ethanol. The brominated α-carbon is then selectively reacted in an anhydrous organic solvent such as tetrahydrofuran with the organocuprous agent lithium di-(bromoacetaldehyde dimethyl acetal)cuprate which is prepared by reaction of commercially-available bromoacetaldehyde dimethyl acetal (Aldrich, Cat #242500) with lithium to form the organolithium species that is converted into the cuprate by reaction with Cu(II)I. The resulting product is treated with aqueous acid to remove the acetal moiety and hydrolyze the ester back to the free acid. The liberated aldehyde is oxidized to the corresponding carboxylic acid by standard oxidizing agents (e.g., $Ag^+$), and the synthesis is completed by cyclization and dehydration of the two generated carboxylic acid groups to form the desired succininic anhydride derivative.

Example 12

Figure 36:
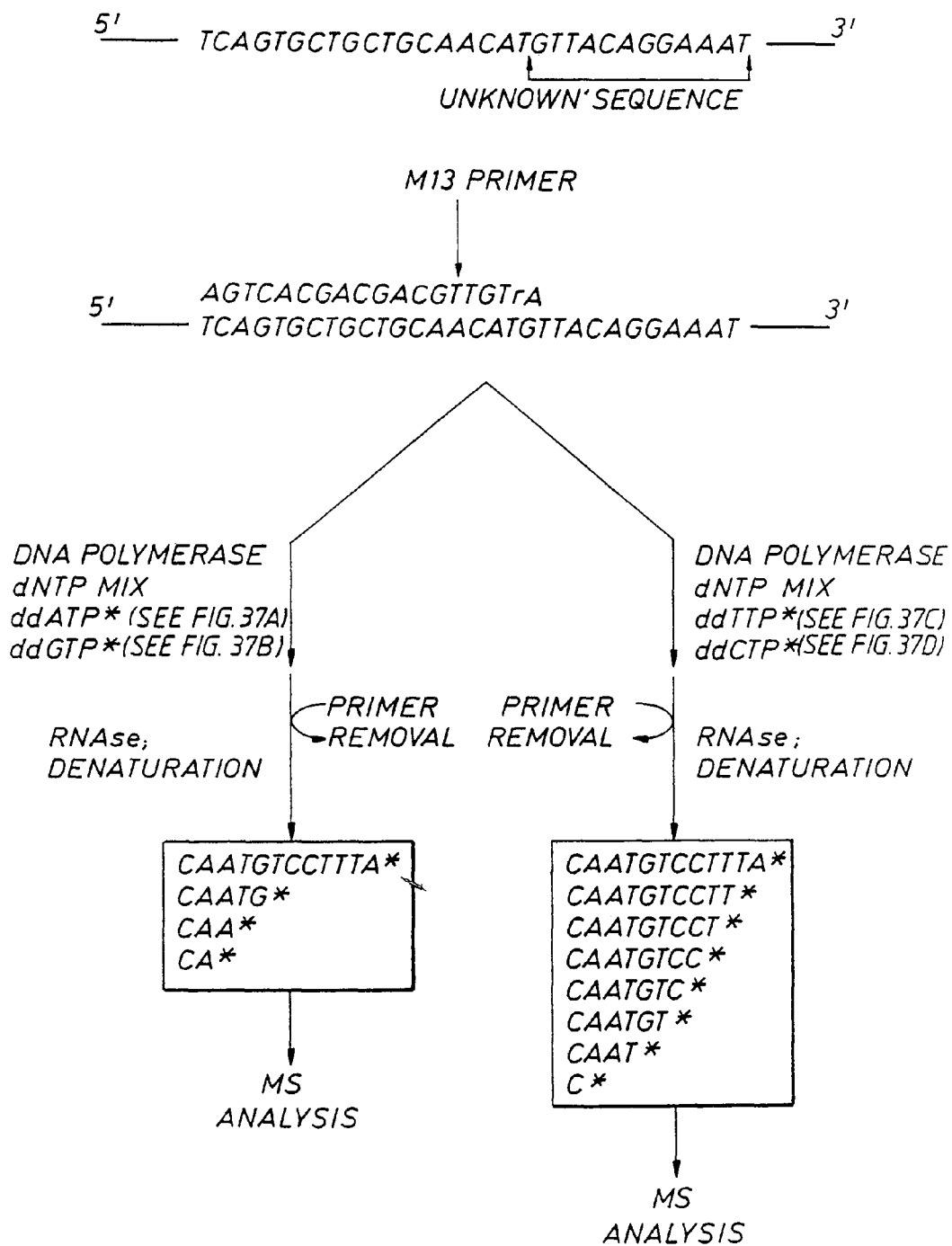
FIG. 36 illustrates an exemplary sequencing technique using the Sanger method (SEQ ID NOS 5-15).
Figure 37A:
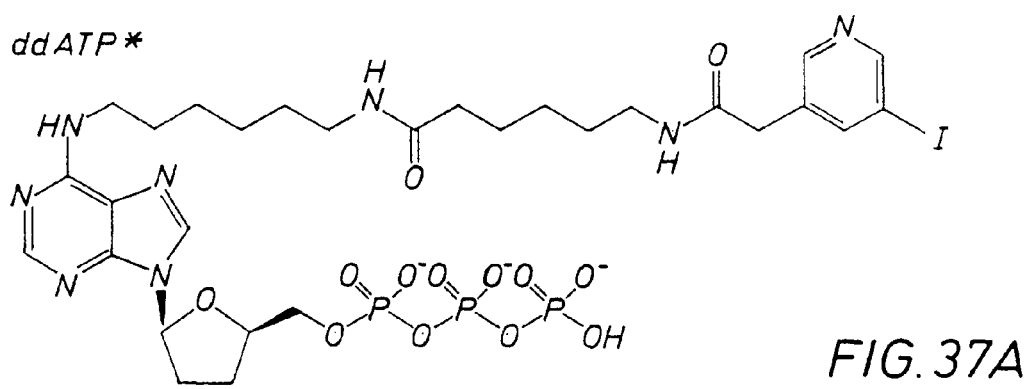
FIGS. 37 A, B, C, and D illustrate modified ddATP, ddGTP, dd TTP, and ddCTP, respectively.
Figure 37B:
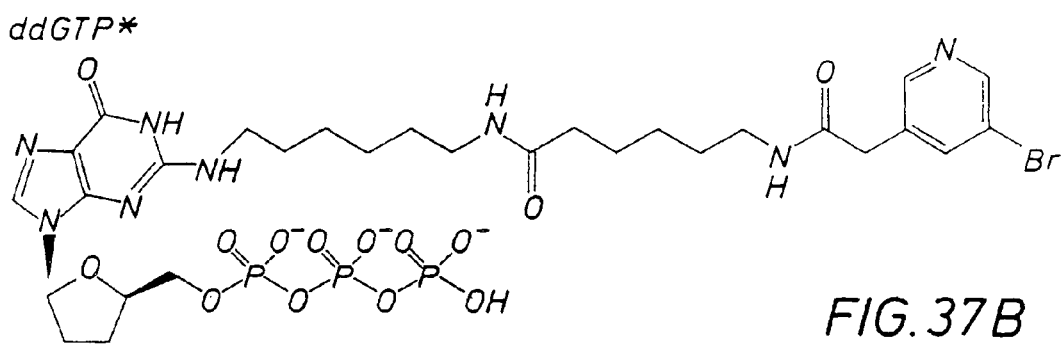
Figure 37C:
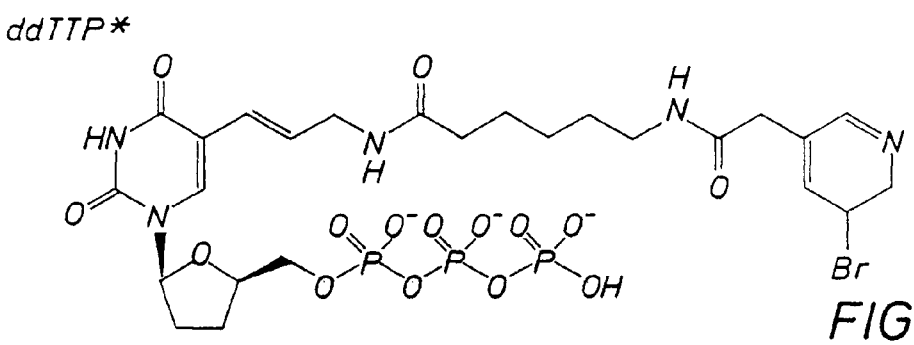
Figure 37D:
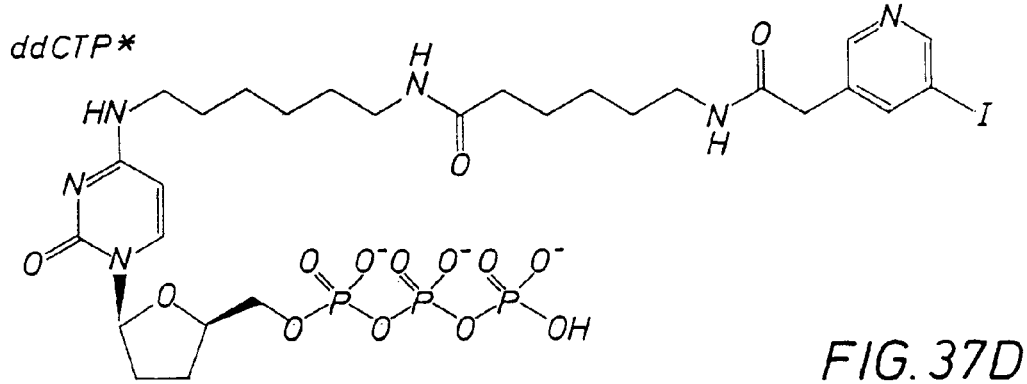

This example illustrates the use of mass defect labels in DNA sequencing applications. The scheme presented (FIG. 36) represents an exemplary sequencing technique using the method of Sanger; however, similar methodology could be applied to other DNA sequencing strategies such as Maxam-Gilbert or PCR or other strategies known to those skilled in the art.

An M13 plasmid carrying a cloned unknown DNA sequence (e.g., d(GTTACAGGAAAT)) (SEQ ID NO: 1) is initially hybridized with an M13 origin of replication primer (d(AGTCACGACGACGTTGT)rA) (SEQ ID NO: 2) that is labeled at the 3' end with rA to make the primer selectively cleavable by RNAse (Integrated DNA Technologies, Inc., Coralville, Iowa). The reaction volume is divided in half and transferred to two tubes. In one tube, polymerase, dNTPs, dGTP, and mass-defect-labeled ddATP* (FIG. 37A) and ddGTP* (FIG. 37B) are added. To the other tube, polymerase, dNTPs, and mass-defect-labeled ddTIP* (FIG. 37C) and ddCTP* (FIG. 37D) are added. The modified ddNTPs shown in FIGS. 37A-D are exemplary and are prepared according to standard procedures (Kricka, L. J., "Nonisotopic DNA Probe Techniques," Academic Press, New York (1992); Keller, G. H. and Manak, M. M., "DNA Probes," Stockton, N.Y. (1989)). As is obvious to those skilled in the art, many other modified ddNTPs are plausible containing purine and pyrimidine bases derivatized with mass defect label moieties and separated by a large assortment of crosslinkers with different lengths and/or compositions. The only requirement is that they are recognized by the DNA polymerase and can be incorporated into the growing fragment. DNA replication and chain extension is initiated by incubation at 37° C. Mass ladders are produced by chain termination with the ddNTPs. A denaturation and cleavage step with RNAse at the end of the reaction removes the chain-terminated product from the template and frees the primer that can be selectively removed by hybridization. The DNA fragments are dissolved in a mass spectrometer-compatible buffer and flown in an ESI-TOF mass spectrometer in negative ion mode. The peaks corresponding to a series of multiply charged ions for each fragment are deconvolved using standard algorithms supplied by the instrument manufacturer (Applied Biosystems) to generate spectra containing only the zero-charge masses. The zero-charge spectra are subsequently centroided also using the instrument supplier's algorithms.

Figure 38:
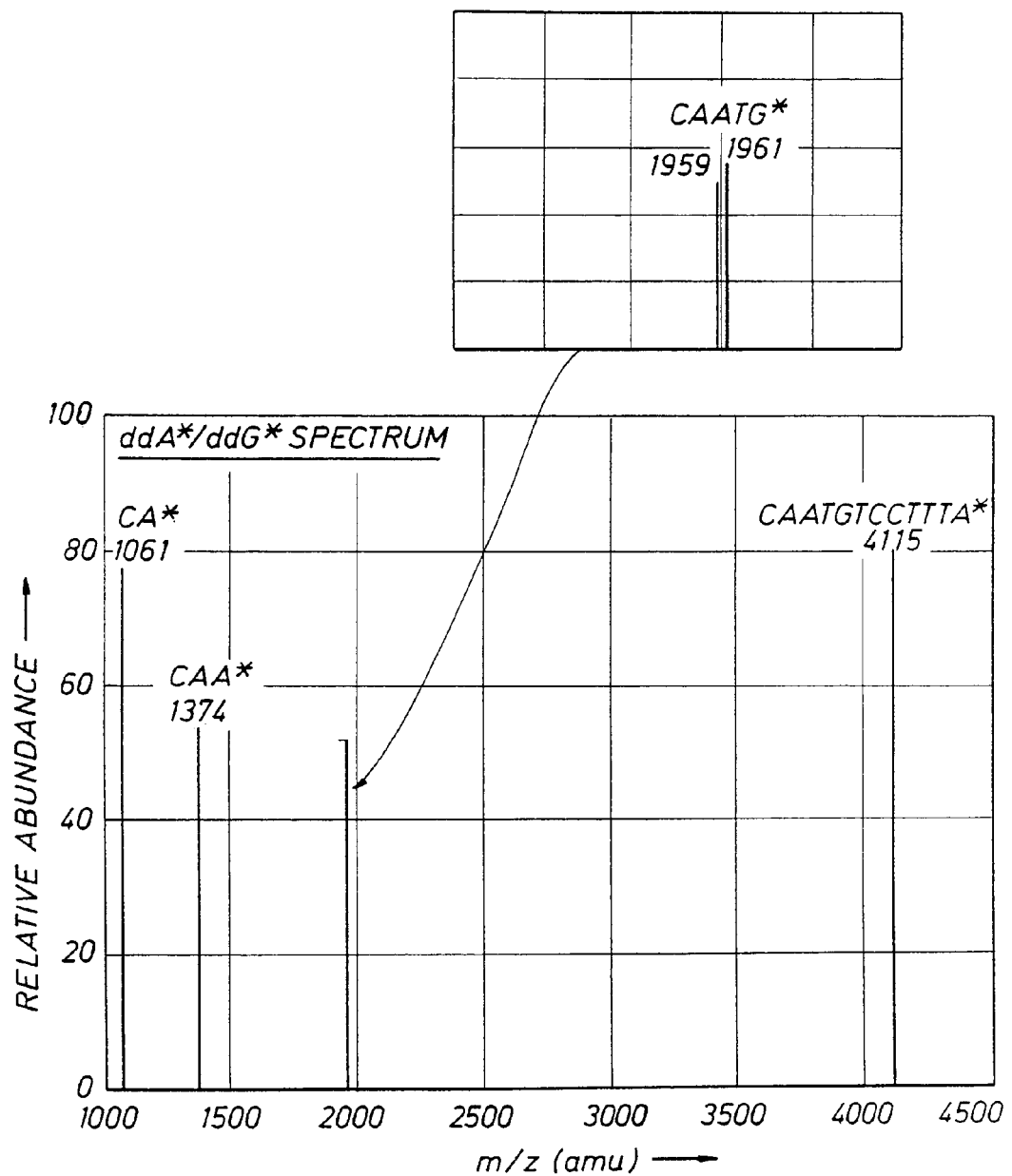
FIG. 38 illustrates an exemplary deconvolved ddA* and ddG* spectrum (SEQ ID NOS 16-17).
Figure 39:
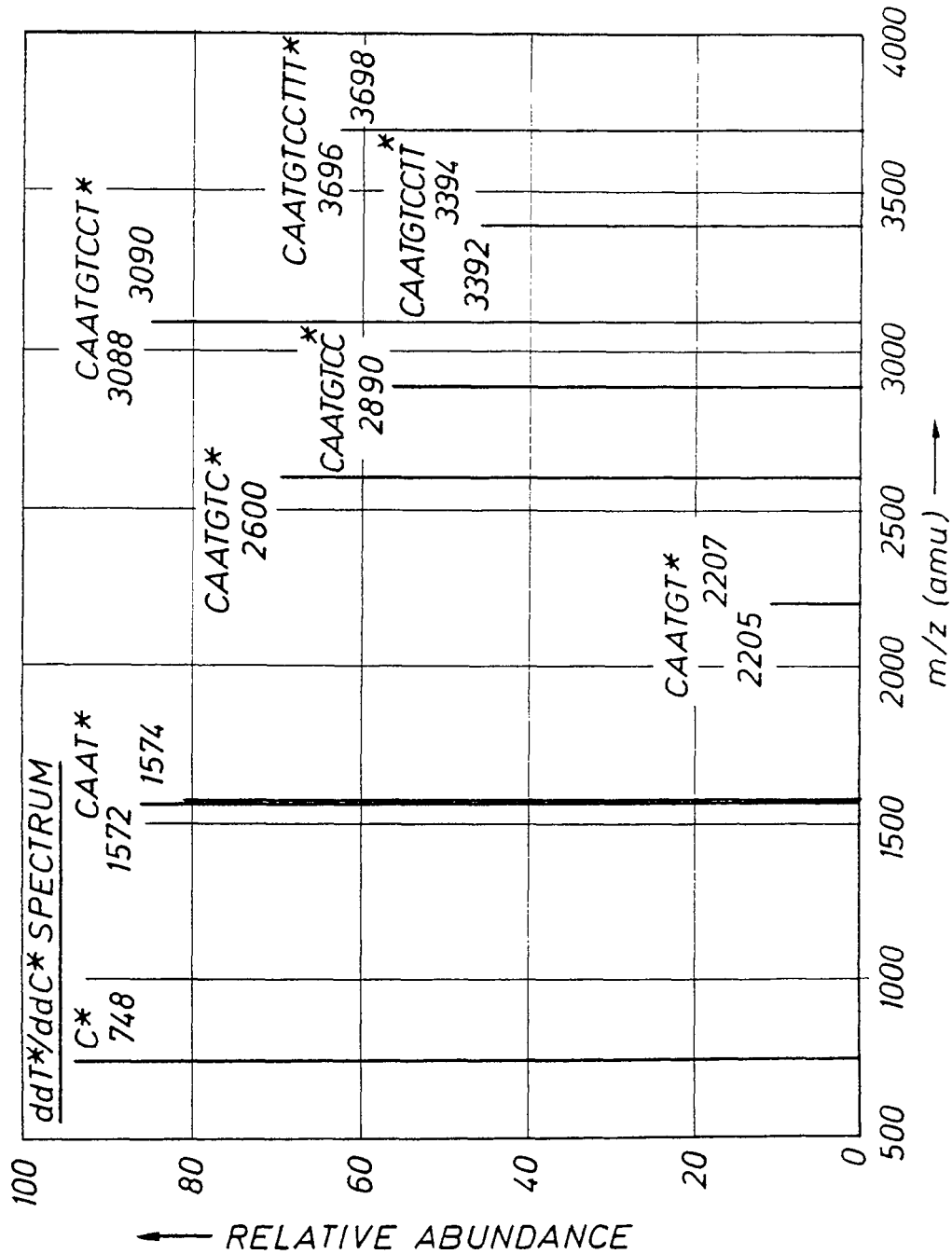
FIG. 39 illustrates an exemplary deconvolved ddT* and ddC* spectrum (SEQ ID NOS 18-24).

The mass spectral data are analyzed as follows. The spectrum from the ddA*- and ddG*-containing sample is deconvolved and chemical noise is eliminated, leaving only peaks that have incorporated bromine or iodine atoms (FIG. 38). The spectrum from the ddT*- and ddC*-containing sample is similarly treated (FIG. 39). Looking at both deconvolved spectra, the highest mass fragment is found (4114.733) in the ddA*/ddG* spectrum (FIG. 38). It can be further deduced that this fragment contains an iodine mass element as there is no isotopic pair; therefore, the last nucleotide in the "unknown" sequence is A. The mass fragment with the next lower mass is a doublet at 3695.611 and 3697.609 which is found in the ddT*/ddC* spectrum (FIG. 39). The doublet indicates incorporation of a bromine atom, and, therefore, the next nucleotide in the sequence is T. This process is repeated until the last peak is found, in this case, a singlet peak at 748.1850 in the ddT*/ddC* spectrum corresponding, therefore, to C. Thus, the sequence ATTTCCTGTAAC (SEQ ID NO: 3) is determined, and when reversed and the nucleotide complements are substituted, the "unknown" sequence GTTACAGGAAAT (SEQ ID NO: 4) is determined, and when reversed and the nucleotide complements are substituted, the "unknown" sequence GTTACAGGAAAT (SEQ ID NO: 4) is determined.

In this example, a DNA segment of approximately 4000 MW is sequenced which is within the specifications for this invention. Since the ability to distinguish mass defect species incorporating one mass-defect atom degrades at masses over 5000, larger DNA segments than the example presented here can be sequenced by either using more mass defect elements in the terminating ddNTPs, or, alternatively, by using the method of the "rolling primer." With the "rolling primer" method, a shorter segment of the desired DNA to be sequenced is obtained using the above procedure, and a new primer is made from this deduced sequence to continue sequencing along the larger DNA strand. In the end, the shorter fragments can be placed end-to-end to reveal the sequence of the unknown DNA.

Example 13

In this example we use the mass defect label (5-Br-3-PAA) to sequence bovine ubiquitin (Sigma-Aldrich). Ubiquitin was labeled by the same procedure described above for myoglobin, except that the protein labeling step was conducted in 100% dimethylsulfoxide. The labeled ubilquitin sample was prepared and introduced to an ESI-TOF mass spectrometer as described above. The resulting mass spectrum was deconvolved and sequenced as described described.

The true ubquitin N-terminal sequence (MQIFVK (SEQ ID NO: 28), obtained from GenBank) was correctly determined when "sequencer" was run to two, three, and four residues. The correct sequence ranked second out of 19 competing possibilities at the first residue. The correct sequence was also ranked second (to MQIFR (SEQ ID NO: 29)) at the fifth residue.

This application is also related to co-pending **U.S. patent application Ser. No. 10/035,349, filed on Oct. 19, 2001, by the same three inventors as this application, and entitled "Mass Defect Labelling for Determination of Oligomer Sequences", and this co-pending application is hereby incorporated herein by reference in its entirety for all purposes.

What is claimed is:

1. A computer implemented method for deriving probability distributions for a plurality of subject peptide sequences useful in calculating a cumulative ranking for peptide sequences of a protein or protein fragment, said method comprising the steps of:
   (i) generating a mass spectrum data of a protein or protein fragment;
   (ii) calculating a first set of m/z values for a first peptide sequence of a length and storing said first set of m/z values in a memory system of said computer;
   (iii) determining a first abundance value for said first peptide sequence using said first set of m/z values and said mass spectrum data, and erasing said first set of m/z values in said memory system;
   (iv) calculating a second set of m/z values for a second peptide sequence of the length and storing said second set of m/z values in said memory system;
   (v) determining a second abundance value for said second peptide sequence using the second set of m/z values and said mass spectrum data;

(vi) mathematically combining the first abundance value and the second abundance value thereby forming an abundance combination for said first and second peptide sequences, and erasing said second set of m/z values in said memory system;

(vii) iterating steps (iv) to (vi) for additional peptide sequences of the length thereby accumulating an abundance combination for a plurality of peptide sequences of the length;

(viii) calculating a subject set of m/z values for each of a plurality of subject peptide sequences of the length and storing said subject sets of m/z values in said memory system;

(ix) determining a subject abundance value for each of said plurality of subject peptide sequences of the length using the corresponding subject set of m/z values and said mass spectrum data; and (x) deriving a probability distribution for each of said plurality of subject peptide sequences by autoscaling said corresponding subject abundance value based on said abundance combination for said plurality of peptide sequences of the length, and erasing said subject sets of m/z values in said memory system, wherein at least one of each of said plurality of probability distributions is retrievable for calculating a cumulative ranking for peptide sequences for said protein or protein fragment.

2. The method of claim 1 wherein
(a) said mathematically combining in step (vi) consists of summing the first abundance value and the second abundance value thereby accumulating a sum for the first and second peptide sequences, and summing the square of said first abundance value and the square of said second abundance value thereby accumulating a sum squared for said first and second peptide sequences;
(b) said abundance combination in step (vii) consists of a sum for said plurality of peptide sequences of length and a sum squared for said plurality peptide sequences of the length;
(c) said autoscaling in step (x) consists of calculating a mean abundance and standard deviation for said plurality of peptide sequences of the length using said sum and said squared sum.

3. The method of claim 1, wherein the length is greater than 1.

4. The method of claim 1, wherein at least one of each of said plurality of probability distributions is a Gaussian distribution.

5. The method of claim 1, wherein at least one of each of said plurality of probability distributions is a Poisson distribution.

6. The method of claim 1, wherein the length is 7 or less.

7. The method of claim 1, wherein a label is attached to the terminus of said protein or protein fragment.

8. The method of claim 7, wherein said label is covalently bonded to said protein prior to generating said mass spectrum data.

9. The method of claim 7, wherein said protein is fragmented by collision-induced dissociation to generate fragments, which are then accelerated toward a detector to generate said mass spectrum data.

10. The method of claim 7, wherein said protein is isolated from other proteins extracted from a sample and wherein said computer which implements said method comprises a digital processing system which executes computer programming instructions.

11. The method of claim 1, wherein said method is performed for each protein in a set of proteins extracted from a biological material and wherein said set of proteins is more than 100 different proteins.

12. The method of claim 1, wherein said mass spectrum is digitally filtered to minimize spectral noise prior to said determining said first abundance value.

13. The method of claim 1, wherein said protein is labeled prior to being fragmented.

14. The method of claim 1, wherein said protein is fragmented and the resulting fragments are labeled.

15. A method as in claim 1, wherein said protein is labeled with a labeling moiety comprising at least one mass defect element having an atomic number from 17 to 77.

16. The method of claim 1, wherein prior to calculating said first set of mass/charge (m/z) values, said method comprises the steps of:
(a) discriminating between a mass spectrum peak associated with the labeled protein and a mass spectrum peak associated with an unlabeled protein, wherein said discriminating is based on the nuclear binding energy of the labeling moiety; and
(b) deconvolving the mass spectrum peak associated with the labeled protein from the mass spectrum peak associated with the unlabeled protein.

17. The method of claim 1, wherein said protein is labeled with a labeling moiety comprising at least one isotope element.

18. The method of claim 17, wherein the first abundance value and the second abundance value are determined using an isotope ranking factor.

19. The method of claim 1, wherein said protein is labeled with a labeling moiety comprising at least one isotope element and at least one mass defect element having an atomic number from 17 to 77, wherein
(a) prior to calculating said first set of mass/charge (m/z) values, said method comprises the steps of:
(1) discriminating between a mass spectrum peak associated with the labeled protein and a mass spectrum peak associated with an unlabeled protein, wherein said discriminating is based on the nuclear binding energy of the labeling moiety; and
(2) deconvolving the mass spectrum peak associated with the labeled protein from the mass spectrum peak associated with the unlabeled protein;
(b) wherein the first abundance value and the second abundance value are determined using an isotope ranking factor.

* * * * *

UNITED STATES PATENT AND TRADEMARK OFFICE
CERTIFICATE OF CORRECTION

PATENT NO. : 8,352,193 B2  
APPLICATION NO. : 11/444215  
DATED : January 8, 2013  
INVENTOR(S) : Luke V. Schneider et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 753 days.

Signed and Sealed this  
Eleventh Day of November, 2014

Michelle K. Lee  
*Deputy Director of the United States Patent and Trademark Office*

SEQUENCE LISTING

<160> NUMBER OF SEQ ID NOS: 29

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gttacaggaa at                                                            12

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtcacgacg acgttgta                                                      18

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atttcctgta ac                                                            12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gttacaggaa at                                                            12

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcagtgctgc tgcaacatgt tacaggaaat                                         30

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
atgttgcagc agcactga                                                    18
```

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
caatgtcctt ta                                                          12
```

<210> SEQ ID NO 8
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
caatg                                                                   5
```

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
caatgtcctt ta                                                          12
```

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
caatgtcctt                                                             10
```

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
caatgtcct                                                               9
```

<210> SEQ ID NO 12
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

```
caatgtcc                                                                8
```

```
<210> SEQ ID NO 13
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 caatgtc                                                                 7

<210> SEQ ID NO 14
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 caatgt                                                                  6

<210> SEQ ID NO 15
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 caat                                                                    4

<210> SEQ ID NO 16
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16 caatg                                                                   5

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caatgtcctt ta                                                          12

<210> SEQ ID NO 18
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18 caat                                                                    4

<210> SEQ ID NO 19
```

```
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 caatgt                                                                      6

<210> SEQ ID NO 20
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 caatgtc                                                                     7

<210> SEQ ID NO 21
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 caatgtcc                                                                    8

<210> SEQ ID NO 22
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 caatgtcct                                                                   9

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
caatgtcctt                                                                 10

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caatgtcctt t                                                               11

<210> SEQ ID NO 25
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

His Ser Asp Ala Val Phe Ile Thr Asp Asn Tyr Arg
 1               5                  10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Leu Ser Asp Gly Glu
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Leu Ser Asp Trp
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Gln Ile Phe Val Lys
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Gln Ile Phe Arg
 1               5
```